(12) United States Patent
Shaw et al.

(10) Patent No.: US 9,096,585 B2
(45) Date of Patent: Aug. 4, 2015

(54) ANTIVIRAL COMPOUNDS AND USES THEREOF

(75) Inventors: Megan Shaw, New York, NY (US); Hans-Heinrich Hoffmann, New York, NY (US); Adolfo Garcia-Sastre, New York, NY (US); Peter Palese, Leonia, NJ (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 210 days.

(21) Appl. No.: 13/700,049

(22) PCT Filed: May 31, 2011

(86) PCT No.: PCT/US2011/038515
§ 371 (c)(1),
(2), (4) Date: Feb. 14, 2013

(87) PCT Pub. No.: WO2011/150413
PCT Pub. Date: Dec. 1, 2011

(65) Prior Publication Data
US 2013/0137678 A1 May 30, 2013

Related U.S. Application Data

(60) Provisional application No. 61/349,606, filed on May 28, 2010.

(51) Int. Cl.
*A61K 31/41* (2006.01)
*A61K 31/515* (2006.01)
(Continued)

(52) U.S. Cl.
CPC .......... *C07D 413/14* (2013.01); *A61K 31/4245* (2013.01); *C07D 413/10* (2013.01); *C07D 413/12* (2013.01); *A61K 31/5377* (2013.01); *A61K 31/55* (2013.01)

(58) Field of Classification Search
CPC . A61K 31/4245; A61K 31/5377; A61K 31/55
USPC .................... 514/364, 217.1, 236.2
See application file for complete search history.

(56) References Cited

U.S. PATENT DOCUMENTS 6,384,064 B2    5/2002   Camden
8,278,342 B2   10/2012   Ricciardi
(Continued)

FOREIGN PATENT DOCUMENTS

WO    WO 2009/136979 A2   11/2009

OTHER PUBLICATIONS

Chu et al. "Analysis of the endocytic pathway mediating the infectious entry of mosquito-borne flavivirus West Nile into *Aedes albopictus* mosquito (C6/36) cells," Virology, 2006, vol. 349, pp. 463-475.*

(Continued)

*Primary Examiner* — Shengjun Wang
(74) *Attorney, Agent, or Firm* — Jones Day

(57) ABSTRACT

Described herein are Compounds, compositions comprising such Compounds, and the use of such Compounds and compositions as anti-viral agents. In one aspect, provided herein are methods of inhibiting viral replication using Compounds described herein or compositions thereof. In another aspect, provided herein are methods for preventing a symptom of a viral infection using a Compound, or a composition thereof. In another aspect, provided herein are methods of treating and/or managing viral infection using a compound or a composition thereof.

6 Claims, 26 Drawing Sheets

Figure 2:
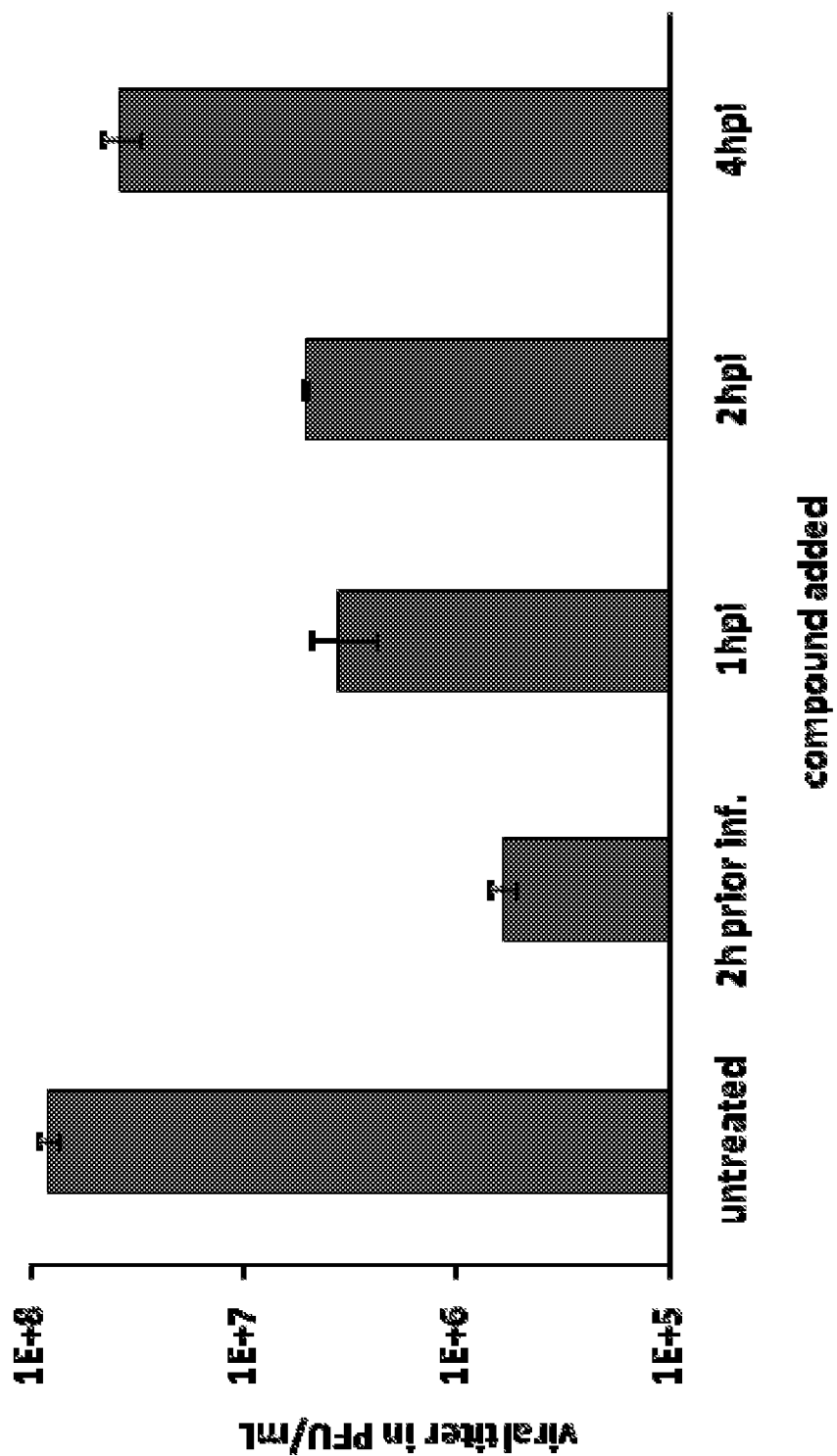

(51) Int. Cl.
| | |
|---|---|
| A61K 31/535 | (2006.01) |
| C07D 413/14 | (2006.01) |
| A61K 31/4245 | (2006.01) |
| C07D 413/10 | (2006.01) |
| C07D 413/12 | (2006.01) |
| A61K 31/55 | (2006.01) |
| A61K 31/5377 | (2006.01) |

(56) References Cited

U.S. PATENT DOCUMENTS

| | | |
|---|---|---|
| 2005/0123902 A1 | 6/2005 | Meneses et al. |
| 2005/0239906 A1 | 10/2005 | Garaci et al. |
| 2009/0162831 A1 | 6/2009 | Delwart et al. |
| 2010/0035887 A1 | 2/2010 | Ricciardi |
| 2011/0105423 A1 | 5/2011 | Shaw |

OTHER PUBLICATIONS

Somvanshi et al. "Comparative proteome analysis of distinct variants of Dengue virus using in silico approach," Internet Journal of Genomics and proteomics, 2009, vol. 4, No. 1. URL: http://www.ispub.com/journal/the internet journal of genomics and proteomics.*
Chen et al., 2004, "Influenza A virus PB1-F2 gene in recent Taiwanese isolates", Emerging Infectious Diseases; 10(4):630-635.
Fabbri et al., 1994, "Export of protein from the endoplasmic reticulum is regulated by a diacylglycerol/phorbol ester binding protein", J Biol Chem; 269(43):26848-26857.
Gschwendt et al., 1994, "Rottlcrin, a novel protein kinase inhibitor", Biochem Biophys Res Commun; 199(1):93-98.
Guggino et al., 2000, "Amiloride-sensitive sodium channels contribute to the woes of the flu", Proc Natl Acad Sci USA, 97(18):9827-9829.
Hoffmann et al., 2008, "Modulation of influenza virus replication by alteration of sodium ion transport and protein kinase C activity", Dept.of Microbiology, Mount Sinai School of Medicine, New York, NY 10029.
Hoffmann et al., 2008, "Modulation of influenza virus replication identified via a high-throughput screening approach", Dept.of Microbiology, Mount Sinai School of Medicine, New York, NY 10029.
International Search Report of International application No. PCT/US2009/001474, dated Jan. 18, 2010.
International Search Report of International application No. PCT/US2011/38515, dated Sep. 13, 2011.
Kistner et al., 1989, "Differential phosphorylation of the nucleoprotein of influenza A viruses", J Gen Virol; 70:2421-2431.
Kleyman et al., 1988, "Amiloride and its analogs as tools in the study of ion transport", J Membrane Biol; 105:1-21.
Kunzelmann et al., 2000, "Influenza virus inhibits amiloride-sensitive $Na^+$ channels in respiratory epithelia", Proc Natl Acad Sci USA; 97(18):10282-10287.
Kurokawa et al., 1990, "Inhibitory effect of protein kinase C inhibitor on the replication of influenza type A virus", J Gen Virol; 71(Pt 9):2149-2155.
Lee et al., 2007, "Crystal structure of the VP4 protease from infectious pancreatic necrosis virus reveals the acyl-enzyme complex for an intermolecular self-cleavage reaction", J Biol Chem; 282(34):24928-24937.
Link et al., 1966, "Interaction of heart glycosides and viruses", Acta Virol; 10:455-461.
Mahmoudian et al., 2009, "Influenza A virus proteins PB1 and NS1 are subject to functionally important phosphorylation by protein kinase C", J Gen Virol; 90(Pt 6):1392-1397.
Nagai et al., 1972, "Inhibition of virus growth by ouabain: effect of ouabain on the growth of HVJ in chick embryo cells", J Virol; 9(2):234-243.
Patterson et al., 1979, "Studies on the mechanism of influenza virus entry into cells", J Gen Virol; 43(223-229).
Rigaut et al., 1991, "Inhibition of VSV infection by staurosporine", J Cell Biol; 115(3Part2):476A.
Root et al., 2000, "Entry of influenza viruses into cells is inhibited by a highly specific protein kinase C inhibitor", J Gen Virol; 81(Pt 10:2697-2705.
Salvatore et al., 2007, "α-defensin inhibits influenza virus replication by cell-mediated mechanism(s)", JID; 196:835-843.
Scholtissek et al., 1986, "Influence of insulin and 12-O-tetradecanoylphorbol-13-acetate (TPA) on influenza virus multiplication", Virus Res; 6:287-294.
Shaw et al., 2008, "Opposing effects on influenza growth by compounds targeting both sodium channels and protein kinase C", Dept. of Microbiology, Mount Sinai School of Medicine, New York, NY 10029 (Abstract only).
Sieczkarski et al., 2003, "Role of protein kinase C βII in influenza virus entry via late endosomes", J Virol; 77(1):460-469.
Wright et al., 2009, "Inhibition of simian virus 40 replication by targeting the molecular chaperone function and ATPase activity of T antigen", Virus Res; 141(1):71-80.
Written Opinion of International application No. PCT/US2009/001474, dated Jan. 18, 2010.
Written Opinion of International application No. PCT/US2011/38515, dated Sep. 13, 2011.
Yi et al., 2008, "A secondary gate as a mechanism for inhibition of the M2 proton channel by amantadine", J Phys Chem; 1 12(27):7977-7979.

* cited by examiner

Fig.1

(Modified from Flint et al., 2003)

ANTIVIRAL COMPOUNDS AND USES THEREOF

This application is a national stage application of International Patent Application No. PCT/US2011/038515, filed May 31, 2011, which claims the benefit of priority to the U.S. Provisional Application Ser. No. 61/349,606, filed on May 28, 2010, each of which is incorporated herein by reference in its entirety and for all purposes.

This invention was made with government support under U01 AI1074539, U54 AI057158, HHSN266200700010C, PO1 AI058113, R21AI083673 and HHSN272200900032C awarded by the National Institute of Health. The United States Government has certain rights in the invention.

1. INTRODUCTION

Described herein are Compounds, compositions comprising such Compounds, and the use of such Compounds and compositions as anti-viral agents. In one aspect, provided herein are methods of inhibiting viral replication using Compounds described herein or compositions thereof. In another aspect, provided herein are methods for preventing a symptom of a viral infection using a Compound or a composition thereof. In another aspect, provided herein are methods of treating and/or managing viral infection using a compound or a composition thereof.

2. BACKGROUND

Viral infection and viral disease poses severe threat to human health. Governments all over the world have cooperated to combat against viral infection and viral disease. Viral diseases such as Dengue fever, influenza, hepatitis C, HIV have affected many worldwide. Unlike antibiotics, there are fewer antiviral drugs available. Unlike antibiotics, currently available antiviral agents are usually effective against only a limited number of viruses. Thus, there is an urgency in the development of a new class of antiviral agents that is effective against a broad spectrum of viruses.

3. SUMMARY

Described herein are Compounds (see Section 5.1) and the use of such Compounds to inhibit the replication of a variety of viruses. Compounds described herein were unexpectedly found to inhibit the replication of viruses from diverse families. For example, Compounds were found to unexpectedly inhibit the replication of a DNA virus, a positive-sense, single-stranded RNA virus, a negative-sense, single-stranded RNA virus, a double-stranded RNA virus and a retrovirus.

Without being bound by any theory, the Compounds are believed to inhibit viral polymerase activity without adversely affecting cellular polymerase activity. Given the differences in RNA polymerases and DNA polymerases utilized by various RNA and DNA viruses, it is a surprising discovery that the Compounds exhibit antiviral activity against a broad spectrum of viruses with a good safety/cytotoxicity profile. For example, the negative-sense, single-stranded RNA viruses utilize virally encoded RNA-dependent RNA polymerase, whereas positive-sense, single-stranded RNA viruses use host RNA polymerase or reverse transcriptase as in retrovirus, and DNA viruses use virally encoded DNA-dependant RNA polymerase or host RNA polymerase. It is also found that the antiviral activity of A3 can be linked to a cellular protein, dihydroorotate dehydrogenase (DHODH), which is an enzyme in the de novo pyrimidine biosynthesis pathway. Viral replication of both RNA and DNA viruses can be restored in the presence of excess uracil, which promotes pyrimidine salvage, or excess orotic acid, which is the product of DHODH in the de novo pyrimidine biosynthesis pathway. A3 thus acts by depleting pyrimidine pools, which are crucial for efficient virus replication.

In one aspect, described herein are methods for inhibiting or reducing the replication of a virus as well as a broad spectrum of viruses, including a DNA virus, a positive-sense, single-stranded RNA virus, a negative-sense, single-stranded RNA virus, a double-stranded RNA virus and a retrovirus. In one embodiment, a method for inhibiting or reducing the replication of a virus comprises contacting a cell infected with a virus (e.g., a DNA virus, a positive-sense, single-stranded RNA virus, a negative-sense, single-stranded RNA virus, a double-stranded RNA virus or a retrovirus) with a Compound or composition thereof in an amount sufficient to inhibit or reduce the replication of the virus. In another embodiment, a method for inhibiting or reducing the replication of a virus (e.g., a DNA virus, a positive-sense, single-stranded RNA virus, a negative-sense, single-stranded RNA virus, a double stranded RNA virus or a retrovirus) comprises: (a) infecting a cell with a virus (e.g., a DNA virus, a positive-sense, single-stranded RNA virus, a negative-sense, single-stranded RNA virus, a double stranded RNA virus or a retrovirus); and (b) contacting the cell with a Compound or a composition thereof, in an amount sufficient to inhibit or reduce replication of the virus. In certain embodiments, the virus is not a negative-sense single-stranded RNA virus. In specific embodiments, the cell is contacted with the Compound in vitro. In one embodiment, the cell is contacted with the Compound prior to infection with a virus (e.g., a DNA virus, a positive-sense, single-stranded RNA virus, a negative-sense, single-stranded RNA virus, a double stranded RNA virus or a retrovirus). In certain embodiments, the cell is in contact with the Compound 1 hr, 2 hrs, 3 hrs, 4 hrs, 5 hrs, 6 hrs, 7 hrs, 8 hrs, 9 hrs, 10 hrs, 11 hrs, 12 hrs, 16 hrs, 18 hrs, 24 hrs, 30 hrs, 36 hrs, 48 hrs, 1 week, 2 weeks prior to infection with a virus (e.g., a DNA virus, a positive-sense, single-stranded RNA virus, a negative-sense, single-stranded RNA virus, a double stranded RNA virus or a retrovirus). In certain embodiments, the cell is contacted with the Compound 1 hr, 2 hrs, 3 hrs, 4 hrs, 5 hrs, 6 hrs, 7 hrs, 8 hrs, 9 hrs, 10 hrs, 11 hrs, 12 hrs, 16 hrs, 18 hrs, 24 hrs, 30 hrs, 36 hrs, 48 hrs, 1 week, 2 weeks after infection with a virus (e.g., a DNA virus, a positive-sense, single-stranded RNA virus, a negative-sense, single-stranded RNA virus, a double stranded RNA virus or a retrovirus).

In another embodiment, described herein are methods for inhibiting or reducing the replication of a virus (e.g., a DNA virus, a positive-sense, single-stranded RNA virus, a negative-sense, single-stranded RNA virus, a double stranded RNA virus or a retrovirus), comprising: (a) contacting a cell with a Compound in an amount sufficient to inhibit or reduce replication of a virus (e.g., a DNA virus, a positive-sense, single-stranded RNA virus, a negative-sense, single-stranded RNA virus, a double-stranded RNA virus or a retrovirus); and (b) infecting the cell with the virus (e.g., a DNA virus, a positive-sense, single-stranded RNA virus, a negative-sense, single-stranded RNA virus, a double-stranded RNA virus or a retrovirus). In one embodiment, a cell(s) is infected with a virus and concurrently contacted with a Compound or a composition thereof. In certain embodiments, the virus is not a negative-sense, single-stranded RNA virus. In specific embodiments, the cell is contacted with the Compound in vitro. In certain embodiments, the Compound has the formula AH. In some embodiments, the Compound has the formula AI. In certain embodiments, the Compound has the formula A3, A3-2, A3-3, A3-4, A3-5, or A3-6. In some embodiments, the Compound is not A3-B and/or A3-11.

In one embodiment, described herein is a method of inhibiting replication of a DNA virus, a positive-sense, single-stranded RNA virus, a double-stranded RNA virus or a retrovirus, comprising contacting a first composition comprising a cell(s) infected with a DNA virus, a positive-sense, single-stranded RNA virus, a double-stranded RNA virus or a retrovirus with a second composition comprising one of the following Compounds: a Compound with the formula A3-H, A3-I, or A3-J, including a Compound with the formula A3, A3-1, A3-2, A3-3, A3-4, A3-5, A3-6; A3-7, A3-8, A3-9, A3-11, or A3-12. In certain specific embodiments, the Compound has a formula A3-2 or A3-5. In another embodiment, described herein is a method of inhibiting replication of a DNA virus, a positive-sense, single-stranded RNA virus, a double-stranded RNA virus or a retrovirus, comprising contacting a first composition comprising a cell(s) and one of the following Compounds: a Compound of the formula A3-H, A3-I, or A3-J, including a Compound with the formula A3, A3-1, A3-2, A3-3, A3-4, A3-5, A3-6; A3-7, A3-8, A3-9, A3-11, A3-12 with a second composition comprising a DNA virus, a positive-sense, single-stranded RNA virus, a double-stranded RNA virus or a retrovirus. In one embodiment, a cell(s) is infected with a virus and concurrently contacted with a Compound or a composition thereof. In certain specific embodiments, the Compound has a formula A3, A3-2, A3-3, A3-4, A3-5, or A3-6. In some embodiments, the Compound has a formula A3-2 or A3-5. In some embodiments, the Compound has the formula A3-I. In certain embodiments, the DNA virus is a cytoplasmic double-stranded DNA virus. In certain embodiments, the cytoplasmic double-stranded DNA virus is a Poxvirus (Poxyiridae). In certain embodiments, the Poxvirus is a vaccinia virus. In certain embodiments, the DNA virus is a nuclear double-stranded DNA virus. In certain embodiments, the cytoplasmic double-stranded DNA virus is an Adenovirus. In certain embodiments, the Adenovirus is a human adenovirus. In certain embodiments, the human adenovirus is HAdV. In certain embodiments, the HAdV is HAdv-A, HAdV-B, HAdV-C, HAdV-D, HAdV-E, or HAdV-F. In certain embodiments, the RNA virus is a positive-sense, single-stranded RNA virus. In certain embodiments, the positive-sense, single-stranded RNA virus is Flavivirus (Flaviviridae). In certain embodiments, the Flavivirus is a Dengue virus, hepatitis C virus, or a West Nile virus. In certain embodiments, the positive-sense single-stranded RNA virus is Togavirus (Togaviridae). In certain embodiments, the Togavirus is Sindbis virus. In certain embodiments, the positive-sense single-stranded RNA virus is a retrovirus (Retroviridae). In certain embodiments, the retrovirus is human immunodeficiency virus (HIV). In certain embodiments, the HIV is HIV type 1.

In another embodiment, described herein is a method of inhibiting replication of a negative-sense, single-stranded RNA virus, comprising contacting a first composition comprising a cell(s) and one of the following compounds: a Compound of the formula A3-J, including a Compound with the formula A3-1, A3-7, A3-8, A3-9, A3-11, or A3-12, with a second composition comprising a negative-sense, single-stranded RNA virus. In another embodiment, described herein is a method of inhibiting replication of a negative-sense, single-stranded RNA virus, comprising contacting a first composition comprising a cell(s) infected with a negative-sense, single-stranded RNA virus with a second composition comprising one of the following compounds: a Compound with the formula A3-J, including a Compound with the formula A3-1, A3-7, A3-8, A3-9, A3-11, or A3-12. In another embodiment, described herein is a method of inhibiting replication of a negative-sense, single-stranded RNA virus, comprising infecting a cell(s) with a negative-sense, single-stranded virus and concurrently contacting the cell(s) with a Compound or a composition thereof. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula A1. In some embodiments, the Compound does not have formula of A3-8 and/or A3-11. In other embodiments, the Compound is not A3-2 and/or A3-5.

In another aspect, described herein are methods for inhibiting or reducing replication of a virus (e.g., a, DNA virus, a positive-sense, single-stranded RNA virus, a negative-sense, single-stranded RNA virus, a double-stranded RNA virus or a retrovirus) in a subject, comprising administering a Compound or a composition thereof to a subject in need thereof. In certain embodiments, the virus is not a negative-sense, single-stranded RNA virus. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula A1. In some embodiments, the Compound does not have formula of A3-8 and/or A3-11. In other embodiments, the Compound is not A3-2 and/or A3-5.

In one embodiment, described herein is a method of inhibiting replication of a DNA virus, a positive-sense, single-stranded RNA virus, a double stranded RNA virus or a retrovirus in a subject, comprising administering a Compound of the formula A3-H, A3-I, or A3-J, including Compounds with the formula A3, A3-1, A3-2, A3-3, A3-4, A3-5, A3-6, A3-7, A3-8, A3-9, A3-11, or A3-12 or a composition thereof, to a subject in need thereof. In certain embodiments, the virus is HIV. In certain embodiment, the virus is HIV type-1. In some embodiments, the subject is a human. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula A1. In some embodiments, the Compound does not have formula of A3-8 and/or A3-11. In other embodiments, the Compound is not A3-2 and/or A3-5.

In certain embodiments, described herein are methods of inhibiting replication of a negative-sense, single-stranded RNA virus in a subject, comprising administering a Compound of the formula A3-J, including a Compound with the formula A3-1, A3-7, A3-8, A3-9, A3-11, or A3-12, to a subject in need thereof. In certain embodiments, the Compound is administered to the subject in a pharmaceutical composition. In specific embodiments, the virus is Sendai virus, Vesicular Stomatitis virus, Newcastle disease virus, or respiratory syncytial virus. In specific embodiments, the subject is human. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula A1. In some embodiments, the Compound does not have formula of A3-8 and/or A3-11. In other embodiments, the Compound is not A3-2 and/or A3-5.

In another aspect, described herein are methods of preventing viral infection (e.g., a DNA virus, a positive-sense, single-stranded RNA virus, a double stranded RNA virus and a retrovirus infection) in a subject, comprising administering to a subject in need thereof an effective amount of a Compound. In certain embodiments, the Compound is administered to the subject in a pharmaceutical composition. In specific embodiments, the subject is human. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula AI. In some embodiments, the Compound does not have formula of A3-8 and/or A3-11. In other embodiments, the Compound is not A3-2 and/or A3-5.

In another aspect, described herein are methods for preventing the pathological state resulting from a viral infection, comprising administering a Compound or a composition thereof to a subject in need thereof. In some embodiments, the viral infection is a DNA virus, a positive-sense, single-stranded RNA virus, a negative-sense, single-stranded RNA virus, a double-stranded RNA virus or a retrovirus infection. In certain embodiments, the viral infection is not an infection from a negative-sense, single-stranded RNA virus. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula A1. In some embodiments, the Compound does not have formula of A3-8 and/or A3-11. In other embodiments, the Compound is not A3-2 and/or A3-5.

In another aspect, described herein are methods for preventing a symptom of viral infection, comprising administering a Compound or a composition thereof to a subject in need thereof. In some embodiments, the viral infection is a DNA virus, a positive-sense, single-stranded RNA virus, a negative-sense, single-stranded RNA virus, a double-stranded RNA virus or a retroviral infection. In certain embodiments, the virus is not a negative-sense, single-stranded RNA virus. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula A1. In some embodiments, the Compound does not have formula of A3-8 and/or A3-11. In other embodiments, the Compound is not A3-2 and/or A3-5.

In certain embodiments, described herein are methods of preventing a symptom of a viral infection (e.g., a DNA virus, a positive-sense, single-stranded RNA virus, a double-stranded RNA virus or a retroviral infection) in a subject, comprising administering to a subject in need thereof an effective amount of a Compound with the formula A3-H, A3-I, or A3-J, including, but not limited to A3, A3-1, A3-2, A3-3, A3-4, A3-5, A3-6, A3-7, A3-8, A3-9, A3-11, or A3-12. In certain embodiments, the Compound is administered to the subject in a pharmaceutical composition. In specific embodiments, the subject is human. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula AI. In some embodiments, the Compound does not have formula of A3-8 and/or A3-11. In other embodiments, the Compound is not A3-2 and/or A3-5.

In certain embodiments, provided herein is a method of preventing a symptom of a negative-sense, single-stranded RNA viral infection in a subject, comprising administering to a subject in need thereof an effective amount of a Compound with the formula A3-J, including a Compound with the formula A3-1, A3-7, A3-8, A3-9, A3-11 or A3-12. In specific embodiments, the subject is human. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula A1. In some embodiments, the Compound does not have formula of A3-8 and/or A3-11. In other embodiments, the Compound is not A3-2 and/or A3-5.

In another aspect, described herein are methods of treating and/or managing a viral infection, comprising administering a Compound or a composition thereof to a subject in need thereof. In some embodiments, the viral infection is a DNA virus, a positive-sense, single-stranded RNA virus, a negative-sense, single-stranded RNA virus, a double-stranded RNA virus and a retrovirus infection. In certain embodiments, the virus is not a negative-sense, single-stranded RNA virus. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula AI. In some embodiments, the Compound does not have formula of A3-8 and/or A3-11. In other embodiments, the Compound is not A3-2 and/or A3-5.

In certain embodiments, provided herein is a method of treating and/or managing a DNA virus, a positive-sense, single-stranded RNA virus, a double-stranded RNA virus or a retrovirus infection in a subject, comprising administering to a subject in need thereof an effective amount of a Compound with the formula A3-H, A3-I, or A3-J, including, but not limited to A3, A3-1, A3-2, A3-3, A3-4, A3-5, A3-6, A3-7, A3-8, A3-9, A3-11, or A3-12. In certain embodiments, the Compound is administered in a pharmaceutical composition. In specific embodiments, the subject is human. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula AI. In some embodiments, the Compound does not have formula of A3-8 and/or A3-11. In other embodiments, the Compound is not A3-2 and/or A3-5.

In certain embodiments, provided herein is a method of treating and/or managing a negative-sense, single-stranded RNA viral infection in a subject, comprising administering to a subject in need thereof an effective amount of a Compound with the formula A3-J, including a Compound with the formula A3-1, A3-7, A3-8, A3-9, A3-11 or A3-12. In certain embodiments, the Compound is administered in a pharmaceutical composition. In specific embodiments, the subject is human. In certain embodiments, the Compound has the formula A3, A3-2, A3-3, A3-4, A3-5 or A3-6. In certain embodiments, the Compound has a formula A3-2 or A3-5. In some embodiments, the Compound has a formula AH. In certain embodiments, the Compound has formula AI. In some embodiments, the Compound does not have formula of A3-8 and/or A3-11. In other embodiments, the Compound is not A3-2 and/or A3-5.

In certain embodiments, the Compound has the formula A3-H, A3-I, or A3-J. (see Section 5.1). In certain specific embodiments, the Compound has the formula A3, A3-2, A3-3, A3-4, A3-5, A3-6. In other embodiments, the Compound has the formula A3-1, A3-7, A3-8, A3-9, A3-11, or A3-12. In certain specific embodiments, the Compound has a formula A3-2 or A3-5.

Any type, subtype, or strain of a DNA virus, a positive-sense, single-stranded RNA virus, a negative-sense single-stranded RNA virus, a double-stranded RNA virus or a retrovirus may be used as described herein. In a specific embodiment, the positive-sense, single-stranded RNA virus is an enveloped virus. In a specific embodiment, the positive-sense, single-stranded RNA virus is a non-enveloped virus. In certain embodiments, the DNA virus is a cytoplasmic double-stranded DNA virus. In certain embodiments, the cytoplasmic double-stranded DNA virus is a Poxvirus (Poxyiridae). In certain embodiments, the Poxvirus is a vaccinia virus. In certain embodiments, the DNA virus is a nuclear double-stranded DNA virus. In certain embodiments, the cytoplasmic double-stranded DNA virus is an Adenovirus. In certain embodiments, the Adenovirus is a human adenovirus. In certain embodiments, the human adenovirus is HAdV. In certain embodiments, the HAdV is HAdv-A, HAdV-B, HAdV-C, HAdV-D, HAdV-E, or HAdV-F. In certain embodiments, the RNA virus is a positive-sense, single-stranded RNA virus. In certain embodiments, the positive-sense, single-stranded RNA virus is Flavivirus (Flaviviridae). In certain embodiments, the Flavivirus is a Dengue virus, hepatitis C virus, or a West Nile virus. In certain embodiments, the positive-sense single-stranded RNA virus is Togavirus (Togaviridae). In certain embodiments, the Togavirus is Sindbis virus. In certain embodiments, the positive-sense single-stranded RNA virus is a retrovirus (Retroviridae). In certain embodiment, the retrovirus is human immunodeficiency virus (HIV). In certain embodiment, the HIV is HIV type 1. In certain embodiments, the negative-sense single-stranded RNA virus is an orthomyxovirus (orthomyxoviridae). In certain embodiments, the negative-sense, single-stranded RNA virus is a non-segmented virus. In other embodiments, the negative-sense, single-stranded RNA virus is a segmented virus. In certain embodiments, the orthomyxovirus is influenza virus. In certain embodiments, the influenza virus is influenza virus A. In certain embodiments, the influenza virus is influenza virus B. In certain embodiments, the negative-sense single-stranded RNA is a rhabdovirus. In certain embodiments, the rhabdovirus is a Vesicular Stomatitis virus. In certain embodiments, the negative-sense single-stranded RNA is a paramyxovirus. In certain embodiments, the paramyxovirus is a Newcastle disease virus or respiratory syncytial virus. In certain embodiments, the paramyxovirus is Sendai virus. In some embodiments, the DNA virus, positive-sense, single-stranded RNA virus, double-stranded RNA virus or retrovirus is attenuated.

3.1 Terms

As used herein, the terms "Compound(s)" and "Compound(s) described herein" include Compounds of formulas A3-H, A3-I, A3-J, A3, A3-1, A3-2, A3-3, A3-4, A3-5, A3-6, A3-7, A3-8, A3-9, A3-11, A3-12 and pharmaceutically acceptable salts, hydrates, solvates, prodrugs and stereoisomers thereof. In a specific embodiment, the terms "Compound(s)" and "Compound(s) described herein" include those set forth in Section 5.1.

As used herein, the term "about" or "approximately" when used in conjunction with a number refers to any referenced number or any number within 1%, 5% or 10% of the referenced number.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduce or ameliorate the severity of a viral infection or a symptom associated therewith; (ii) reduce the duration of a viral infection or a symptom associated therewith; (iii) prevent the progression of a viral infection or a symptom associated therewith; (iv) cause regression of a viral infection or a symptom associated therewith; (v) prevent the development or onset of a symptom associated with a viral infection; (vi) prevent the pathological disease state resulting from the presence of a virus; (vii) reduce the number of symptoms associated with viral infection; (viii) prevent the recurrence of a viral infection or a symptom associated therewith; (ix) reduce or prevent the spread of a virus from one cell to another cell, one tissue to another tissue, or one organ to another organ; (x) prevent or reduce the spread of a virus from one subject to another subject; (xi) reduce organ failure associated with a viral infection; (xii) reduce the incidence of hospitalization; (xiii) reduce hospitalization of a subject; (xiv) reduce hospitalization length; (xv) increase the survival of a subject with a viral infection; (xvi) eliminate a virus infection; (xvii) inhibit or reduce virus replication; (xviii) inhibit or reduce the entry of a virus into a host cell(s); (xix) inhibit or reduce replication of the viral genome; (xx) inhibit or reduce synthesis of viral proteins; (xxi) inhibit or reduce assembly of viral particles; (xxii) inhibit or reduce release of viral particles from a host cell(s); (xxiii) reduce viral titer; and/or (xxiv) enhance or improve the prophylactic or therapeutic effect(s) of another therapy. In certain other embodiments, a "effective amount" is the amount of a Compound that results in a reduction in viral titer by 1.5 to 10 logs, 1.5 to 5 logs, 2 to 10 logs, 2 to 5 logs, or 2 to 4 logs in a subject administered a Compound relative to the viral titer in a subject or group of subjects (e.g., two, three, five, ten or more subjects) not administered a Compound.

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject with a viral infection. In certain embodiments, the therapies are administered concurrently. In other embodiments, the therapies are administered sequentially. In certain embodiments, the therapies can be contained in separate containers or in the same container. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with a viral infection.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In one embodiment, an infection refers to the pathological state resulting from the presence of the virus in a cell or a subject, or by the invasion of a cell or subject by the virus.

As used herein, the numeric term "log" refers to $\log_{10}$.

In certain embodiments, a subject is administered one or more therapies to "manage" a disease so as to prevent the progression or worsening of the disease associated with an infection by a virus.

As used herein, the phrase "multiplicity of infection" or "MOI" is the average number of virus per infected cell. The MOI is determined by dividing the number of virus added (ml added×PFU) by the number of cells added (ml added x cells/ml).

As used herein, the terms "prevent," "preventing" and "prevention" in the context of the administration of a therapy(ies) to a subject to prevent a viral infection refer to a prophylactic effect resulting from the administration of a therapy or a combination of therapies. In specific embodiments, the following effects resulting from the administration of a therapy or a combination of therapies: (i) the inhibition of the development or onset of a symptom associated with a viral infection; (ii) the prevention of the pathological disease state resulting from the presence of a virus (i.e., disease); (iii) reduction in the number of symptoms associated with viral infection; (iv) the reduction in incidence of hospitalization; (v) the reduction in hospitalization of a subject; (vi) the elimination of a virus infection; (vii) the inhibition or reduction of virus replication; (viii) the inhibition or reduction of the entry of a virus into a host cell(s); (ix) the inhibition or reduction of replication of the viral genome; (x) the inhibition or reduction of synthesis of viral proteins; (xi) the inhibition or reduction of assembly of viral particles; (xii) the inhibition or reduction of release of viral particles from a host cell(s); (xiii) the reduction of viral titer; and/or (xiv) the enhancement or improvement in the prophylactic effect(s) of another therapy.

As used herein, the term "purified," in the context of a Compound that is chemically synthesized, refers to a Compound that is substantially free of chemical precursors or other chemicals when chemically synthesized. In a specific embodiment, the Compound is 60%, preferably 65%, 70%, 75%, 80%, 85%, 90%, or 99% free of other, different Compounds. The purity of a Compound can be determined by one skilled in the art using any known method including, but not limited to, HPLC coupled to a means for detection, mass spectrometry or UV spectrometry.

As used herein, the terms "purified" and "isolated" when used in the context of a Compound (including proteinaceous agents such as peptides) that is obtained from a natural source, e.g., cells, refers to a Compound which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. The phrase "substantially free of natural source materials" refers to preparations of a Compound that has been separated from the material (e.g., cellular components of the cells) from which it is isolated. Thus, a Compound that is isolated includes preparations of a Compound having less than about 30%, 20%, 10%, 5%, 2%, or 1% (by dry weight) of cellular materials and/or contaminating materials.

As used herein, the term "purified" in the context of viruses refers to a virus which is substantially free of cellular material and culture media from the cell or tissue source from which the virus is derived. The language "substantially free of cellular material" includes preparations of virus in which the virus is separated from cellular components of the cells from which it is isolated or recombinantly produced. Thus, virus that is substantially free of cellular material includes preparations of virus having less than about 30%, 20%, 10%, or 5% (by dry weight) of virus (also referred to herein as a "contaminating cellular material"). The virus is also substantially free of culture medium, i.e., culture medium represents less than about 20%, 10%, or 5% of the volume of the virus preparation. A virus can be purified using routine methods known to one of skill in the art including, but not limited to, chromatography and centrifugation.

As used herein, the term "isolated" in the context of viruses refers to a virus which is substantially free of other types of viruses from the cell or tissue source from which the virus is derived. An isolated virus includes preparation of a specific type of virus in which a particular type of virus is separated from other types of viruses and from cellular components of the cells from which it is isolated or recombinantly produced. A virus can be isolated using routine methods known to one of skill in the art, such as but not limited to plaque purification.

As used herein, the terms "replication," "viral replication" and "virus replication" in the context of a virus refer to one or more, or all, of the stages of a viral life cycle which result in the propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "replication," "viral replication" and "virus replication" refer to the replication of the viral genome. In other embodiments, the terms "replication," "viral replication" and "virus replication" refer to the synthesis of viral proteins.

As used herein, the terms "subject" or "patient" are used interchangeably to refer to an animal (e.g., birds, reptiles, and mammals). In certain embodiments, the subject is a mammal. In some embodiments, the subject is a non-primate (e.g., a camel, donkey, zebra, cow, pig, horse, goat, sheep, cat, dog, rat, and mouse) or a primate (e.g., a monkey, chimpanzee, and a human). In certain embodiments, the subject is a non-human mammal. In some embodiment, the subject is a farm animal (e.g., a cow, pig, horse, goat or sheep), a pet (e.g., a dog or cat), and/or a bird (e.g., a chicken or duck). In specific embodiments, the subject is a human.

As used herein, the term "premature human infant" refers to a human infant born at less than 37 weeks of gestational age.

As used herein, the term "human infant" refers to a newborn to 1 year old year human.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the term "synergistic," in the context of the effect of therapies, refers to a combination of therapies which is more effective than the additive effects of any two or more single therapies. In a specific embodiment, a synergistic effect of a combination of therapies permits the use of lower dosages of one or more of therapies and/or less frequent administration of said therapies to a subject with a viral infection. In certain embodiments, the ability to utilize lower dosages of therapies (e.g., prophylactic or therapeutic agents) and/or to administer said therapies less frequently reduces the toxicity associated with the administration of said therapies to a subject without reducing the efficacy of said therapies in the prevention or treatment of a viral infection. In some embodiments, a synergistic effect results in improved efficacy of therapies (e.g., prophylactic or therapeutic agents) in the prevention, management and/or treatment of a viral infection. In some embodiments, a synergistic effect of a combination of therapies (e.g., prophylactic or therapeutic agents) avoids or reduces adverse or unwanted side effects associated with the use of any single therapy.

As used herein, the terms "therapies" and "therapy" can refer to any protocol(s), method(s), compound(s), composition(s), formulation(s), and/or agent(s) that can be used in the prevention, treatment, management, or amelioration of a viral infection or a symptom associated therewith. In certain embodiments, the terms "therapies" and "therapy" refer to biological therapy, supportive therapy, and/or other therapies useful in treatment, management, prevention, or amelioration of a viral infection or a symptom associated therewith known to one of skill in the art. In some embodiments, the term "therapy" refers to a Compound described in Section 5.1. In other embodiments, the term "therapy" refers to a protocol, method, compound composition, formula or agent other than a Compound described in Section 5.1.

As used herein, the terms "treat," "treatment," and "treating" refer in the context of administration of a therapy(ies) to a subject to treat a viral infection to a beneficial or therapeutic effect of a therapy or a combination of therapies. In specific embodiments, such terms refer to one, two, three, four, five or more of the following effects resulting from the administration of a therapy or a combination of therapies: (i) reduce or ameliorate the severity of a viral infection or a symptom associated therewith; (ii) reduce the duration of a viral infection or a symptom associated therewith; (iii) prevent the progression of a viral infection or a symptom associated therewith; (iv) cause regression of a viral infection or a symptom associated therewith; (v) prevent the development or onset of a symptom associated with a viral infection; (vi) reduce the number of symptoms associated with viral infection; (vii) prevent the recurrence of a viral infection or a symptom associated therewith; (viii) reduce or prevent the spread of a virus from one cell to another cell, one tissue to another tissue, or one organ to another organ; (ix) prevent or reduce the spread of a virus from one subject to another subject; (x) reduce organ failure associated with a viral infection; (xi) reduce the incidence of hospitalization; (xii) reduce hospitalization of a subject; (xiii) reduce hospitalization length; (xiv) increase the survival of a subject with a viral infection; (xv) eliminate a virus infection; (xvi) inhibit or reduce virus replication; (xvii) inhibit or reduce the entry of a virus into a host cell(s); (xviii) inhibit or reduce replication of the viral genome; (xix) inhibit or reduce synthesis of viral proteins; (xx) inhibit or reduce assembly of viral particles; (xxi) inhibit or reduce release of viral particles from a host cell(s); (xxii) reduce viral titer; and/or (xxiii) enhance or improve the prophylactic or therapeutic effect(s) of another therapy. In a specific embodiment, the incidence of a disease associated with or caused by a viral infection in a subject is reduced by at least 2.5%, at least 5%, at least 10%, at least 15%, at least 25%, at least 35%, at least 45%, at least 50%, at least 75%, at least 85%, by at least 90%, at least 95%, or at least 99% in a subject administered a Compound relative to a subject or group of subjects (e.g., two, three, five, ten or more subjects) not administered a Compound. In another embodiment, the incidence of a disease associated with or caused by a viral infection in a population (i.e., at least 5, at least 10, or more subjects) receiving a Compound is reduced by at least 2.5%, at least 5%, at least 10%, at least 15%, at least 25%, at least 35%, at least 45%, at least 50%, at least 75%, at least 85%, by at least 90%, at least 95%, or at least 99% in a subject administered a Compound relative to a population not administered the Compound.

Definitions of the more commonly recited chemical groups are set forth below. Certain variables in classes of Compounds disclosed herein recite other chemical groups. Chemical groups recited herein, but not specifically defined, have their ordinary meaning as would be known by a chemist skilled in the art.

An "alkyl" group as used herein is a saturated straight chain or branched non-cyclic hydrocarbon having from 1 to 20 carbon atoms ("$C_{1-20}$ alkyl"), in certain embodiments from 1-10 carbon atoms ("$C_{1-10}$ alkyl"), in certain embodiments from 1-8 carbon atoms ("$C_{1-8}$ alkyl"), in certain embodiments from 1-6 carbon atoms ("$C_{1-6}$ alkyl") and in certain embodiments from 1-4 carbon atoms ("$C_{1-4}$ alkyl"). Representative alkyl groups include, but are not limited to, -methyl, -ethyl, -n-propyl, -n-butyl, -n-pentyl, -n-hexyl, -n-heptyl and -n-octyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. An alkyl group can be substituted or unsubstituted. For example, an alkyl group can be substituted with hydroxy, halogen, carboxy, naphthyl, pyridine, or phenyl, each further optionally substituted with alkyl, hydroxy, trifluoromethyl, alkoxy, nitro or halogen, where appropriate.

An "alkoxy" group as used herein is a —O-alkyl group, wherein an "alkyl" group is as defined above. In certain embodiments, the "alkyl" group has from 1 to 20 carbon atoms ("$C_{1-20}$ alkoxy"), in certain embodiments from 1-10 carbon atoms ("$C_{1-10}$ alkoxy"), in certain embodiments from 1-8 carbon atoms ("$C_{1-8}$ alkoxy"), in certain embodiments from 1-6 carbon atoms ("$C_{1-6}$ alkoxy") and in certain embodiments from 1-4 carbon atoms ("$C_{1-4}$ alkoxy").

An "amino" group as used herein is a —$NH_2$, —NHR or —$NR_2$ group, wherein each R is independently alkyl, alkoxy, amino, cycloalkyl, phenyl, or the R groups taken together with the nitrogen to which they are attached can form a heterocycle, each further optionally substituted with alkyl, hydroxy, trifluoromethyl, alkoxy, nitro or halogen, where appropriate.

A "guanidino" group as used herein is a —N=C(NHR)$_2$ group, wherein R is any appropriate substituent including, but not limited to, H, benzyl, or substituted or unsubstituted alkyl.

The term "halogen" means fluorine, chlorine, bromine and iodine.

A "heterocyclic ring" is a cycloalkyl in which one or more of the ring carbon atoms are independently replaced with a heteroatom from the group consisting of O, S, and N. Representative examples of a heterocyclic ring include, but are not limited to, aziridine, pyrrolidine, piperidine, morpholine, or thiomorpholine. In one embodiment, the heterocyclic ring is a 3 to 10 membered heterocyclic ring. In certain embodiments the heterocyclic ring may encompass a heterocyclic ring that is fused to a 6 membered aromatic ring system, such as a phenyl ring. In one embodiment the heterocyclic ring system is indoline or isoindoline.

In one embodiment, when groups described herein are said to be "substituted," they may be substituted with any suitable substituent or substituents. Illustrative examples of substituents include those found in the exemplary Compounds and embodiments disclosed herein, as well as halogen (chloro, iodo, bromo, or fluoro); $C_{1-6}$ alkyl; $C_{2-6}$ alkenyl; $C_{2-6}$ alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); o-lower alkyl; o-aryl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, See for example, Remington's Pharmaceutical Sciences, 18th eds., Mack Publishing, Easton Pa. (1990) or Remington: The Science and Practice of Pharmacy, 19th eds., Mack Publishing, Easton Pa. (1995).

As used herein and unless otherwise indicated, the term "hydrate" means a Compound, or a salt thereof, that further includes a stoichiometric or non-stoichiometric amount of water bound by non-covalent intermolecular forces.

As used herein and unless otherwise indicated, the term "solvate" means a Compound, or a salt thereof, that further includes a stoichiometric or non-stoichiometric amount of a solvent bound by non-covalent intermolecular forces.

As used herein and unless otherwise indicated, the term "prodrug" means a Compound derivative that can hydrolyze, oxidize, or otherwise react under biological conditions (in vitro or in vivo) to provide Compound. Examples of prodrugs include, but are not limited to, derivatives and metabolites of a Compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of Compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

As used herein and unless otherwise indicated, the term "stereoisomer" or "stereomerically pure" means one stereoisomer of a Compound, in the context of an organic or inorganic molecule, that is substantially free of other stereoisomers of that Compound. For example, a stereomerically pure Compound having one chiral center will be substantially free of the opposite enantiomer of the Compound. A stereomerically pure Compound having two chiral centers will be substantially free of other diastereomers of the Compound. A typical stereomerically pure Compound comprises greater than about 80% by weight of one stereoisomer of the Compound and less than about 20% by weight of other stereoisomers of the Compound, greater than about 90% by weight of one stereoisomer of the Compound and less than about 10% by weight of the other stereoisomers of the Compound, greater than about 95% by weight of one stereoisomer of the Compound and less than about 5% by weight of the other stereoisomers of the Compound, or greater than about 97% by weight of one stereoisomer of the Compound and less than about 3% by weight of the other stereoisomers of the Compound. The Compounds can have chiral centers and can occur as racemates, individual enantiomers or diastereomers, and mixtures thereof. All such isomeric forms are included within the embodiments disclosed herein, including mixtures thereof.

Various Compounds contain one or more chiral centers, and can exist as racemic mixtures of enantiomers, mixtures of diastereomers or enantiomerically or optically pure Compounds. The use of stereomerically pure forms of such Compounds, as well as the use of mixtures of those forms are encompassed by the embodiments disclosed herein. For example, mixtures comprising equal or unequal amounts of the enantiomers of a particular Compound may be used in methods and compositions disclosed herein. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

It should also be noted that Compounds, in the context of organic and inorganic molecules, can include E and Z isomers, or a mixture thereof, and cis and trans isomers or a mixture thereof. In certain embodiments, Compounds are isolated as either the E or Z isomer. In other embodiments, Compounds are a mixture of the E and Z isomers.

4. DESCRIPTION OF THE FIGURES

Figure 1:
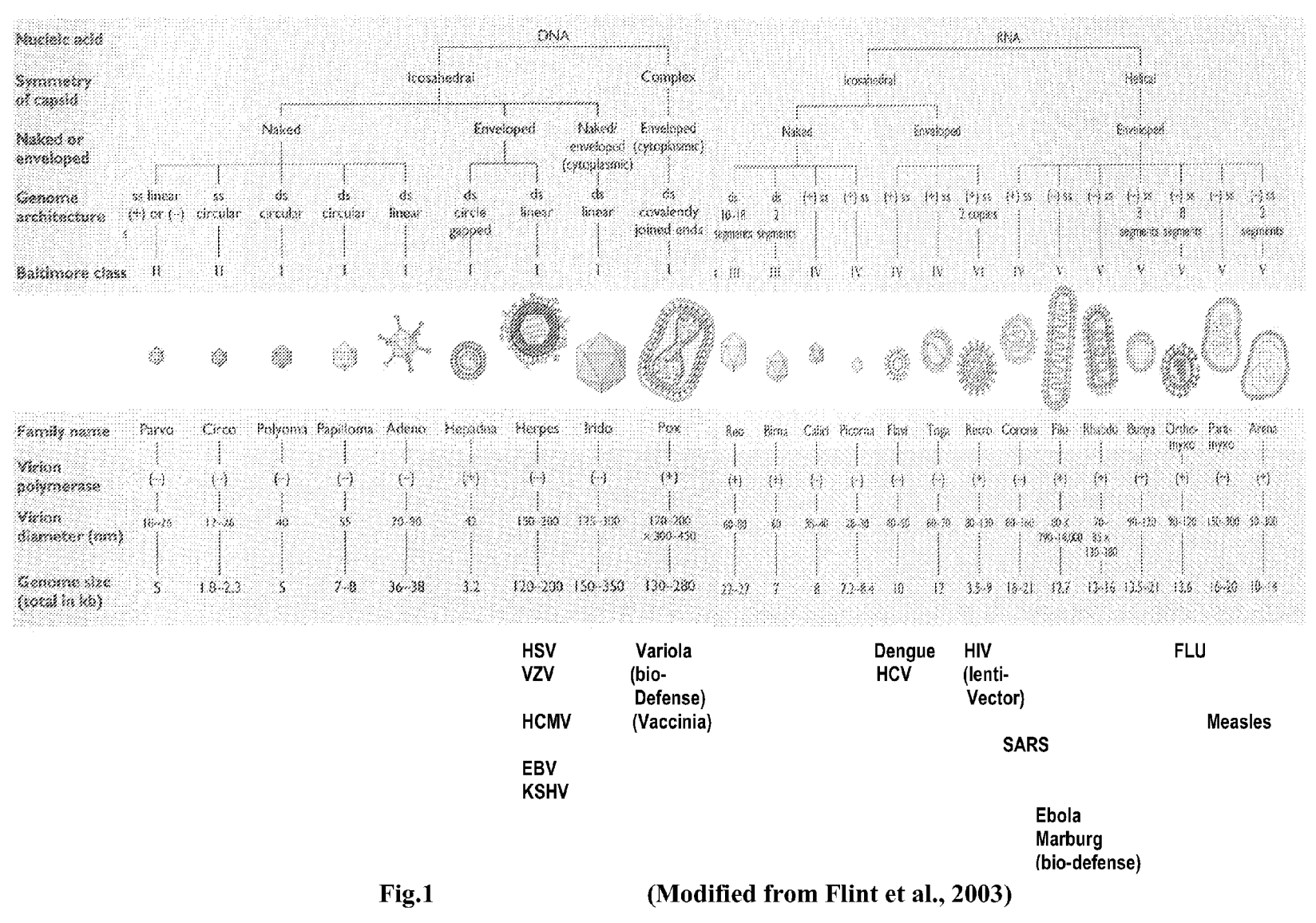

FIG. 1 shows the classification of families of viruses and their structural characteristics. FIG. 1 is a modified figure from Flint et al., Principles of Virology: Molecular Biology, Pathogenesis and Control of Animal Virus. 2nd edition, ASM Press, 2003. A subset of viruses against which Compounds can be assessed for antiviral activity are shown.

FIG. 2. A549 cells were infected with influenza virus WSN (MOI=1) in the presence of A3 (added at the indicated times post infection). Virus growth was measured using a plaque assay at 24 hours post infection. The assay was performed in triplicate and is presented as the mean±standard deviation. hpi=hours post infection.

Figure 3:
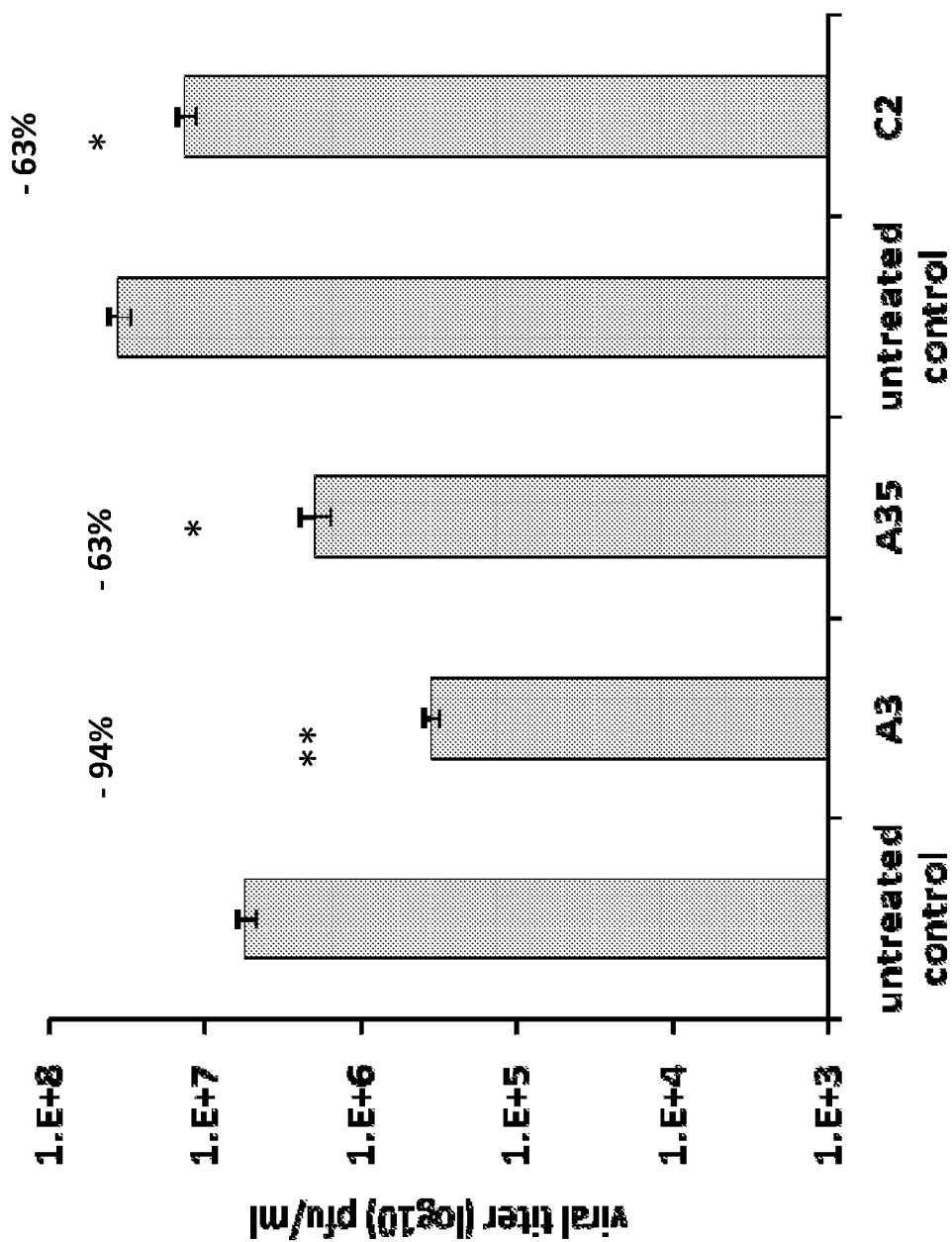

FIG. 3. A549 cells were infected with influenza B/Yamagata/88 virus (MOI=1) in the presence of A3, A35 and C2. Virus growth was measured 24 hours post infection. C2 was tested at a different time and therefore has its own untreated control. The assay was performed in triplicate and is presented as the mean±standard deviation. Student's t test: **, P<0.01; *, P<0.05.

Figure 4:
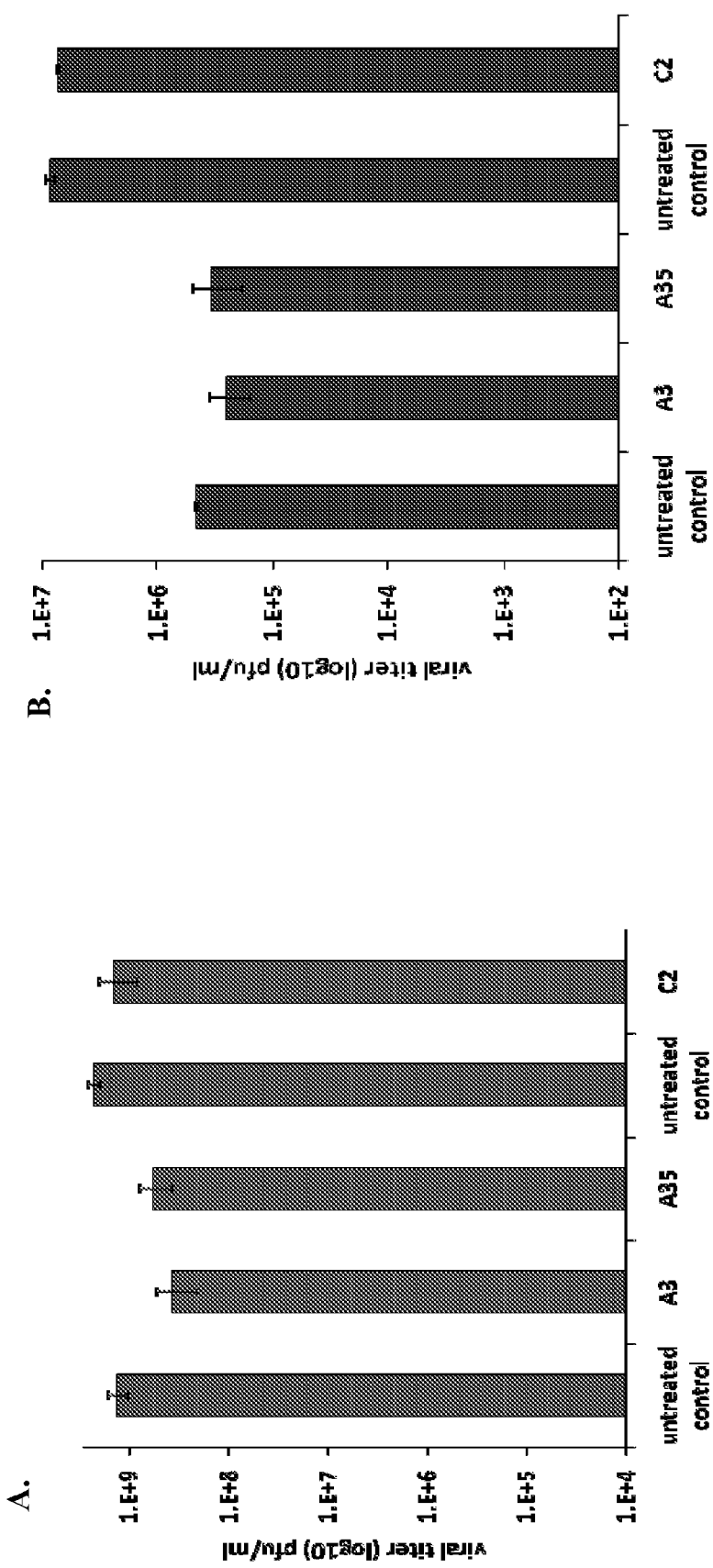

FIG. 4. A549 cells were infected with NDV/B1 (A) and VSV (B) (MOI=1) in the presence of A3, A35 and C2. Virus growth was measured by plaque assay 24 hours post infection. C2 was tested at a different time and therefore has its own untreated control. The assay was performed in triplicate and is presented as the mean±standard deviation.

Figure 5:
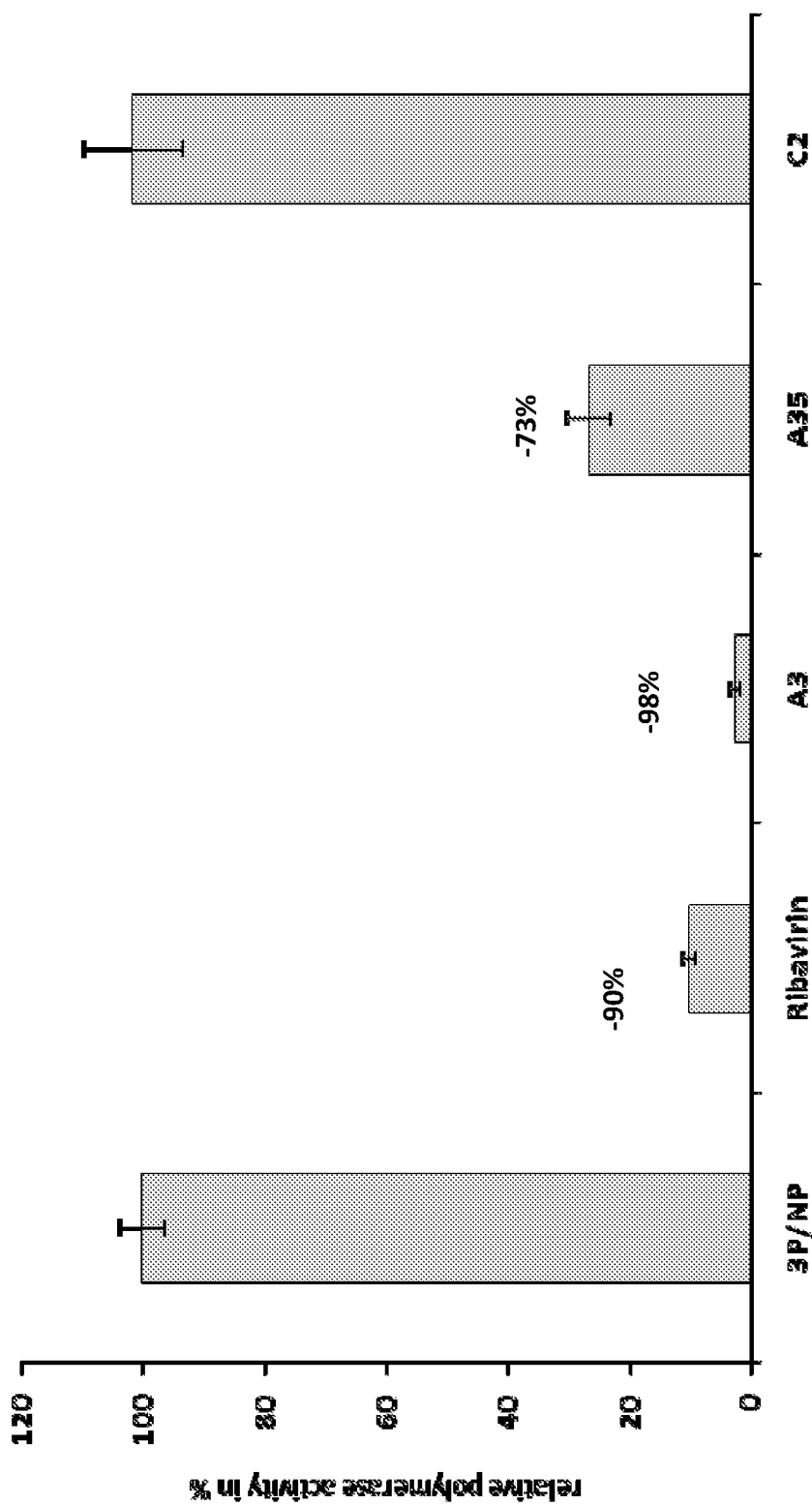

FIG. 5. Mini-genome studies of Compounds A3, A35 and C2. Monolayers of A549 cells were transfected with expression plasmids for influenza virus NP, the 3 polymerase subunits (PB1, PB2, PA), a mini-genome comprising a luciferase reporter gene and an expression plasmid for renilla luciferase for normalization. Cells were pretreated for 4 hours prior to transfection and Compounds were present after the transfection for an additional 20 hours. 3P/NP=control cells transfected with virus expression plasmids without a Compound. Ribavirin, an inhibitor of RNA virus replication, is included as a control. The assay was performed in triplicate and is presented as the mean±standard deviation.

Figure 6:
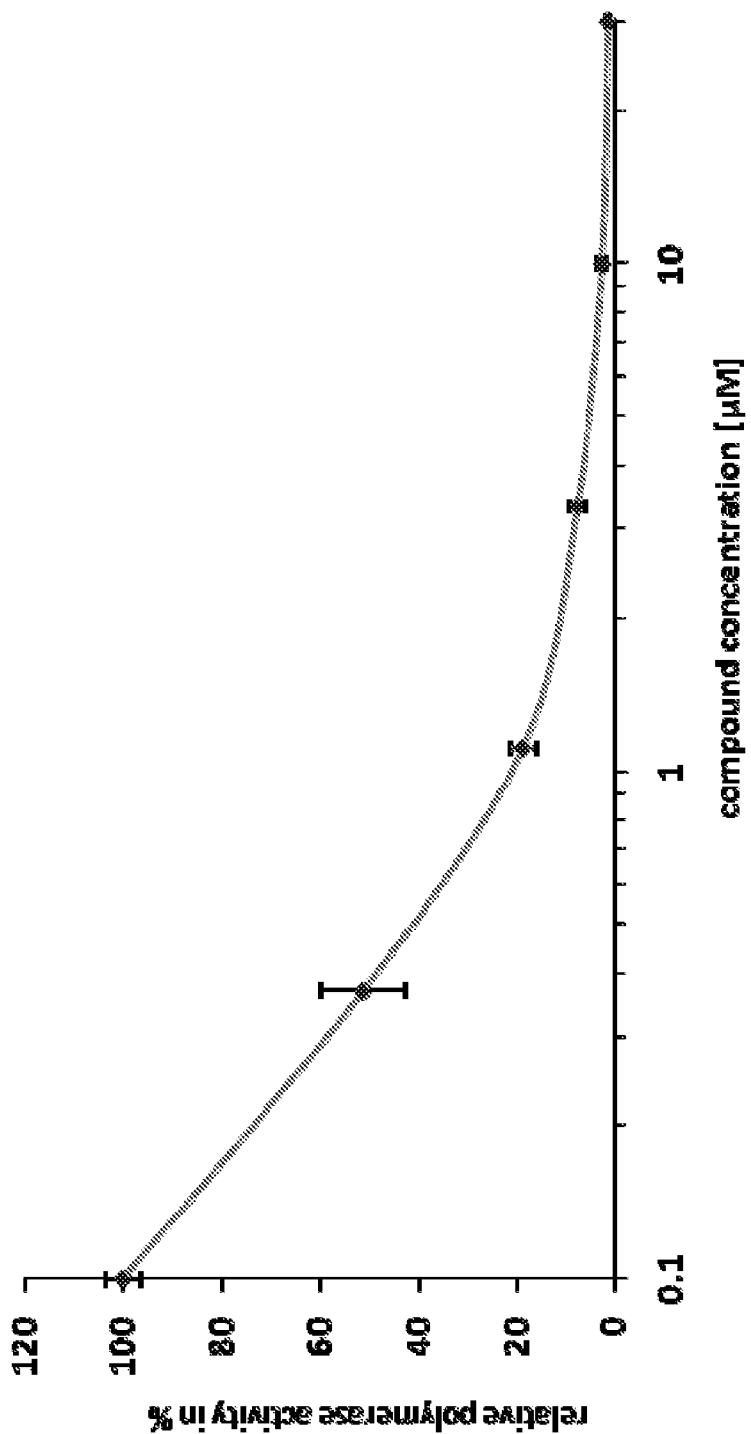

FIG. 6. Influenza virus polymerase activity in response to increasing concentrations of A3. A549 cells were transfected with expression plasmids for influenza virus A/WSN/33 NP and the 3 polymerase subunits (PB1, PB2, PA) and a mini-genome comprising a luciferase reporter gene in the presence of different concentrations of A3 and polymerase activity was measured.

Figure 7:
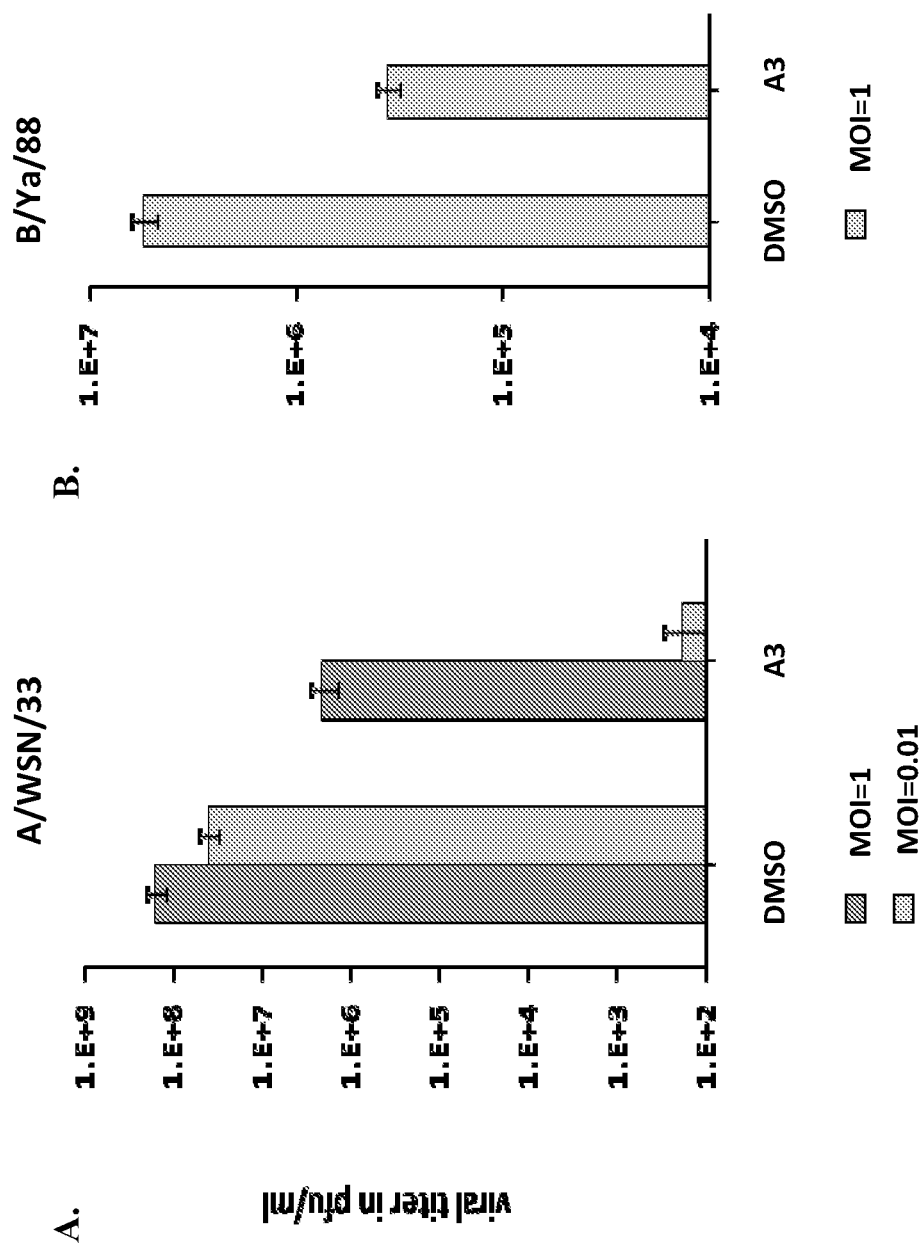

FIGS. 7 A & B. Inhibition of influenza A and B viruses by A3 derivatives. A 549 cells were infected with either (A) A/WSN/33 (MOI=1 or 0.01) or (B) B/Yamagata/88 (MOI=1) in the presence of DMSO (negative control) and A3 derivatives.

Figure 8:
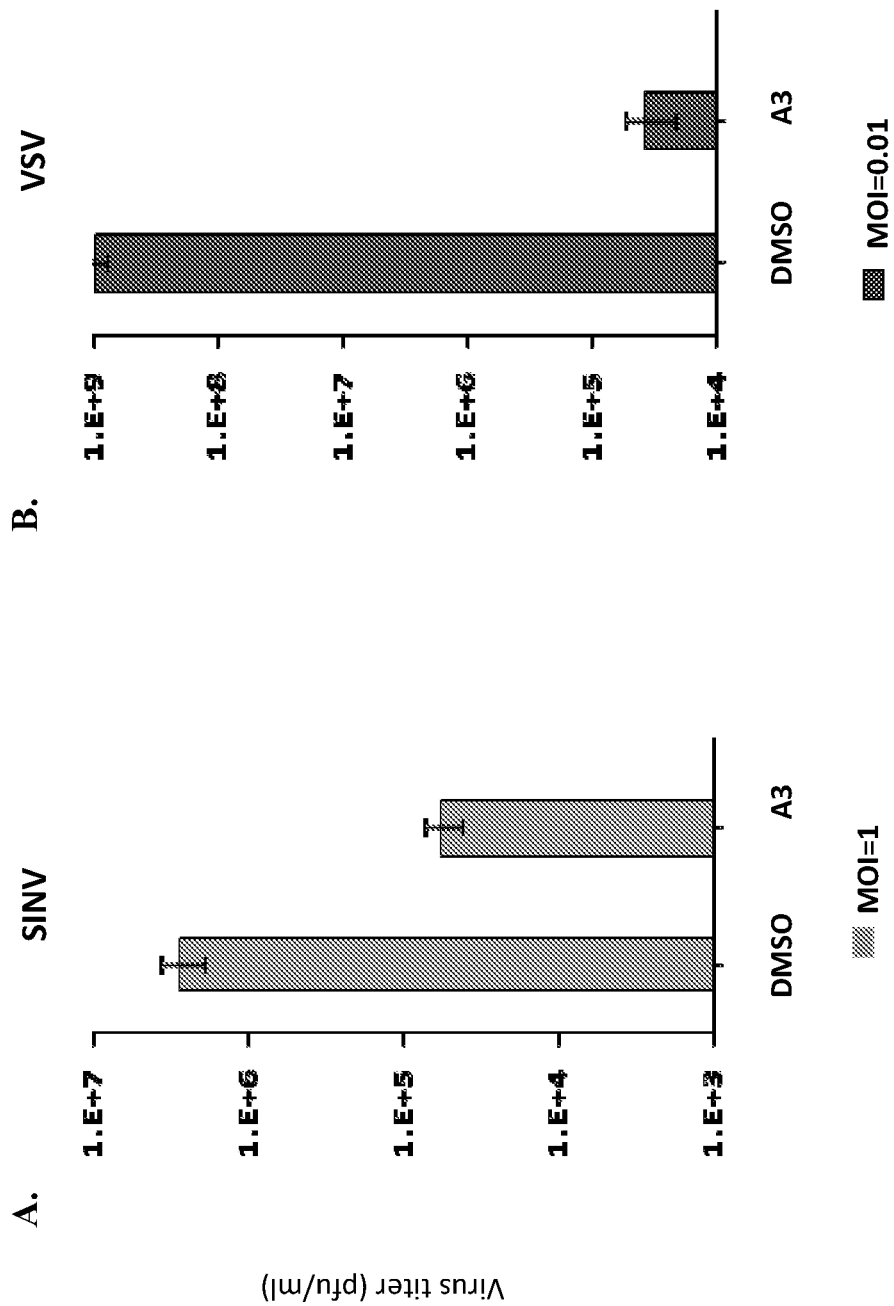

FIGS. 8 A & B. Inhibition of Sindbis virus and Vesicular Stomatitis virus by A3 derivatives. A 549 cells were infected with either (A) Sindbis virus (MOI=1) or (B) Vesicular Stomatitis virus (MOI=0.01), in the presence of DMSO (negative control) and A3 derivatives.

Figure 9:
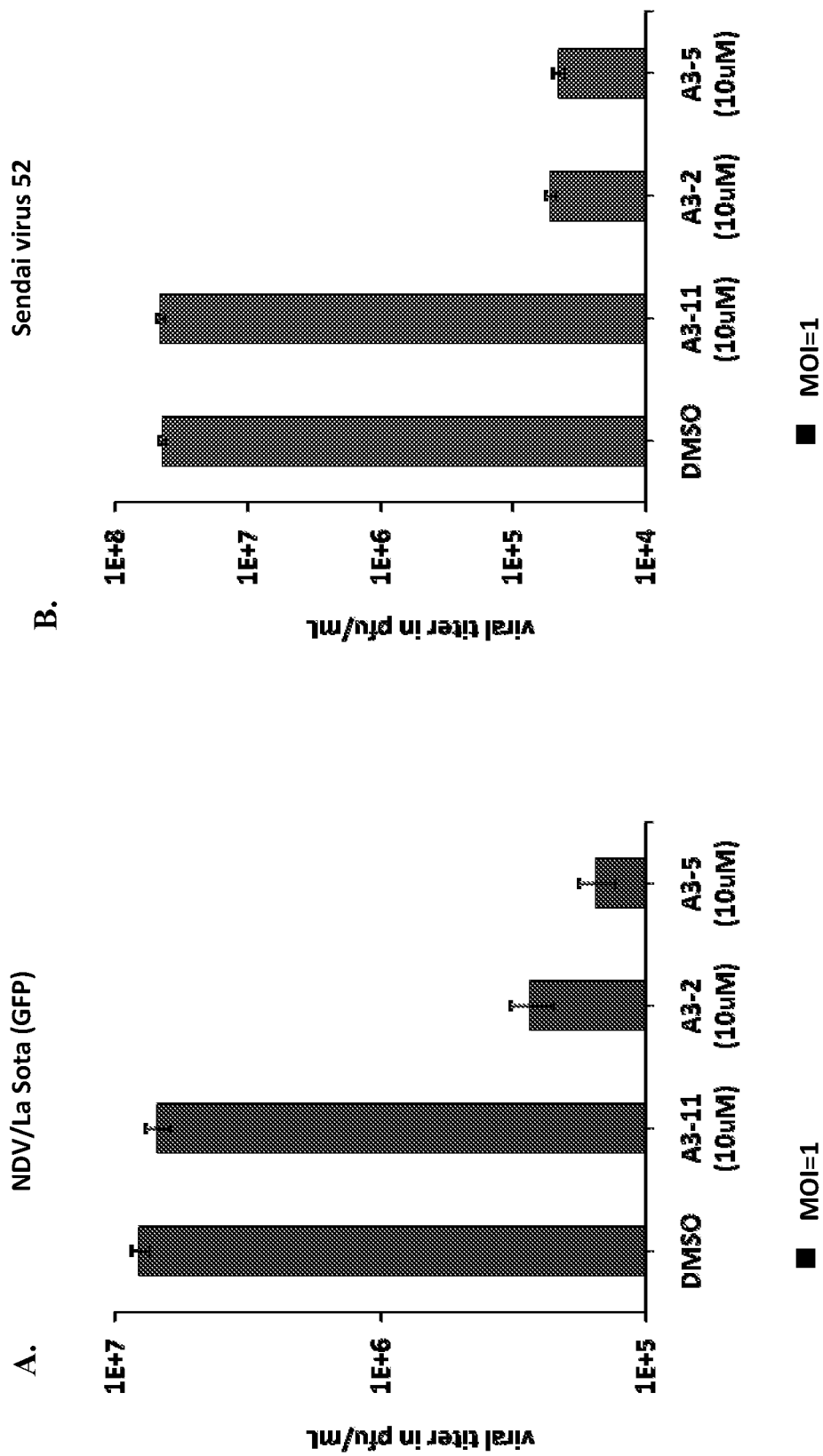

FIGS. 9 A & B. Inhibition of Newcastle disease virus and Sendai virus by A3 derivatives. A 549 cells were infected with either (A) Newcastle disease virus (MOI=1) or (B) Sendai virus (MOI=1), in the presence of DMSO (negative control) and 10 μM of A3 derivatives, A3-11, A3-2, and A3-5. The viral titers were determined by plaque assay performed in Vero cells followed by immuno-staining with specific virus antibodies.

Figure 10:
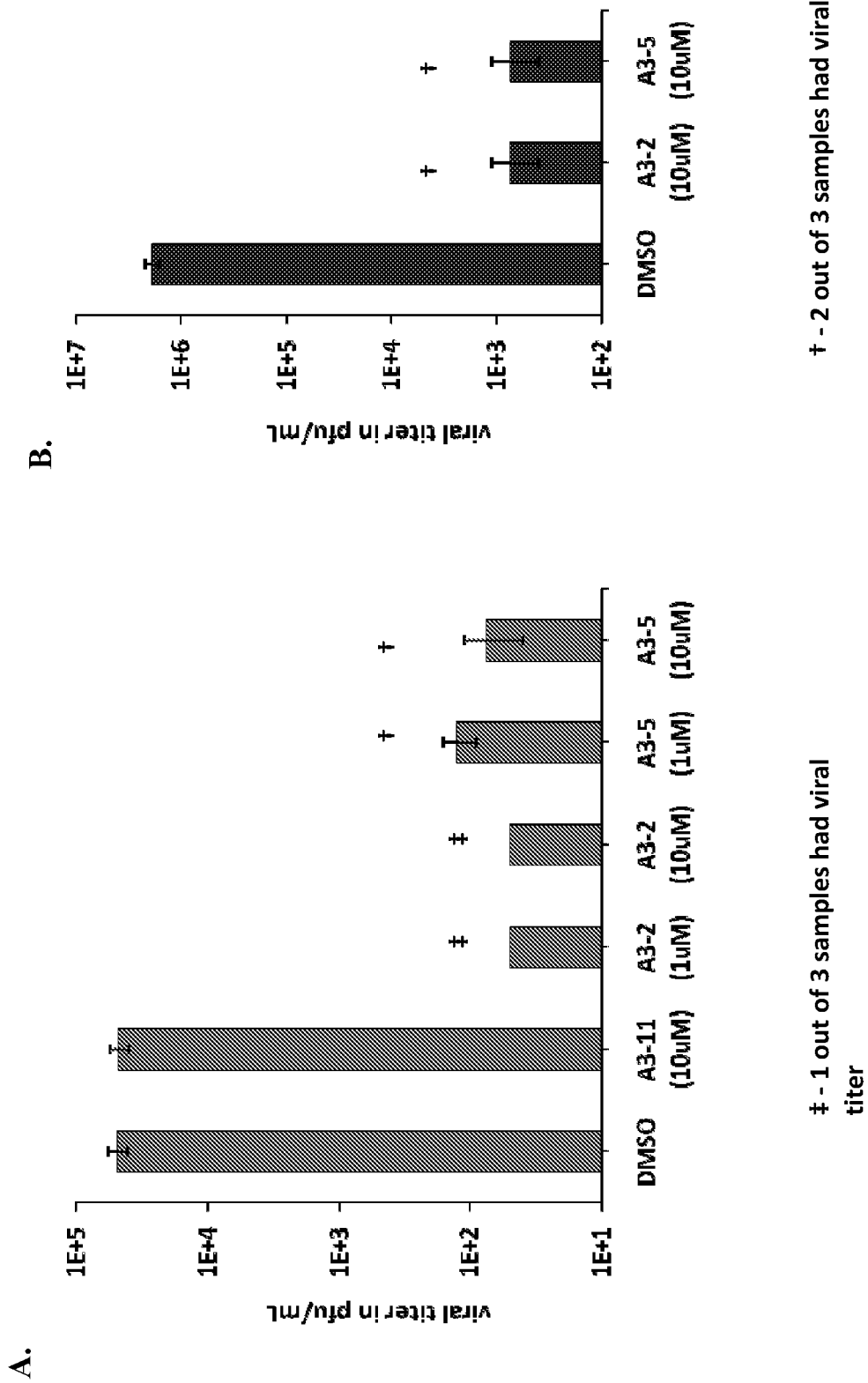

FIGS. 10 A & B. Inhibition of Vaccinia virus and Adenovirus by A3 derivatives. A549 cells were infected with either (A) Vaccinia virus (MOI=1) in the presence of A3-11 (10 μM), A3-2 (1 μM), A3-2 (10 μM), A3-5 (1 μM) and A3-5 (10 μM) or (B) Adenovirus (MOI=1) in the presence of DMSO (negative control) and A3 derivatives, A3-2 (10 μM), and A3-5 (10 μM). The viral titer was determined by plaque assay performed in A549 cells.

Figure 11:
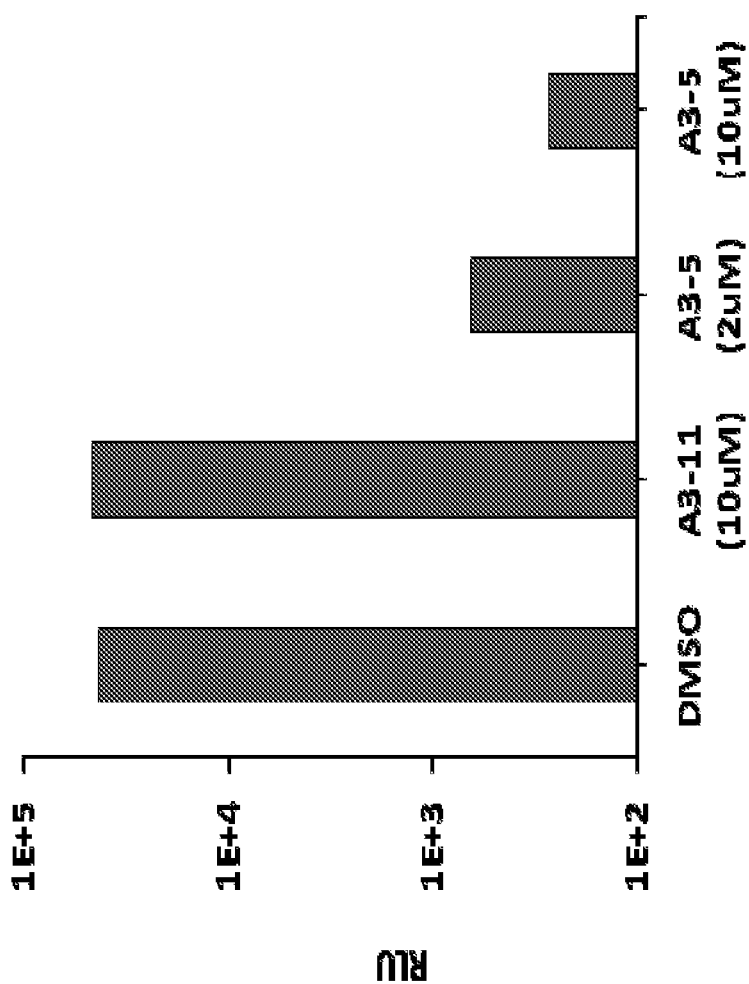

FIG. 11. Inhibition of HIV-by A3 derivatives in TZM-bl cells, 48 Hpi. TZM-bl cells (HeLa cells express the HIV receptors CD4, CXCR4 and CCR5 and a Tat-inducible Beta-galactosidase reporter) were infected with HIV-1 in the presence of DMSO and A3 derivatives, A3-11 (10 μM), A3-5 (2 μM) and A3-5 (10 μM). Beta-galactosidase activity was determined as a reflection of HIV-1 replication.

Figure 12:
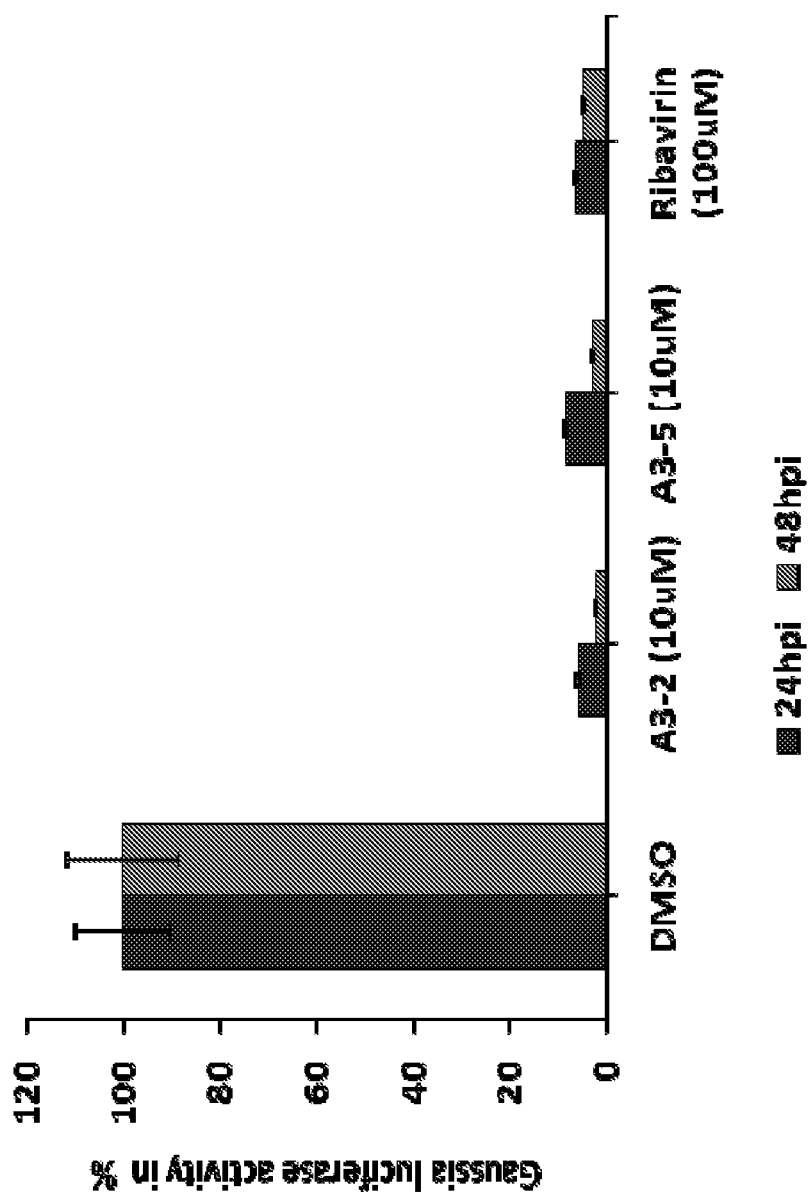

FIG. 12. Inhibition of HCV expressing Gaussia luciferase by A3 derivatives and Ribavirin in Huh 7.5 cells. Huh 7.5 cells were cultured with medium containing A3 derivatives, A3-2 (10 μM), A3-5 (10 μM), ribavirin (100 μM) or the solvent (DMSO) for at least 2 hours prior to infection. Huh 7.5 cells were infected with HCV expressing Gaussia luciferase (strain: HCVcc-JC1). The post-infection medium contained Compounds at the same concentration. Gaussia luciferase activities were determined at 24 and 48 hours post-infection.

Figure 13:
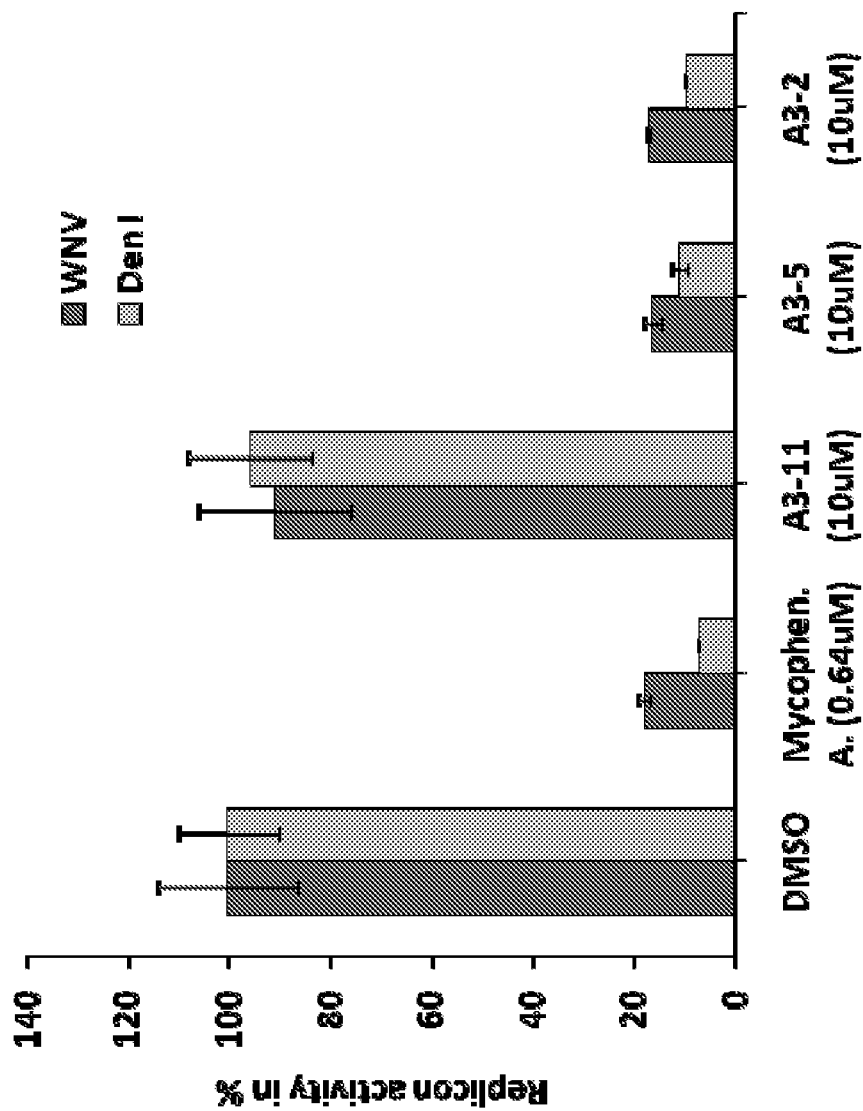

FIG. 13. Inhibition of Vero cells infected with West Nile virus (WNV) and Dengue virus (DenV-1). Vero cells expressing Renilla luciferase under the control of the DenV-1 or the WNV replicon system were cultured for 24 hours in medium containing A3 derivatives, A3-11 (10 μM), A3-5 (10 μM), A3-2 (10 μM), mycophenolic acid (0.64 μM) or the solvent (DMSO). Vero cells were subsequently harvested and Renilla luciferase activity was determined.

Figure 14:
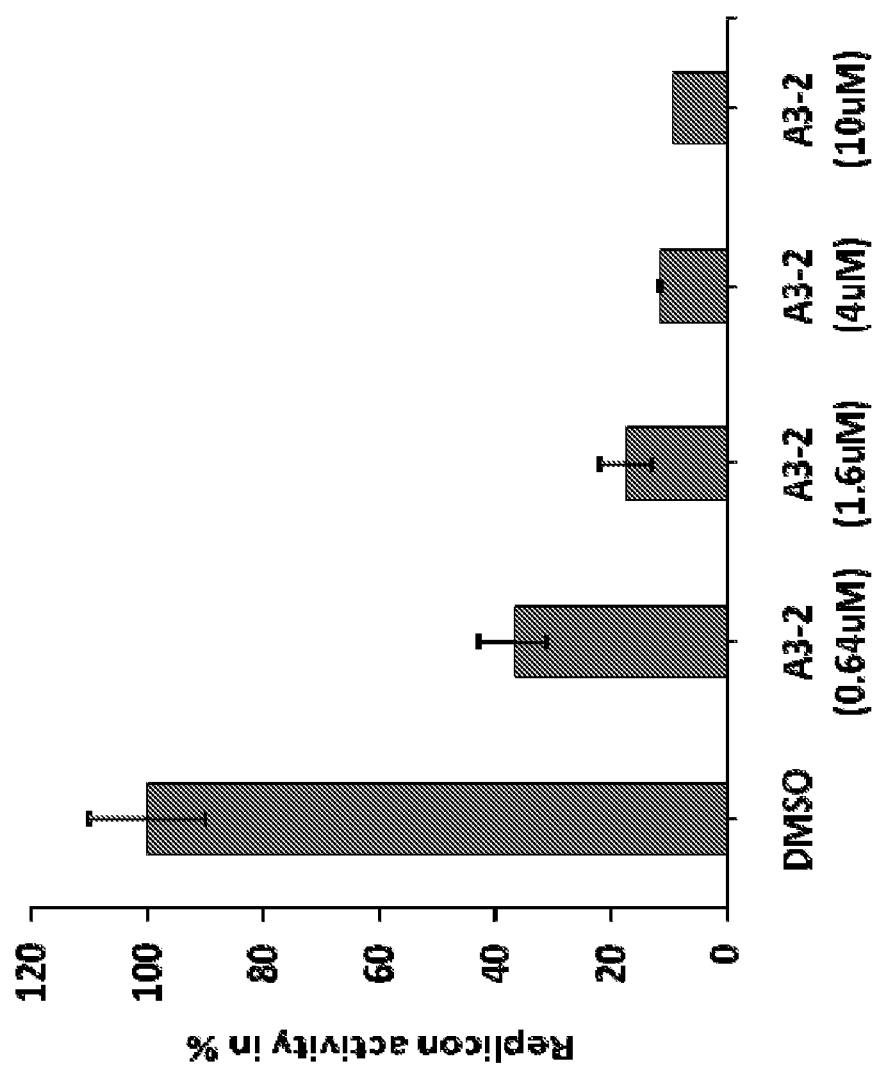

FIG. 14. Dose-responsive inhibition of Dengue virus (DenV-1) replication. Replicon DenV cells were cultured in medium containing A3 derivatives, A3-2 at 0.64 μM, 1.6 μM, 4 μM, 10 μM or the solvent (DMSO). Replicon activity was determined.

Figure 15:
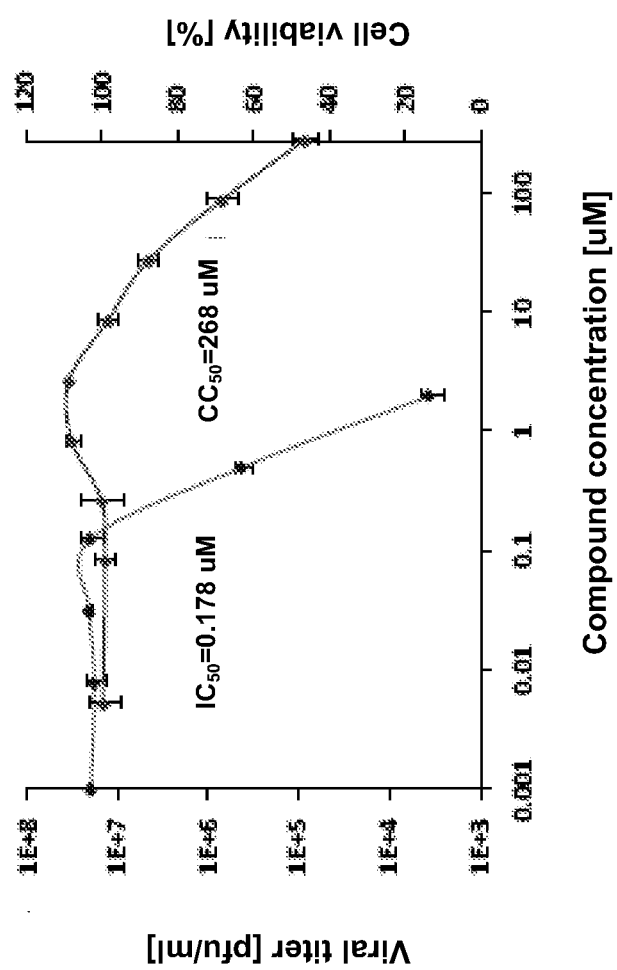

FIG. 15. Compound A3 and its antiviral activity against influenza A/WSN/33 virus. A549 cells were infected with influenza A/WSN/33 virus (MOI=0.01) in the presence of increasing concentrations of compound A3. Viral titers were determined at 24 h postinfection and the $IC_{50}$=0.178 μM (left-hand scale). Mean of three replicates±SD are shown. Cell viability ($CC_{50}$=268 μM) was determined independently for a 24-h incubation period (right-hand scale). Mean of five replicates±SD are shown.

Figure 16:
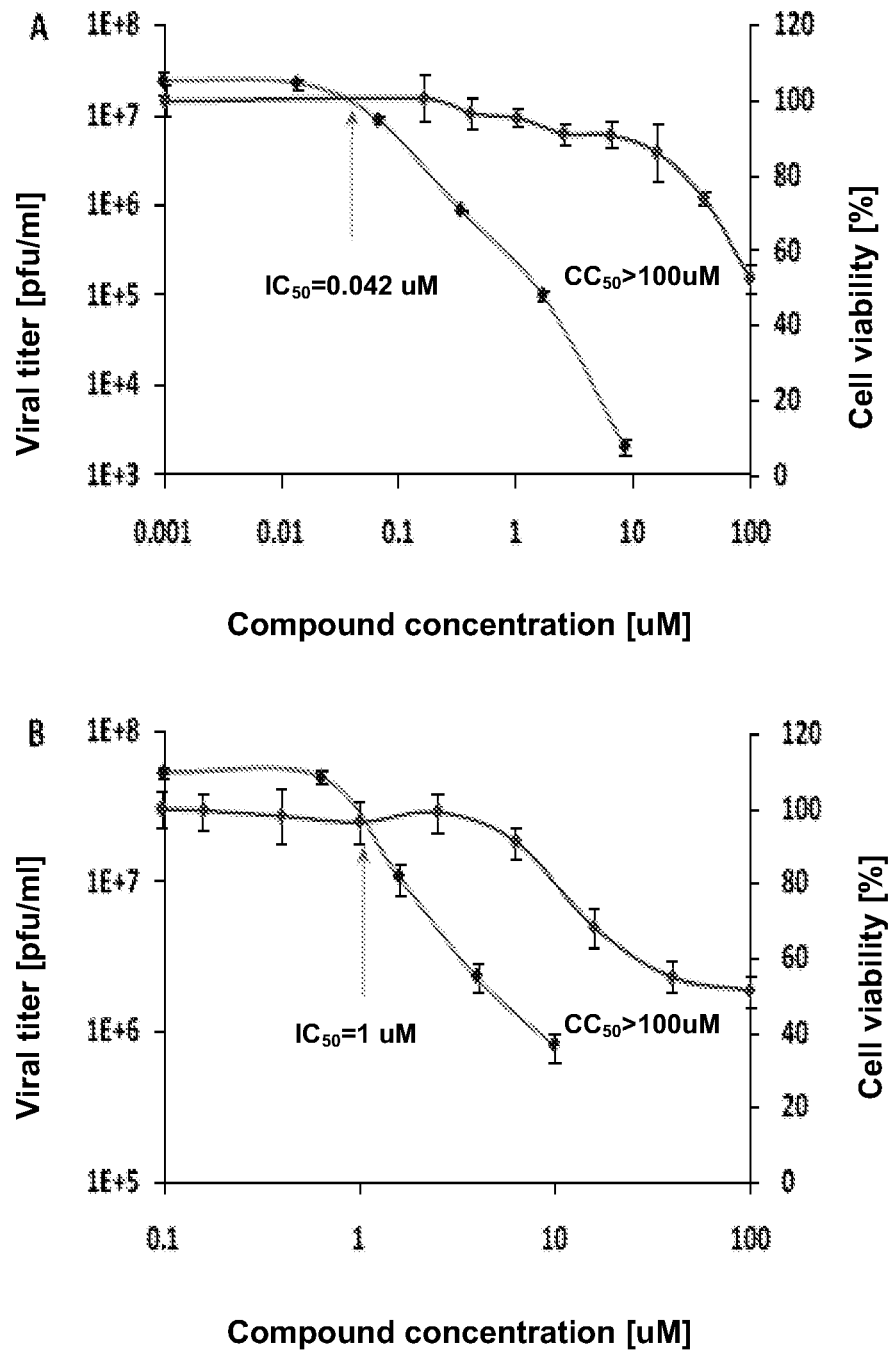

FIGS. 16A and B. Antiviral activity of A3 against influenza A/WSN/33 virus in HTBE and MEF cells. (A) Primary human tracheal bronchial epithelial cells (HTBE). (B) mouse embryo fibroblast cells (MEF) were infected with influenza A/WSN/33 virus (MOI=1) in the presence of increasing concentrations of compound A3 (maximal concentration, $CC_{10}$). Viral titers were determined at 24 h postinfection and $IC_{50}$ calculated (left-hand scale; curve on left). Mean of three replicates±SD are shown. Cell viability ($CC_{50}$) was determined independently for 24-h incubation period (right-hand scale; curve on right). Mean of five replicates±SD are shown.

Figure 17:
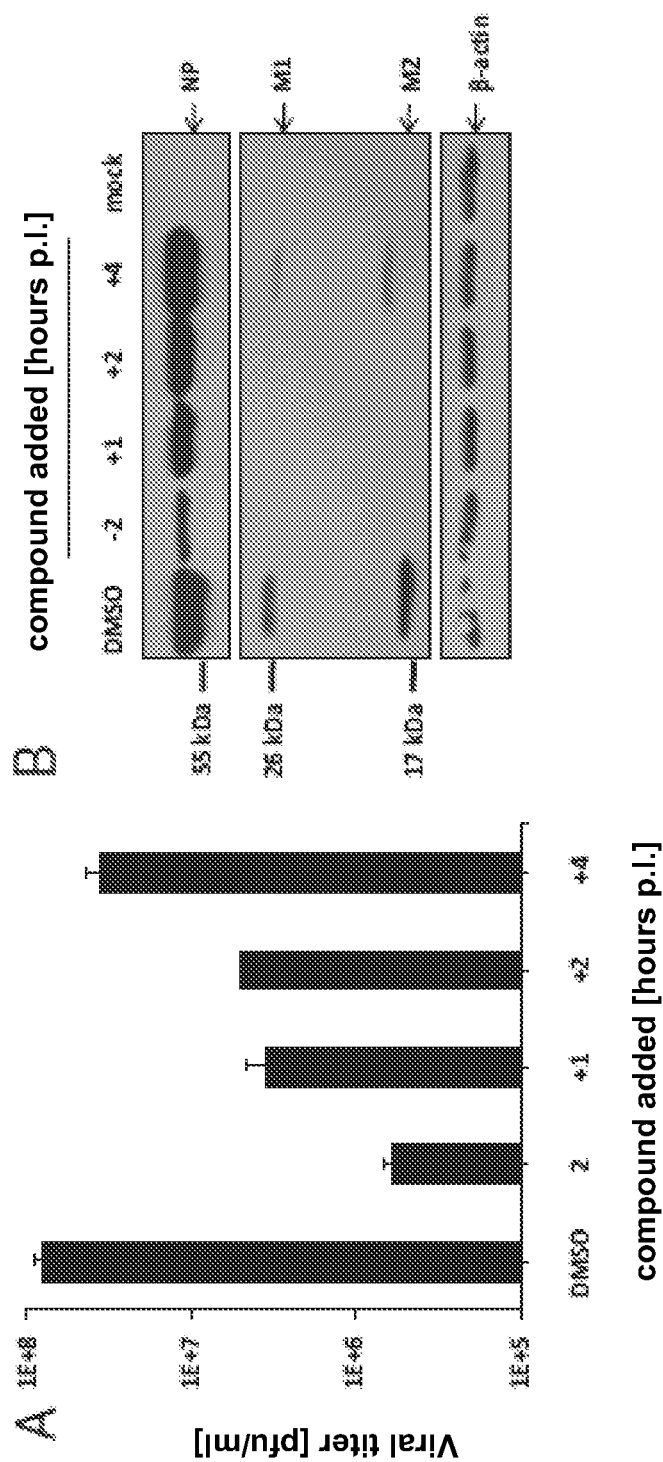

FIGS. 17A & B. Inhibition of influenza A/WSN/33 virus replication by A3 added at different times during the viral life cycle. (A) A549 cells were infected with influenza virus A/WSN/33 (MOI=1). Compound A3 was present in the culture medium 2 h before infection or added to the medium at indicated time points postinfection at its $CC_{10}$. Viral titers were determined 24 h postinfection by plaque assay. Assay was performed in triplicate; results are presented as mean±SD. (B) Viral protein levels (NP, M1, and M2) from infections shown in A were determined by Western blot analysis using specific antibodies.

Figure 18:
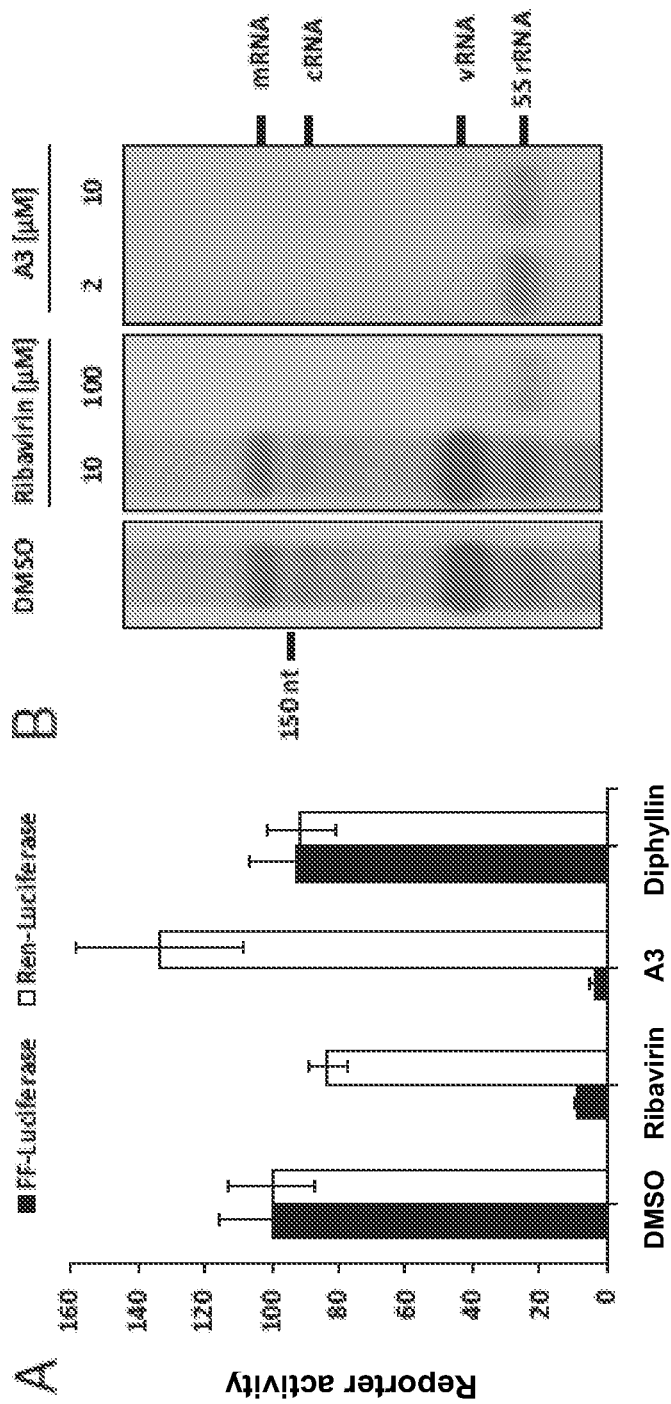

FIGS. 18A & B A3 inhibits influenza viral polymerase activity. (A) A549 cells were transfected with protein expression plasmids for influenza A/WSN/33 virus polymerase subunits PB1, PB2, PA, and nucleoprotein NP. An influenza virus-specific firefly luciferase reporter and a Renilla luciferase expression plasmid were cotransfected. Transfections were performed in the presence of DMSO or A3 at its $CC_{10}$. Ribavirin (replication inhibitor) is included as positive control and diphyllin (entry inhibitor) is included as negative control. Cells were harvested 24 h posttransfection, and activation of the luciferase reporter by the viral polymerase was measured. DMSO control is set to 100%. Assay was performed in triplicate; results are presented as mean±SD. (B) A549 cells were infected with influenza A/PR/8/34 virus at an MOI of 7. Infections were performed in the presence of DMSO, ribavirin, or A3. Viral RNA was extracted 9 h postinfection and subjected to primer extension analysis to determine the levels of v-, c-, and mRNA. Host cell-derived 5S rRNA was used as an internal standard.

Figure 19:
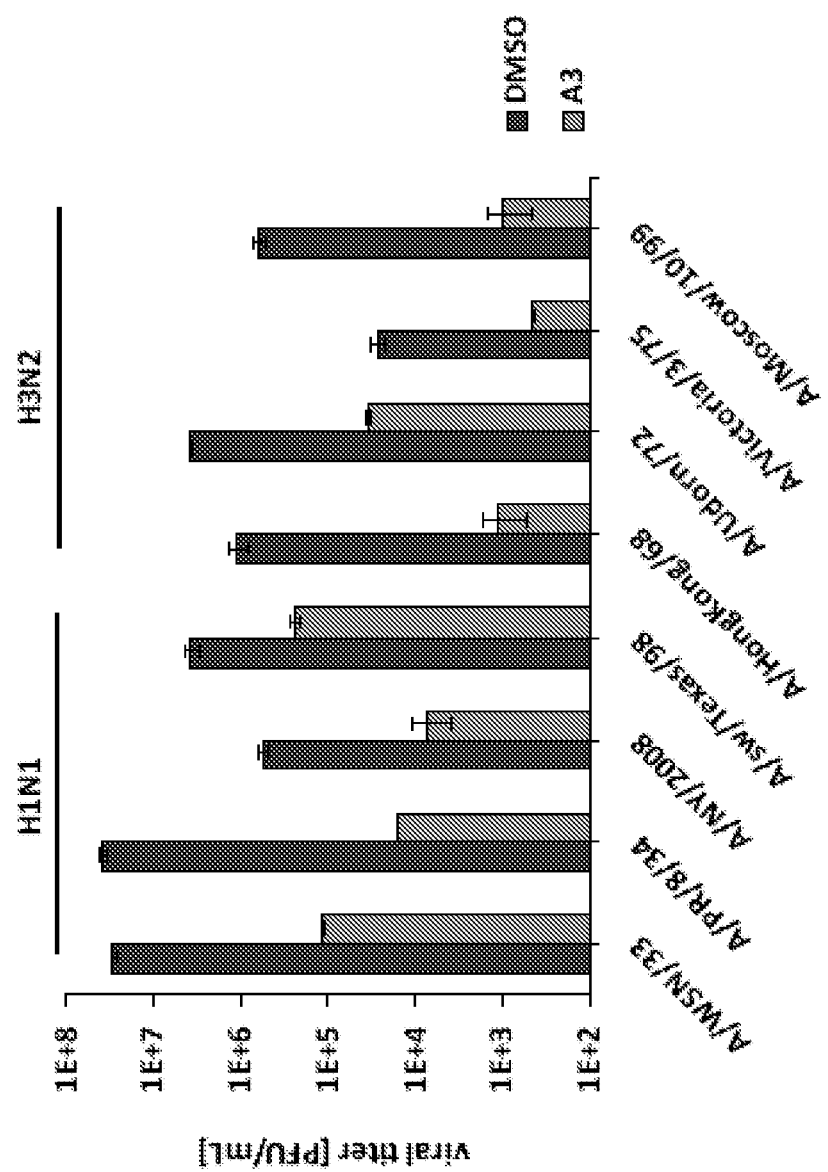

FIG. 19 Inhibition of multiple influenza virus strains by A3. A549 cells were infected at an MOI of 1 with the indicated strains of human and swine (sw) influenza A viruses belonging to H1N1 or H3N2 subtypes (influenza A/NY/2008 is a Tamiflu-resistant isolate). Infections were performed in presence of DMSO or compound A3 (10 μM). Viral titers were determined by plaque assay at 24 h postinfection. Assay was performed in triplicate; results are presented as mean±SD.

Figure 20:
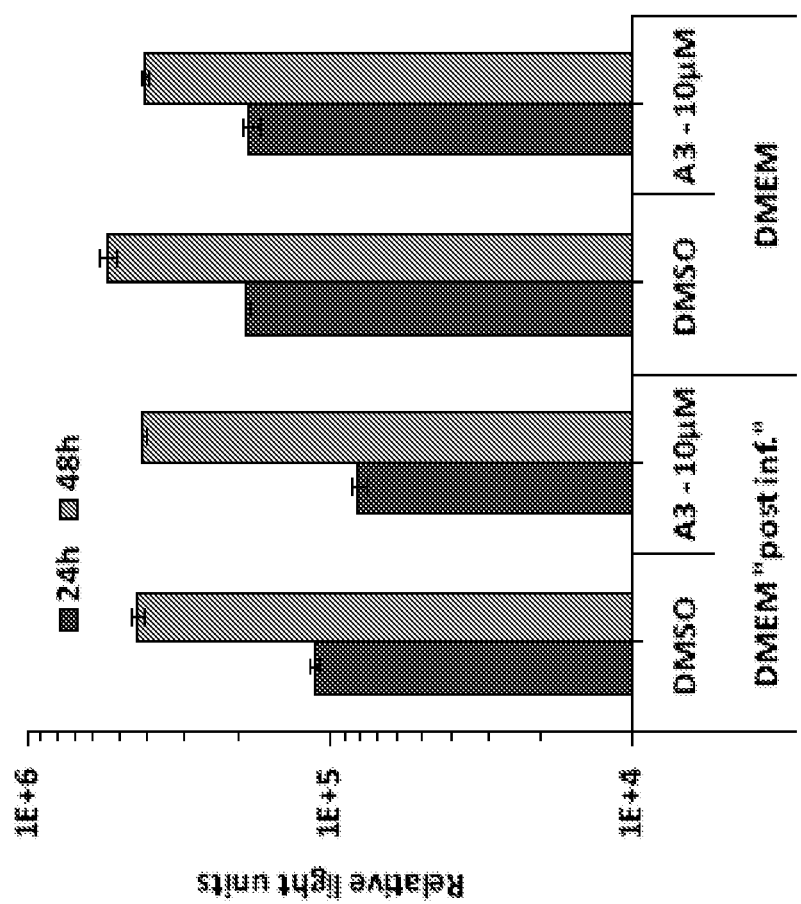

FIG. 20 Viability of A3-treated A549 cells. A549 cells were treated for 24 and 48 h with DMEM "postinfection" medium to reflect infection conditions or regular DMEM cell culture medium containing DMSO (0.05%) or A3 (10 μM). Cell viability was determined using CellTiterGlo Cell Viability Assay (Promega). Mean of 10 replicates±SD are shown.

Figure 21:
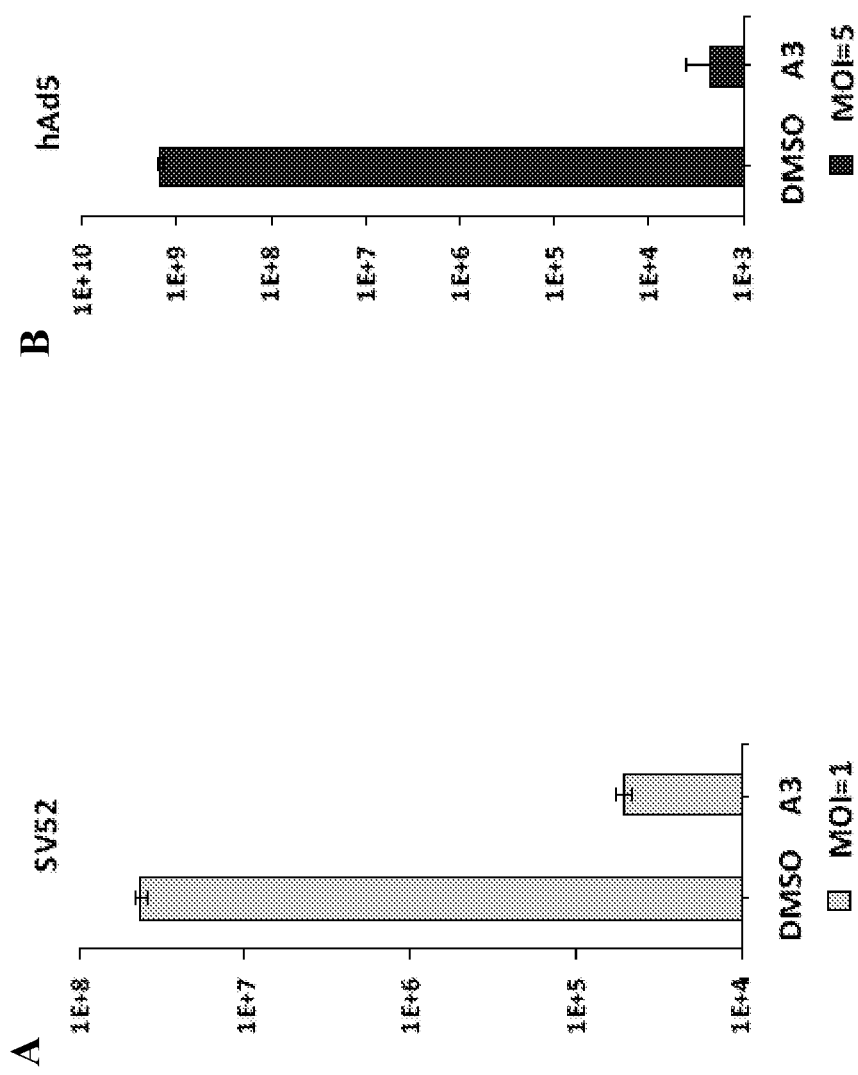
Figure 22:
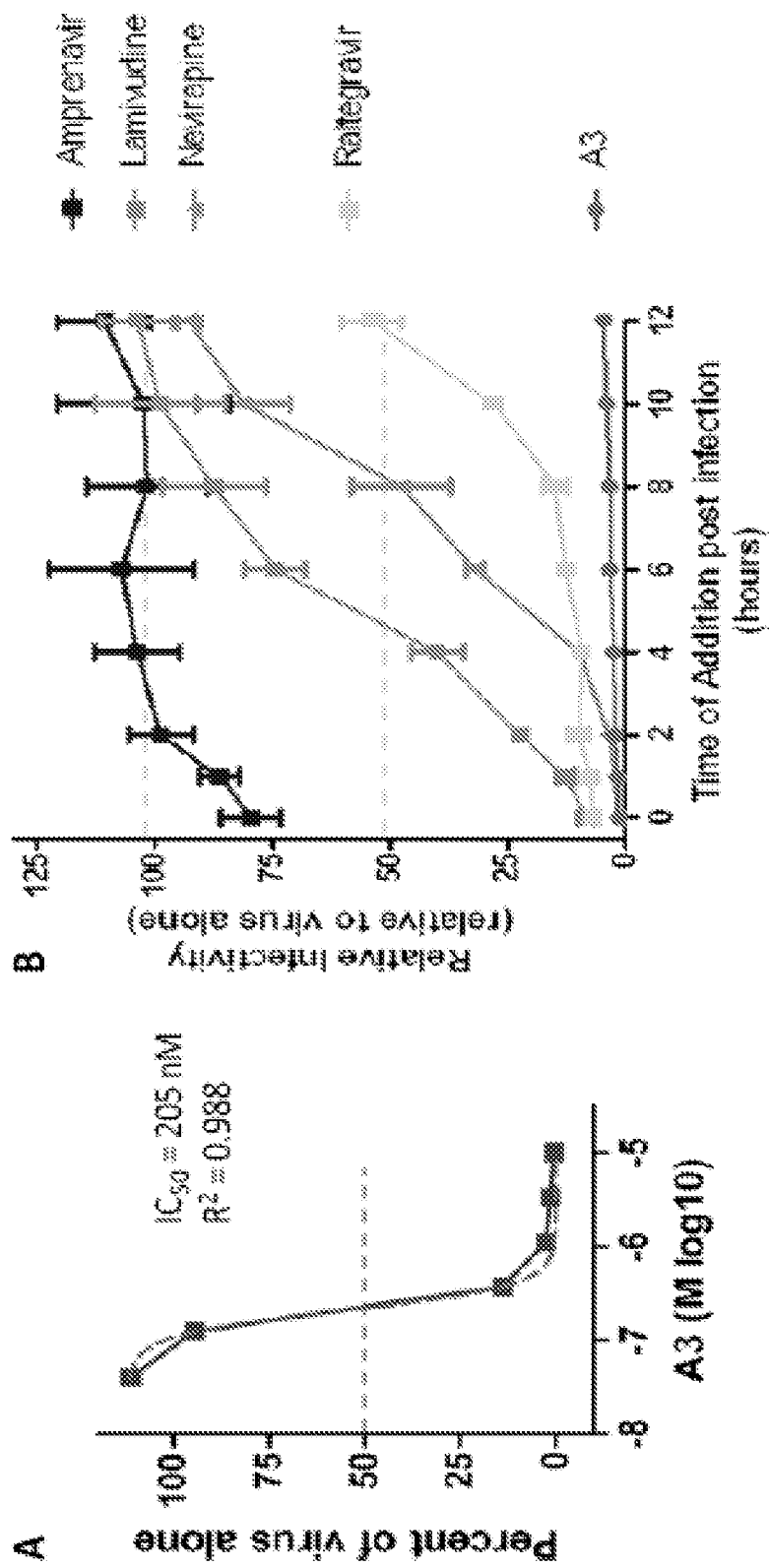

FIGS. 21A&B. Broad-spectrum antiviral activity of A3. A549 cells were infected with (A) Sendai virus 52 (MOI=1) and (B) human adenovirus 5 (MOI=5). Infections were performed in presence of DMSO or compound A3 (10 μM). Viral titers were determined by plaque assay at 24 h postinfection. Assay was performed in triplicate; results are presented as mean±SD FIG. 22 Inhibition of HIV-1 by A3 and comparison with FDA-approved antivirals in a time-of-addition assay. (A) TZM-bl cells were infected with HIV-1 in the presence of increasing concentrations of A3. Viral replication was monitored by β-galactosidase activity and the calculated $IC_{50}$ is shown. Infections were performed in duplicate and repeated independently. Relative light units were normalized to virus-alone control, and means of one representative experiment are shown. (B) TZM-bl cells were infected with HIV-1 (MOI=0.1), and indicated compounds were added at 1- or 2-h intervals postinfection. Lamivudine (10 μM) is a nucleoside analog reverse transcriptase inhibitor; nevirapine (1 μM) is a nonnucleoside reverse transcriptase inhibitor; raltegravir (1 μM) is an integrase inhibitor; and amprenavir (1 μM) is a protease inhibitor. A3 was used at 1 μM. β-Galactosidase activity was determined at 48 h postinfection and is shown as percent infectivity relative to untreated virus. Mean (±SD) results of two independent experiments are shown FIG. 23. The de novo pyrimidine synthesis pathway FIGS. 24A-E. Inhibition of influenza virus replication by A3 is reversed by excess uracil and orotate. (A) Plaque-reduction assay with influenza A/WSN/33 virus was performed in A549 (human) and MDCK (canine) cells in the presence of DMSO, 10 μM A3 alone, or A3 and indicated purine and pyrimidine bases (10-fold excess relative to A3). Percent replication was calculated and set relative to DMSO control. (B and D) A549 (human) cells and (C and E) MDCK (canine) cells were infected with influenza A/WSN/33 virus (MOI=0.001). (B and C) Cell culture medium was supplemented with A3 (5 μM) and in addition with increasing concentrations of uracil (Ura), as indicated by fold excess relative to A3. (D and E) Cell culture medium was supplemented with A3 (10 μM) and in addition with increasing concentrations (fold excess relative to A3) of dihydroorotate (DHO) or orotate (Oro). Viral titers were determined by standard plaque assay at indicated time points.

Figure 25:
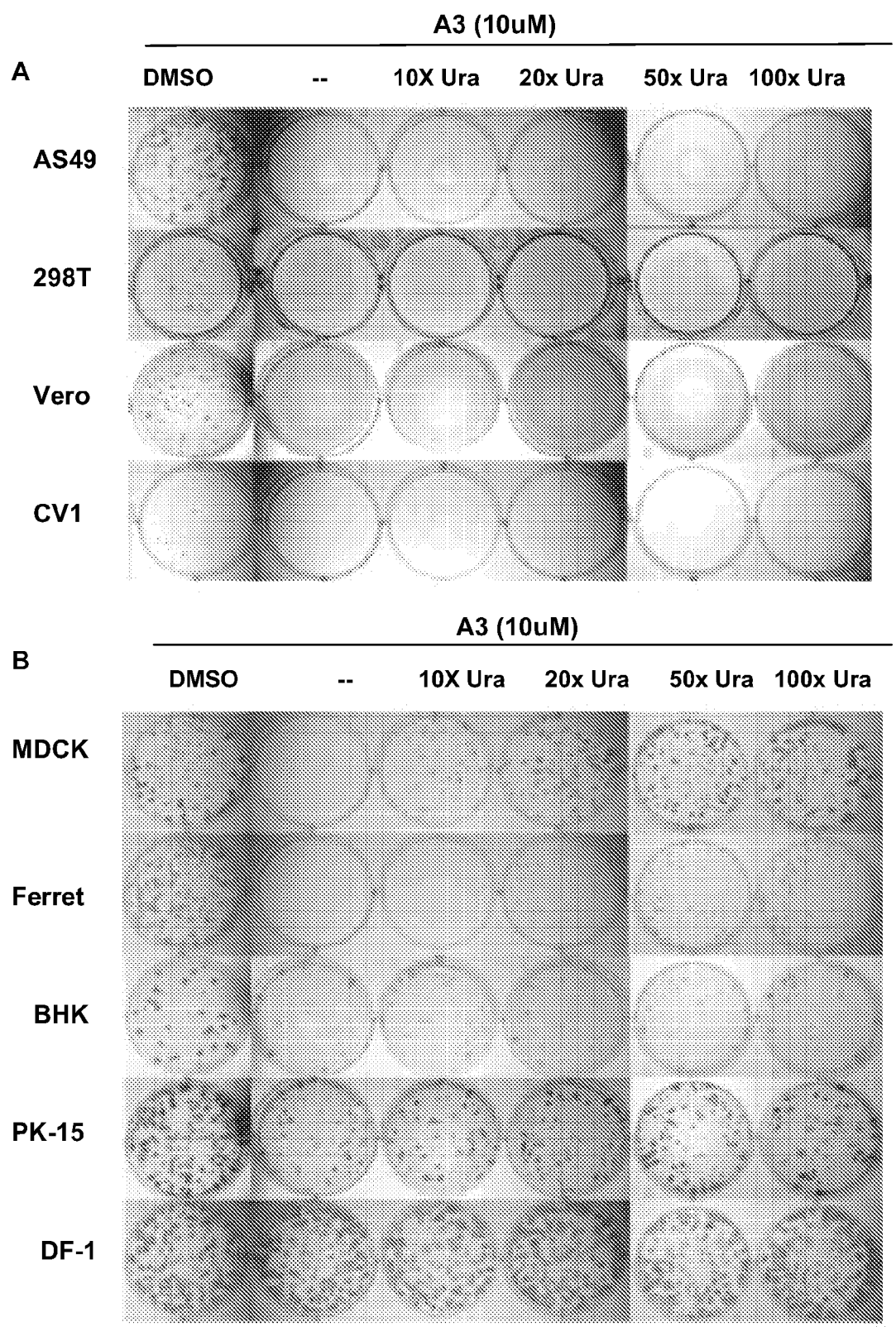

FIG. 25 Inhibition of influenza virus replication by A3 and restoration by uracil in different cell lines. Plaque-reduction assays with influenza A/WSN/33 virus were performed in (A) human/primate cell lines and (B) nonhuman/nonprimate cell lines. Overlay medium contained DMSO (0.05%) or A3 (10 μM) with increasing uracil concentrations. Viral plaques were fixed 24 h postinfection and visualized by standard immunostaining.

Figure 26:
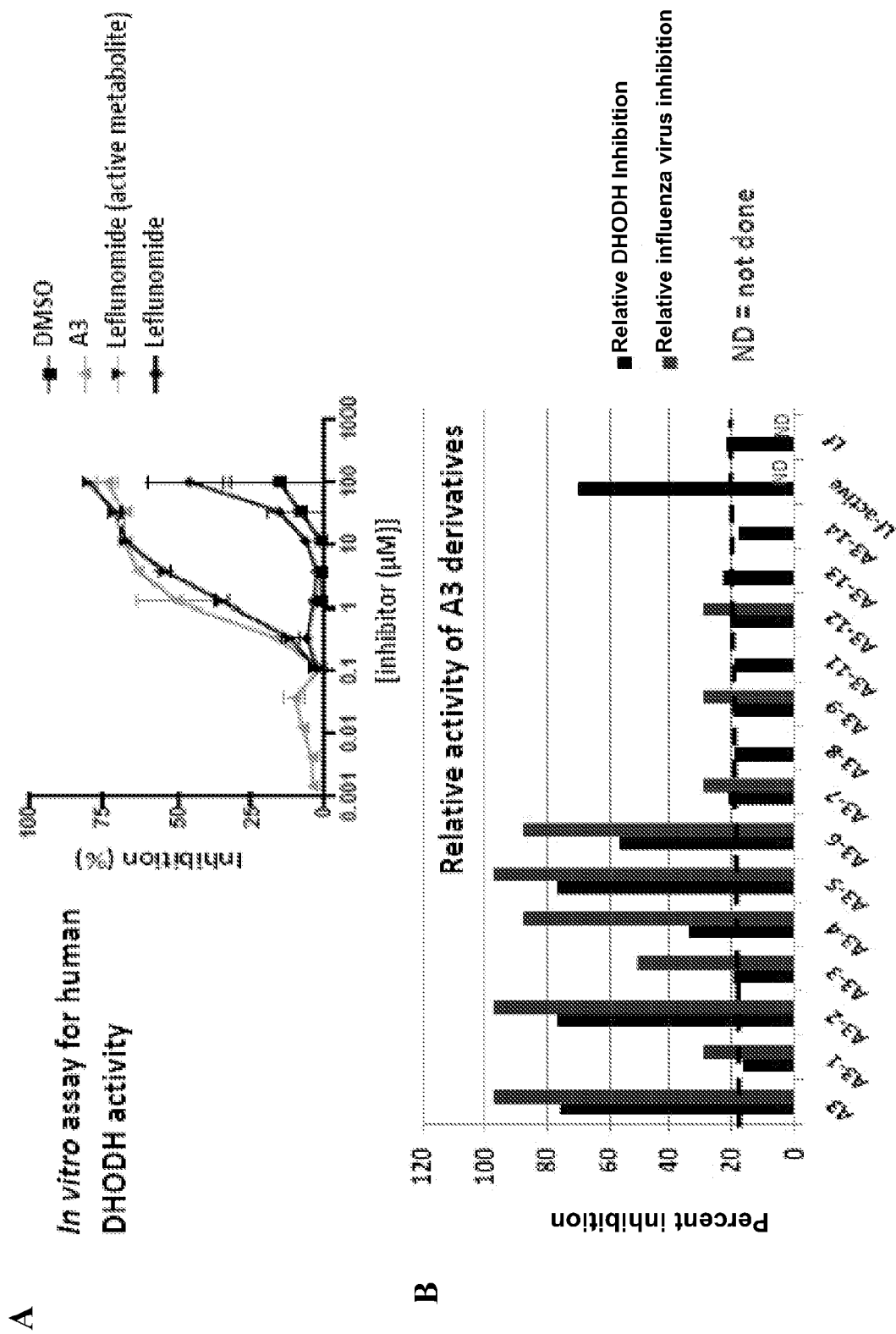

FIGS. 26A&B A3 inhibits DHODH activity in vitro. (A) In vitro assay for human DHODH activity. (B) Relative DHODH inhibition and relative influenza virus inhibition of A3 and its derivatives.

5. DETAILED DESCRIPTION

5.1 Compounds

In certain embodiments, provided herein are Compounds of formula A3-H:

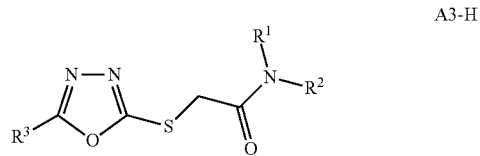

A3-H and pharmaceutically acceptable salts, hydrates, solvates, prodrugs and stereoisomers thereof, wherein:

$R^1$ and $R^2$ are at each occurrence independently a $C_1$-$C_8$ alkyl group; or $R^1$ and $R^2$, together with the nitrogen atom $R^1$ and $R^2$ are bound to, form a 3 to 10 membered heterocyclic ring; and $R^3$ is substituted or unsubstituted indole, substituted or unsubstituted phenyl, substituted or unsubstituted benzofuran, or substituted or unsubstituted pyridine.

In one embodiment, $R^1$ and $R^2$, together with the nitrogen atom $R^1$ and $R^2$ are bound to, form a 3 to 8 membered heterocyclic ring.

In another embodiment, $R^1$ and $R^2$, together with the nitrogen atom $R^1$ and $R^2$ are bound to, form unsubstituted pyrrolidone, unsubstituted isoindoline, unsubstituted morpholine or unsubstituted azepane.

In another embodiment, $R^1$ and $R^2$ are each independently a $C_1$-$C_8$ alkyl group, such as ethyl or isopropyl.

In another embodiment, $R^3$ is unsubstituted indole

In another embodiment, $R^3$ is substituted indole.

In another embodiment, $R^3$ is indole substituted with one or more $C_1$-$C_8$ alkyl groups, such as methyl groups.

In another embodiment, $R^3$ is substituted phenyl.

In another embodiment, $R^3$ is phenyl substituted with one or more sulfonamide groups or one or more $C_1$-$C_8$ alkoxy groups.

In another embodiment, $R^3$ is unsubstituted benzofuran.

In another embodiment, $R^3$ is unsubstituted pyridine.

In one embodiment, Compounds of formula A3-H do not include Compounds wherein $R^1$ and $R^2$, together with the nitrogen atom $R^1$ and $R^2$ are bound to, form piperidine, for example, unsubstituted piperidine.

In another embodiment, Compounds of formula A3-H do not include Compounds wherein $R^3$ is phenyl substituted with hydroxyl, for example, o-hydroxyphenyl or 2-hydroxyphenyl.

In another embodiment, Compounds of formula A3-H do not include Compounds wherein $R^1$ and $R^2$, together with the nitrogen atom $R^1$ and $R^2$ are bound to, form piperidine, for example, unsubstituted piperidine, and $R^3$ is phenyl substituted with hydroxyl, for example, o-hydroxyphenyl or 2-hydroxyphenyl.

In another embodiment, Compounds of formula A3-H do not include Compounds wherein $R^1$ and $R^2$, together with the nitrogen atom $R^1$ and $R^2$ are bound to, form unsubstituted morpholine.

In another embodiment, Compounds of formula A3-H do not include Compounds wherein $R^1$ and $R^2$, together with the nitrogen atom $R^1$ and $R^2$ are bound to, form unsubstituted piperidine or unsubstituted morpholine, and $R^3$ is unsubstituted pyridine.

In another embodiment, Compounds of formula A3-H do not include Compounds wherein $R^1$ and $R^2$, together with the nitrogen atom $R^1$ and $R^2$ are bound to, form pyrrolidine.

In another embodiment, Compounds of formula A3-H do not include Compounds wherein $R^1$ and $R^2$, together with the nitrogen atom $R^1$ and $R^2$ are bound to, form pyrrolidine, and $R^3$ is substituted phenyl, such as methoxy substituted phenyl.

In another embodiment, Compounds of formula A3-H do not include Compounds wherein $R^1$ and $R^2$, together with the nitrogen atom $R^1$ and $R^2$ are bound to, form pyrrolidine, and $R^3$ is unsubstituted pyridine.

In another embodiment, Compounds of formula A3-H do not include Compounds of the formula:

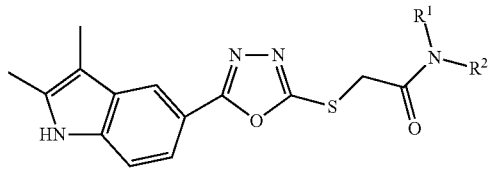

and pharmaceutically acceptable salts, hydrates, solvates, prodrugs and stereoisomers thereof, wherein:

$R^1$ and $R^2$ are at each occurrence independently a $C_1$-$C_8$ alkyl group; or $R^1$ and $R^2$, together with the nitrogen atom $R^1$ and $R^2$ are bound to, form a 3 to 8 membered heterocyclic ring.

In another embodiment, with respect to uses relating to or associated with a negative-sense, single-stranded RNA virus infection, such as inhibiting its replication or preventing, treating or managing a disease associated therewith (e.g., influenza), Compounds of formula A3-H do not include Compounds of the formula:

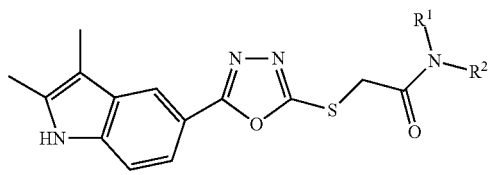

and pharmaceutically acceptable salts, hydrates, solvates, prodrugs and stereoisomers thereof, wherein:

$R^1$ and $R^2$ are at each occurrence independently a $C_1$-$C_8$ alkyl group; or $R^1$ and $R^2$, together with the nitrogen atom $R^1$ and $R^2$ are bound to, form a 3 to 8 membered heterocyclic ring.

In another embodiment, Compounds of formula A3-H do not include 2-[5-(2-hydroxy-phenyl)-[1,3,4]oxadiazol-2-yl-sulfanyl]-1-piperidin-1-yl-ethanone, having the structure:

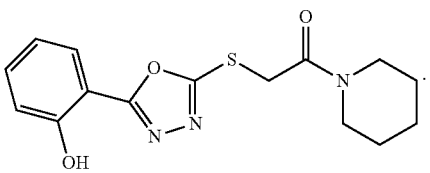 [SMILES: O=C(CSc1nnc(-c2ccccc2O)o1)N1CCCCC1]

In another embodiment, Compounds of formula A3-H do not include 1-morpholino-2-(5-(pyridin-4-yl)-1,3,4-oxadiazol-2-ylthio)ethanone, having the structure:

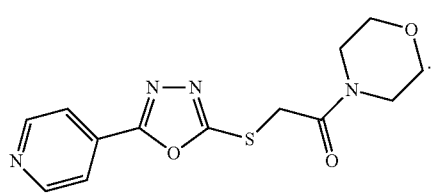 [SMILES: O=C(CSc1nnc(-c2ccncc2)o1)N1CCOCC1]

In another embodiment, Compounds of formula A3-H do not include 1-(piperidin-1-yl)-2-(5-(pyridin-4-yl)-1,3,4-oxadiazol-2-ylthio)ethanone, having the structure:

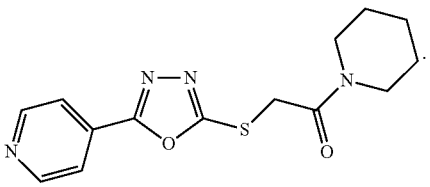 [SMILES: O=C(CSc1nnc(-c2ccncc2)o1)N1CCCCC1]

In another embodiment, Compounds of formula A3-H do not include 24544-methoxyphenyl)-1,3,4-oxadiazol-2-ylthio)-1-(pyrrolidin-1-yl)ethanone, having the structure:

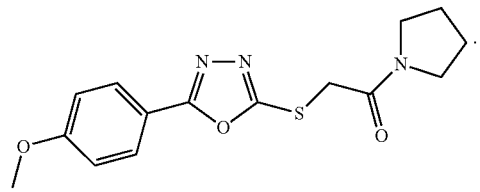 [SMILES: COc1ccc(-c2nnc(SCC(=O)N3CCCC3)o2)cc1]

In another embodiment, Compounds of formula A3-H do not include 245-(pyridin-3-yl)-1,3,4-oxadiazol-2-ylthio)-1-(pyrrolidin-1-yl)ethanone, having the structure:

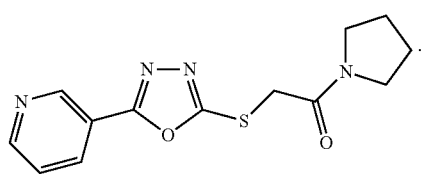 [SMILES: O=C(CSc1nnc(-c2cccnc2)o1)N1CCCC1]

In certain embodiments, provided herein are Compounds of formula A3-I:

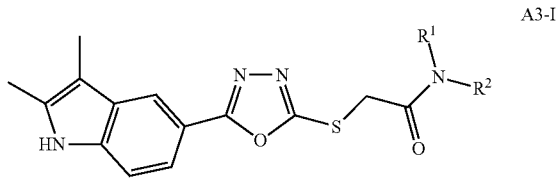

and pharmaceutically acceptable salts, hydrates, solvates, prodrugs and stereoisomers thereof, wherein:

$R^1$ and $R^2$ are at each occurrence independently a $C_1$-$C_8$ alkyl group; or $R^1$ and $R^2$, together with the nitrogen atom $R^1$ and $R^2$ are bound to, form a 3 to 10 membered heterocyclic ring.

In another embodiment, $R^1$ and $R^2$, together with the nitrogen atom $R^1$ and $R^2$ are bound to, form unsubstituted pyrrolidone, unsubstituted isoindoline, unsubstituted morpholine or unsubstituted azepane.

In another embodiment, $R^1$ and $R^2$ are each independently a $C_1$-$C_8$ alkyl group, such as ethyl or isopropyl.

In certain embodiments, provided herein are Compounds of formula A3-J:

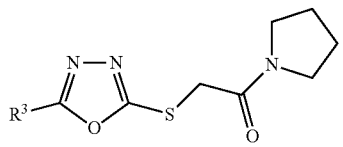

and pharmaceutically acceptable salts, hydrates, solvates, prodrugs and stereoisomers thereof, wherein:

$R^3$ is substituted or unsubstituted indole, substituted or unsubstituted phenyl, substituted or unsubstituted benzofuran, or substituted or unsubstituted pyridine.

In one embodiment, when $R^3$ is substituted or unsubstituted indole, it attached at a position other than the 5-position, as shown below:

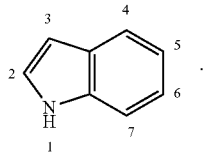

In one embodiment, when $R^3$ is substituted or unsubstituted indole, it is attached at the 2-position, as shown above.

In another embodiment, $R^3$ is unsubstituted indole
In another embodiment, $R^3$ is substituted indole.
In another embodiment, $R^3$ is indole substituted with one or more $C_1$-$C_8$ alkyl groups, such as methyl groups.
In another embodiment, $R^3$ is substituted phenyl.
In another embodiment, $R^3$ is phenyl substituted with one or more sulfonamide groups or one or more $C_1$-$C_8$ alkoxy groups.
In another embodiment, $R^3$ is unsubstituted benzofuran.
In another embodiment, $R^3$ is unsubstituted pyridine.
In one embodiment, Compounds of formula A3-H do not include 2-((5-(2,3-dimethyl-1H-indol-5-yl)-1,3,4-oxadiazol-2-yl)thio)-1-(pyrrolidin-1-yl)ethanone, having the structure:

In one embodiment, Compounds of formula A3-H do not include Compounds wherein $R^3$ is substituted phenyl, such as methoxy substituted phenyl.

In another embodiment, Compounds of formula A3-H do not include Compounds wherein $R^3$ is unsubstituted pyridine.

In another embodiment, Compounds of formula A3-J do not include 2-(5-(4-methoxyphenyl)-1,3,4-oxadiazol-2-ylthio)-1-(pyrrolidin-1-yl)ethanone, having the structure:

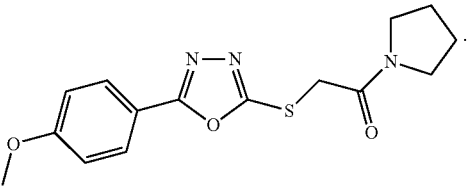 [SMILES: COc1ccc(-c2nnc(SCC(=O)N3CCCC3)o2)cc1]

In another embodiment, Compounds of formula A3-J do not include 245-(pyridin-3-yl)-1,3,4-oxadiazol-2-ylthio)-1-(pyrrolidin-1-yl)ethanone, having the structure:

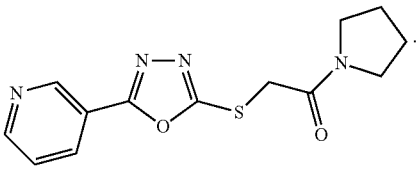 [SMILES: O=C(CSc1nnc(-c2cccnc2)o1)N1CCCC1]

In certain embodiments, provided herein are Compounds of formula A3, A3-1, A3-2, A3-3, A3-4, A3-5, A3-6, A3-7, A3-8, A3-9, A3-11, A3-12 and pharmaceutically acceptable salts, hydrates, solvates, and prodrugs thereof. The Compound of formula A3 (2-(5-(2,3-dimethyl-1H-indol-5-yl)-1,3,4-oxadiazol-2-ylthio)-1-(pyrrolidin-1-yl)ethanone), A3-1 (N,N-diethyl-4-(5-(2-oxo-2-(pyrrolidin-1-yl)ethylthio)-1,3,4-oxadiazol-2-yl)benzenesulfonamide), A3-2 (2-(5-(2,3-dimethyl-1H-indol-5-yl)-1,3,4-oxadiazol-2-ylthio)-N,N-diethylacetamide), A3-3 (2-(5-(2,3-dimethyl-1H-indol-5-yl)-1,3,4-oxadiazol-2-ylthio)-1-(indolin-1-yl)ethanone), A3-4 (2-(5-(2,3-dimethyl-1H-indol-5-yl)-1,3,4-oxadiazol-2-ylthio)-N,N-diisopropylacetamide), A3-5 (2-(5-(2,3-dimethyl-1H-indol-5-yl)-1,3,4-oxadiazol-2-ylthio)-1-morpholinoethanone), A3-6 (1-(azepan-1-yl)-2-(5-(2,3-dimethyl-1H-indol-5-yl)-1,3,4-oxadiazol-2-ylthio)ethanone), A3-7 (2-(5-(1H-indol-2-yl)-1,3,4-oxadiazol-2-ylthio)-1-(pyrrolidin-1-yl)ethanone), A3-8 (2-(5-(4-methoxyphenyl)-1,3,4-oxadiazol-2-ylthio)-1-(pyrrolidin-1-yl)ethanone), A3-9 (2-(5-(benzofuran-2-yl)-1,3,4-oxadiazol-2-ylthio)-1-(pyrrolidin-1-yl)ethanone), A3-11 (2-(5-(pyridin-3-yl)-1,3,4-oxadiazol-2-ylthio)-1-(pyrrolidin-1-yl)ethanone) and A3-12 (2-(5-(pyridin-4-yl)-1,3,4-oxadiazol-2-ylthio)-1-(pyrrolidin-1-yl)ethanone) can be obtained commercially from, for example, Aurora Fine Chemicals LLC, San Diego, USA (Order Numbers kasi-277398, kasi-269536, kasi-277402, kasi-277404, kasi-277407, kasi-277419, and kasi-

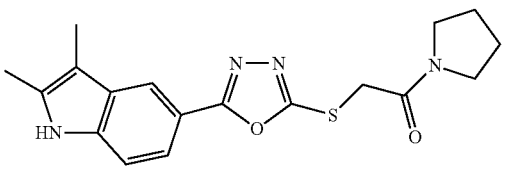

277425, kya-477738, kvt-174532, kend-0119277, kasi-200704), Ryan Scientific Inc., Mt. Pleasant, USA (Order Numbers ASN04454782, ASN04363122, ASN04454791, ASN04454796, ASN04454800, ASN04454819, ASN04454828) or AsInEx, Moscow, Russia (Order Number BAS 04889164, BAS 04370620, BAS06982301).
A3
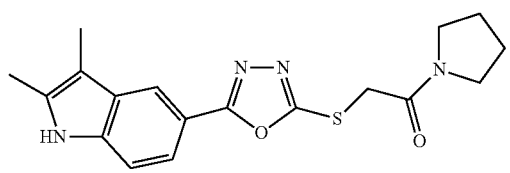
A3-1
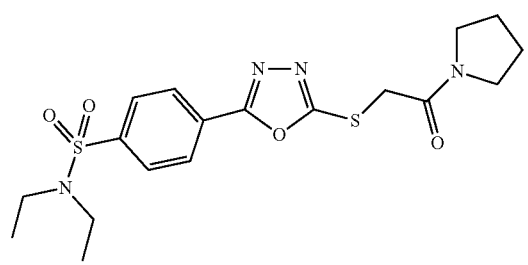
A3-2
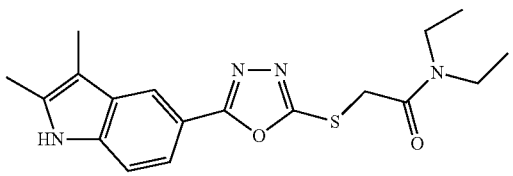
A3-3
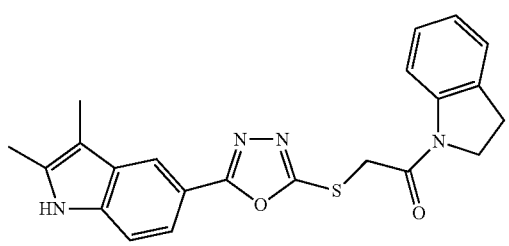
A3-4
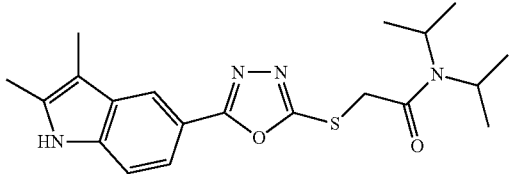
A3-5
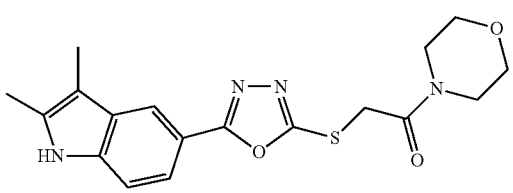
A3-6
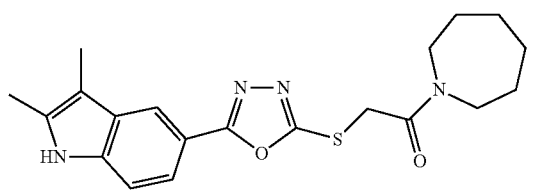
A3-7
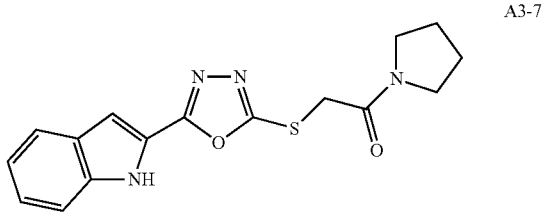
A3-8
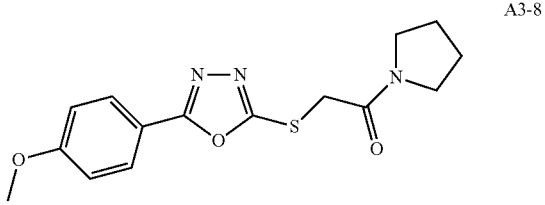
A3-9
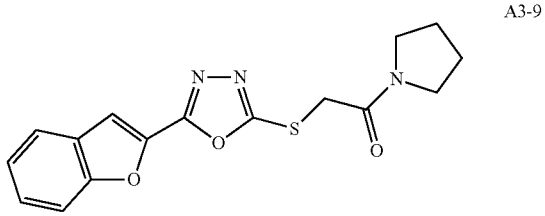
A3-11
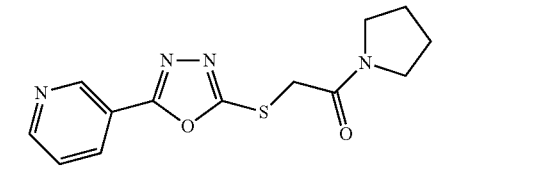
A3-12
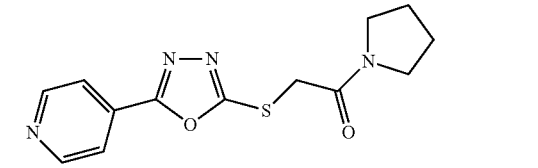
Compounds of formulas A3-H, A3-I and A3-J may be obtained by the chemical synthesis described below or any other method known to one skilled in the art.
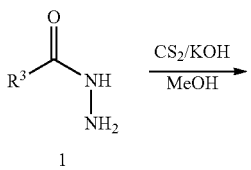
1

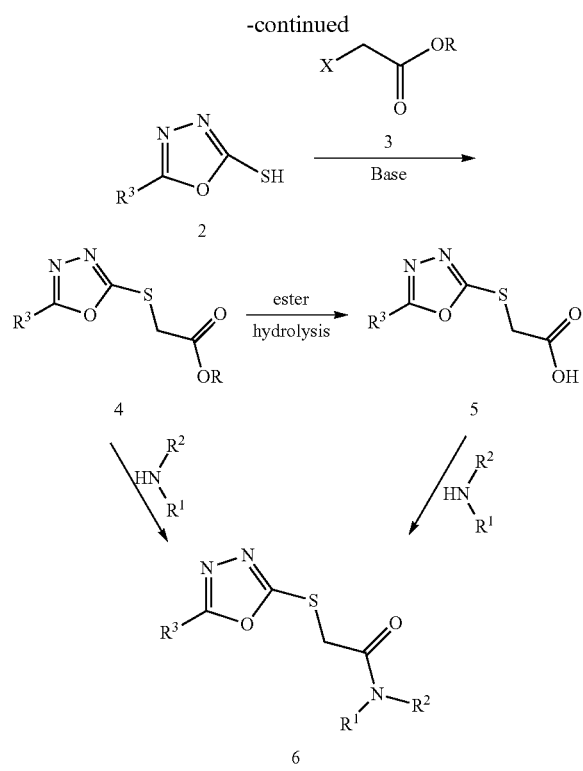

2,3-dimethyl-1H-indole-5-carbohydrazide (1, wherein $R^3$ is 2,3-dimethyl-1H-indole) (ChemCollect GmbH, Remscheid, Germany; Order Number HY008960) may be reacted with carbon disulfide and a suitable base, such as potassium hydroxide, in a suitable solvent, such as methanol, at elevated temperature, such as 65° C. for an appropriate time, such as 7-24 hrs to give 5-(2,3-dimethyl-1H-indol-5-yl)-1,3,4-oxadiazole-2-thiol (2, wherein $R^3$ is 2,3-dimethyl-1H-indole). See Boschelli et al., J. Med. Chem., 1993, 36(13), 1802. Alternatively, the oxadiazole (2) may be obtained reacting (1) with carbon disulfide, $Al_2O_3$ and potassium hydroxide under microwave irradiation. See Khan et al., Letters in Organic Chemistry, 2006, 3, 286. See also Padhy, Indian J. Chem., 2003, 40B, 910; Young et al., J. Am. Chem. Soc., 1955, 77, 118; El-Emam et al., J. Chem. Soc. Pak., 1987, 9, 87. Ester (4) may be obtained by alkylating oxadiazole (2) with a suitable alkylating agent (3), wherein X is a leaving group, such as a Cl, Br, I, or —$SO_2Me$ or any of the leaving groups described in March, Advanced Organic Chemistry, 4th Edition, John Wiley & Sons New York (1992), pp. 352-357 and R is a suitable alkyl group, such as methyl or ethyl, using a suitable base, such as potassium carbonate, in a suitable solvent, such as acetonitrile, at a suitable temperature, such as room temperature to 82° C. In one embodiment thiol (2) may be reacted with bromo methylacetate (Sigma-Aldrich, Milwaukee, USA, Order Number 303208) in acetonitrile using potassium carbonate to give ester (4), wherein R is methyl. Amide (6) may be obtained by reacting $NHR^1R^2$, commercially available or synthesized as described in March, Advanced Organic Chemistry, 4th Edition, John Wiley & Sons New York (1992), with ester (4). See Zabicky, The Chemistry of Amides, Wiley, New York (1970), pp. 96-105. For a list of reagents with references, see Larock, Comprehensive Organic Transformations, VCH New York (1989), pp. 987-988. Strong basic catalysis may be employed, as well as catalysis by cyanide ions or high pressure. See Matsumoto et al., Chem. Ber., 1989, 122, 1357; Högberg et al., J. Org. Chem., 1987, 52, 2033. Alternatively, ester (4) may be hydrolyzed using a suitable base, such as lithium hydroxide, in a suitable solvent or solvent mixture, such as dioxane and water, at a suitable temperature, such as room temperature or 50° C. to give acid (5). Other exemplary methods to hydrolyze esters that may be employed in the synthesis of acid (5) are well-known in the literature and described in March, Advanced Organic Chemistry, 4th Edition, John Wiley & Sons New York (1992), pp. 378-383. Amide (6) may be obtained by reacting acid (5) with a suitable activating agent, such as a mixture of 1-hydroxybenzotriazole and N,N'-dicyclohexylcarbodiimide, in presence of a suitable base, such as diisopropylethylamine, and $HNR^1R^2$ in a suitable solvent, such as N,N-dimethylformamide. Other methods that may be employed to form amide (6) by reacting $HNR^1R^2$ with acid (5) are well-known in the art and described in March, Advanced Organic Chemistry, 4th Edition, John Wiley & Sons New York (1992), pp. 419-421.

5.2 Cellular Assays for Assessing the Effect of a Compound on Viral Replication

Compounds can be assessed for their effects on viral replication or the effects of the Compounds on viral replication can be confirmed by measuring viral replication. The effect of a Compound can be assessed by measuring viral replication using certain assays that are known to the skilled in the art. The assays can be conducted on cells or other substrates, such as embryonated eggs, that contain the virus. Such assays generally involve: (a) contacting a Compound with a cell before (e.g., 15 minutes, 30 minutes, 1 hour, 2 hours, 4 hours, 6 hours, 12 hours, 16 hours, 24 hours or more before), concurrently and/or subsequent to (e.g., 15 minutes, 30 minutes, 1 hour, 2 hours, 4 hours, 6 hours, 12 hours, 16 hours, 24 hours or more after) infection with a virus; and (b) measuring virus replication. The cells can be infected at different MOIs and the effect of a Compound on virus replication can be assessed. For example, the MOIs may be 0.001, 0.005, 0.01, 0.05, 0.1, 0.5, 1, 2.5, or 5 (see Section 5.3.2.1). The effect of different concentrations of a Compound on virus replication can also be assessed. The cells or other substrate that contains cells (e.g., embryonated eggs) used in the assay should be susceptible to infection by the chosen virus. The cells may be primary cells or established cell lines. With respect to influenza virus, for example, the following cells may be used in the assay: chicken cells (e.g., primary chick embryo cells or chick kidney cells), Vero cells, MDCK cells, human respiratory epithelial cells (e.g., A549 cells), calf kidney cells, and mink lung cells. In one embodiment, the cells used to assess the effect of a Compound on virus replication are selected from the following cells or cell lines: MEF, 293T, Huh 7.5, Detroit, MDCK, Vero, HeLa and human tracheobronchial epithelial (HTBE; primary lung cells) cells. In one embodiment, the cell or cell line is biologically relevant to virus infection. With respect to vaccinia virus, for example, CV 1 cells may be used in the assay. With respect to adenovirus, Newcastle disease virus and Sendai virus, for example, A549 cells may be used in the assay. With respect to hepatitis C virus, for example, HuH7.5 cells may be used in the assay. With respect to Dengue virus (DenV-1) and West Nile virus (WNV), for example, Vero cells may be used in the assay. With respect to HIV-1, for example, TZM-bl cells (HeLa cells that express a tat inducible beta-galactosidase reporter gene) may be used (see Section 5.2.2).

Virus replication can be measured at different times post-infection. For example, virus replication may be measured 6 hours, 12 hours, 16 hours, 24 hours, 48 hours or 72 hours post-infection. Any method known to one of skill in the art can be used measure virus replication. For example, viral replication may be assessed by measuring viral titer (as determined, e.g., by plaque formation), the production of viral proteins (as determined, e.g., by western blot analysis, ELISA or flow cytometry), or the production of viral nucleic acids (as determined, e.g., by RT-PCR or Northern blot analysis) using techniques known to one of skill in the art. See Sections 5.2.2.1-5.3.2.8 below for more details of techniques for measuring viral replication.

In one embodiment, inhibition or reduction in viral replication is measured using an assay as described in Section 5.2.2.1-5.2.2.8 infra. In one embodiment, a decrease in viral replication is measured by: (a) contacting a Compound with a cell before (e.g., 15 minutes, 30 minutes, 1 hour, 2 hours, 4 hours, 6 hours, 12 hours, 16 hours, 24 hours or more before), concurrently and/or subsequent to (e.g., 15 minutes, 30 minutes, 1 hour, 2 hours, 4 hours, 6 hours, 12 hours, 16 hours, 24 hours or more after) infection; and (b) measuring virus replication. The cells used in the assay should be susceptible to infection by the chosen virus and can be infected at different MOIs. The effect of a Compound on virus replication can be assessed by measuring virus replication at different times post-infection. For example, virus replication may be measured 6 hours, 12 hours, 16 hours, 24 hours, 48 hours or 72 hours post-infection, using any method known to one of skill in the art can be used measure virus replication. In one embodiment, a decrease in viral replication is assessed by measuring viral titer (as determined, e.g., by plaque formation). In another embodiment, a decrease in viral replication is assessed by measuring the production of viral proteins (as determined, e.g., by Western blot analysis, ELISA or flow cytometry). In another embodiment, a decrease in viral replication is assessed by measuring the production of viral nucleic acids (as determined, e.g., by RT-PCR or Northern blot analysis) using techniques known to one of skill in the art. See Sections 5.2.2.1-5.2.2.8 below for more details of techniques for measuring viral replication. In certain embodiments, a Compound reduces the virus replication by at least 1.5 fold, 2, fold, 3, fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to virus replication in the absence of the Compound or the presence of a negative control. In a specific embodiment, a Compound reduces the virus replication by at least 2 log relative to virus replication in the absence of the Compound or the presence of a negative control. In certain embodiments, a Compound reduces the virus replication by 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold. In a specific embodiment, a Compound reduces the viral replication by approximately 2 logs or more, approximately 3 logs or more, approximately 4 logs or more, approximately 5 logs or more, or 2 to 10 logs or 2 to 5 logs relative to virus replication in the absence of the Compound or the presence of a negative control.

In one embodiment, the effect of a Compound on the replication of a virus may be determined by infecting cells with different dilutions of a virus in the presence or absence of various dilutions of a Compound, and assessing the effect of the Compound on, e.g., viral replication, viral genome replication, and/or the synthesis of viral proteins. In another embodiment, the effect of a Compound on the replication of a virus may be determined by contacting cells with various dilutions of a Compound or a placebo, infecting the cells with different dilutions of a virus, and assessing the effect of the Compound on, e.g., viral replication, viral genome replication, and/or the synthesis of viral proteins. Altered viral replication can be assessed by, e.g., plaque formation. The production of viral proteins can be assessed by, e.g., ELISA, Western blot, or flow cytometry analysis. The production of viral nucleic acids can be assessed by, e.g., RT-PCR, PCR, Northern blot analysis, or Southern blot.

In the assays described above, a Compound that decreases the replication of a virus is identified if the replication of the virus is decreased in the cell contacted with the Compound relative to the replication of the virus in a cell contacted with a negative control (e.g., PBS or saline).

The antiviral activity of Compounds may be assessed in various in vitro assays described herein or others known to one of skill in the art. In specific embodiments, Compounds exhibit an activity profile that is consistent with their ability to inhibit viral replication while maintaining low toxicity with respect to eukaryotic cells, preferably mammalian cells.

In certain embodiments, a Compound reduces the replication of a virus by at least 1.5 fold, 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to virus replication in the absence of Compound or the presence of a negative control. In certain embodiments, a Compound reduces the virus replication by 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold. In a specific embodiment, a Compound reduces the virus replication by approximately 2 logs or more, approximately 3 logs or more, approximately 4 logs or more, approximately 5 logs or more, or 2 to 10 logs or 2 to 5 logs relative to virus replication in the absence of Compound or the presence of a negative control. In certain embodiments, a Compound reduces the replication of a virus by at least 1 log, 1.5 logs, 2 logs, 2.5 logs, 3 logs, 3.5 logs, 4 logs, 4.5 logs, 5 logs, 5.5 logs, 6 logs or more relative to replication of the virus in the absence of a Compound or relative to a negative control in an assay described herein or others known to one of skill in the art.

In certain embodiments, a Compound reduces the replication of a viral genome by about at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to replication of the viral genome in the absence of a Compound or relative to a negative control in an assay described herein or others known to one of skill in the art. In certain embodiments, a Compound reduces the replication of a viral genome by about 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to replication of the viral genome in the absence of a Compound or relative to a negative control in an assay described herein or others known to one of skill in the art. In a specific embodiment, a Compound reduces the replication of a viral genome by approximately 2 logs or more, approximately 3 logs or more, approximately 4 logs or more, approximately 5 logs or more, or 2 to 10 logs or 2 to 5 logs relative to replication of the viral genome in the absence of Compound or relative to a negative control. In certain embodiments, a Compound reduces the replication of a viral genome by at least 1 log, 1.5 logs, 2 logs, 2.5 logs, 3 logs, 3.5 logs, 4 logs, 4.5 logs, 5 logs, 5.5 logs, 6 logs or more relative to replication of the viral genome in the absence of a Compound or relative to a negative control in an assay described herein or others known to one of skill in the art.

In certain embodiments, a Compound reduces the synthesis of viral proteins by at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to the synthesis of viral proteins in the absence of a Compound or relative to a negative control in an assay described herein or others known to one of skill in the art in an assay described herein or others known to one of skill in the art. In certain embodiments, a Compound reduces the synthesis of viral proteins at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to the synthesis of viral proteins in the absence of a Compound or relative to a negative control in an assay described herein or others known to one of skill in the art. In a specific embodiment, a Compound reduces the synthesis of viral proteins by approximately 2 logs or more, approximately 3 logs or more, approximately 4 logs or more, approximately 5 logs or more, or 2 to 10 logs or 2 to 5 logs relative to the synthesis of viral proteins in the absence of Compound or relative to a negative control. In certain embodiments, a Compound reduces the synthesis of viral proteins approximately 1 log, 1.5 logs, 2 logs, 2.5 logs, 3 logs, 3.5 logs, 4 logs, 4.5 logs, 5 logs relative to the synthesis of viral proteins in the absence of a Compound or relative to a negative control in an assay described herein or others known to one of skill in the art.

In some embodiments, a Compound results in 1.5 fold or more, 2 fold or more, 3 fold or more, 4 fold or more, 5 fold or more, 6 fold or more, 7 fold or more, 8 fold or more, 9 fold or more, 10 fold or more, 15 fold or more, 20 fold or more, 25 fold or more, 30 fold or more, 35 fold or more, 40 fold or more, 45 fold or more, 50 fold or more, 60 fold or more, 70 fold or more, 80 fold or more, 90 fold or more, or 100 fold or more reduction of viral yield per round of viral replication. In certain embodiments, a Compound results in about a 2 fold or more reduction of viral yield per round of viral replication. In a specific embodiment, a Compound results in about a 10 fold or more reduction of viral yield per round of viral replication.

In certain embodiments, a Compound reduces viral replication by at least 2 wells of hemagglutinin (HA) in a hemagglutination assay (see Section 5.2.1.7 below), which equals approximately a 75% reduction in viral titer. In certain embodiments, a Compound reduces viral titer by 50% or more, by 55% or more, by 60% or more, by 65% or more, by 70% or more, by 75% or more, by 80% or more, by 85% or more, by 90% or more, or by 95% or more.

The effect of a Compound on the replication of any virus may be determined. The effect of a Compound on the replication of any type, subtype or strain of a virus, including a DNA virus, a positive-sense, single-stranded RNA virus, a negative-sense, single-stranded RNA virus, a double-stranded RNA virus and/or a retrovirus, may be determined. The double-stranded RNA virus may be a non-segmented or a segmented virus. In certain embodiments, the DNA virus is a cytoplasmic double-stranded DNA virus. In certain embodiments, the cytoplasmic double-stranded DNA virus is a Poxvirus (Poxyiridae). In certain embodiments, the Poxvirus is a vaccinia virus. In certain embodiments, the DNA virus is a nuclear double-stranded DNA virus. In certain embodiments, the cytoplasmic double-stranded DNA virus is an Adenovirus. Non-limiting examples of viruses can be found in Section 5.5.1. In certain embodiments, the Adenovirus is a human adenovirus. In certain embodiments, the human adenovirus is HAdV. In certain embodiments, the HAdV is HAdV-A, HAdV-B, HAdV-C, HAdV-D, HAdV-E, or HAdV-F. In certain embodiments, the RNA virus is a positive-sense, single-stranded RNA virus. In certain embodiments, the positive-sense, single-stranded RNA virus is Flavivirus (Flaviviridae). In certain embodiments, the Flavivirus is a Dengue virus, hepatitis C virus, or a West Nile virus. In certain embodiments, the positive-sense single-stranded RNA virus is Togavirus (Togaviridae). In certain embodiments, the Togavirus is Sindbis virus. In certain embodiments, the positive-sense single-stranded RNA virus is a retrovirus (Retroviridae). In certain embodiment, the retrovirus is human immunodeficiency virus (HIV). In certain embodiment, the HIV is HIV type 1. In certain embodiments, the negative-sense single-stranded RNA is a rhabdovirus. In certain embodiments, the rhabdovirus is a Vesicular Stomatitis virus. In certain embodiments, the negative-sense single-stranded RNA is a paramyxovirus. In certain embodiments, the paramyxovirus is a Newcastle disease virus or respiratory syncytial virus. In certain embodiments, the paramyxovirus is Sendai virus.

The antiviral activities of Compounds against any type, subtype or strain of virus can be assessed. For example, the antiviral activity of Compounds against naturally occurring strains, variants or mutants, mutagenized viruses, reassortants and/or genetically engineered viruses can be assessed.

In some embodiments, the inhibitory effect of a Compound on the replication of an attenuated DNA virus, positive-sense, single-stranded RNA virus, double-stranded RNA virus, negative-sense, single-stranded RNA virus, and retrovirus is determined. In some embodiments, the inhibitory effect of a Compound on the replication of a naturally occurring strain, variant or mutant of a virus, including a DNA virus, a positive-sense, single-stranded RNA virus, a double-stranded RNA virus, a negative-sense, single-stranded RNA virus, and a retrovirus, a mutagenized negative-sense, single-stranded RNA virus, a reassortant virus, a positive-sense, single-stranded RNA virus, a negative-sense, single-stranded RNA virus, a double-stranded RNA virus and a retrovirus and/or a genetically engineered virus, a positive-sense, single-stranded RNA virus, a double-stranded RNA virus, a negative-sense, single-stranded RNA virus, and a retrovirus can be assessed. In a specific embodiment, the inhibitory effect of a Compound on the replication of a vaccine strain of a virus, including a positive-sense, single-stranded RNA virus, a negative-sense, single-stranded RNA virus, a double-stranded RNA virus and a retrovirus, is determined.

The lethality of certain viruses, the safety issues concerning working with certain viruses and/or the difficulty in working with certain viruses may preclude (at least initially) the characterization of the antiviral activity of Compounds on such viruses. Under such circumstances, other animal viruses that are representative of such viruses may be utilized. For example, SIV may be used initially to characterize the antiviral activity of Compounds against HIV. Further, Pichinde virus may be used initially to characterize the antiviral activity of Compounds against Lassa fever virus.

5.2.1 Characterization of Antiviral Activity of Compounds in Cell Lines

The in vitro antiviral assays can be conducted using any eukaryotic cell, including primary cells and established cell lines. The cell or cell lines selected should be susceptible to infection by a virus of interest. Non-limiting examples of mammalian cell lines that can be used in standard in vitro antiviral assays (e.g., viral cytopathic effect assays, neutral red update assays, viral yield assay, plaque reduction assays) for the respective viruses are set out in Table 1.

TABLE 1

Examples of Mammalian Cell Lines in Antiviral Assays

| Virus | cell line |
|---|---|
| Vaccinia virus | CV1 cells |
| herpes simplex virus (HSV) | primary fibroblasts (MRC-5 cells) |
| | Vero cells |
| Adenovirus | A549 cells |
| Newcastle disease virus | A549 cells |
| Sendai virus | A549 cells |
| human cytomegalovirus (HCMV) | primary fibroblasts (MRC-5 cells) |
| Influenza | Madin Darby canine kidney (MDCK) |
| | primary chick embryo |
| | chick kidney |
| | calf kidney |
| | African green monkey kidney (Vero) cells |
| | mink lung |
| | human respiratory epithelia cells |
| hepatitis C virus | Huh7 (or Huh7.5) |
| | primary human hepatocytes (PHH) |
| | immortalized human hepatocytes (IHH) |
| HIV-1 | MT-2 cells (T cells), HeLa cells, TZM-bl cells |
| Dengue virus | Vero cells |
| Measles virus | African green monkey kidney (CV-1) cells |
| SARS virus | Vero 76 cells |
| Respiratory syncytial virus | African green monkey kidney (MA-104) cells |
| Venezuelan equine encephalitis virus | Vero cells |
| West Nile virus | Vero cells |
| yellow fever virus | Vero cells |
| HHV-6 | Cord Blood Lymphocytes (CBL) |
| | Human T cell lymphoblastoid cell lines (HSB-2 and SupT-1) |
| HHV-8 | B-cell lymphoma cell line (BCBL-1) |
| EBV | umbilical cord blood lymphocytes |

Assays can be adapted to be used to measure the antiviral activity of a Compound against various types of viruses. One of skill in the art will know how to adapt the methods of measuring the antiviral activity of a Compound as described in Sections 5.2.2.1 to 5.2.2.8 to other viruses by, e.g., varying the cell system and viral pathogen, such as described in Table 1.

Various cell lines for use in antiviral assays can be genetically engineered to render them more suitable hosts for viral infection or viral replication and more convenient substrates for rapidly detecting virus-infected cells (See, e.g., Olivo, P. D., Clin. Microbiol. Rev., 1996, 9:321-334). In some aspects, these cell lines are available for testing the antiviral activity of Compound on blocking any step of viral replication, such as, transcription, translation, pregenome encapsidation, reverse transcription, particle assembly and release. Nonlimiting examples of genetically engineered cells lines for use in antiviral assays with the respective virus are discussed below.

HepG2-2.2.15 is a stable cell line containing the hepatitis B virus (HBV) ayw strain genome that is useful in identifying and characterizing Compounds blocking any step of viral replication, such as, transcription, translation, pregenome encapsidation, reverse transcription, particle assembly and release. In one aspect, Compounds can be added to HepG2-2.2.15 culture to test whether Compound will reduce the production of secreted HBV from cells utilizing real time quantitative PCR (TaqMan) assay to measure HBV DNA copies. Specifically, confluent cultures of HepG2-2.2.15 cells cultured on 96-well flat-bottomed tissue culture plates and are treated with various concentrations of daily doses of Compounds. HBV virion DNA in the culture medium can be assessed 24 hours after the last treatment by quantitative blot hybridization or real time quantitative PCR (TaqMan) assay. Uptake of neutral red dye (absorbance of internalized dye at 510 nM [A510]) can be used to determine the relative level of toxicity 24 hours following the last treatment. Values are presented as a percentage of the average A510 values for separate cultures of untreated cells maintained on the same plate. Intracellular HBV DNA replication intermediates can be assessed by quantitative Southern blot hybridization. Intracellular HBV particles can be isolated from the treated HepG2-2.2.15 cells and the pregenomic RNA examined by Southern blot analysis. ELISAs can be used to quantify the amounts of the HBV envelope protein, surface antigen (HBsAg), and secreted e-antigen (HBeAg) released from cultures. Lamivudine (3TC) can be used as a positive assay control. (See Korba & Gerin, Antivir. Res. 19:55-70, 1992).

In one aspect, the cell line Huh7 ET (luc-ubi-neo/ET), which contains a new HCV RNA replicon with a stable luciferase (LUC) reporter, can be used to assay Compounds antiviral activity against hepatitis C viral replication (See Krieger, N., V. Lohmann, and R. Bartenschlager J. Virol., 2001, 75:4614-4624). The activity of the LUC reporter is directly proportional to HCV RNA levels and positive control antiviral Compounds behave comparably using either LUC or RNA endpoints. Subconfluent cultures of Huh7 ET cells are plated onto 96-well plates, Compounds are added to the appropriate wells the next day, and the samples as well as the positive (e.g., human interferon-alpha 2b) and negative control samples are processed 72 hr later when the cells are still subconfluent. The HCV RNA levels can also be assessed using quantitative PCR (TaqMan). In some embodiments, Compounds reduce the LUC signal (or HCV RNA levels) by 20%, 35%, 30%, 35%, 40%, 45%, 50%, 55%, 60%, 65%, 70%, 75%, 80%, 90%, or 95% or more relative to the untreated sample controls. In a preferred embodiment, Compounds reduce the LUC signal (or HCV RNA levels) by 50% or more relative to the untreated cell controls. Other relevant cell culture models to study HCV have been described, e.g., See Durantel et al., J. Hepatology, 2007, 46:1-5.

The antiviral effect of Compound can be assayed against EBV by measuring the level of viral capsid antigen (VCA) production in Daudi cells using an ELISA assay. Various concentrations of Compounds are tested (e.g., 50 mg/ml to 0.03 mg/ml), and the results obtained from untreated and Compound treated cells are used to calculate an EC50 value. Selected Compounds that have good activity against EBV VCA production without toxicity will be tested for their ability to inhibit EBV DNA synthesis.

For assays with HSV, the BHKICP6LacZ cell line, which was stably transformed with the *E. coli* lacZ gene under the transcriptional control of the HSV-1 UL39 promoter, can be used (See Stabell et al., 1992, Methods 38:195-204). Infected cells are detected using β-galactosidase assays known in the art, e.g., colorimetric assay.

Standard antiviral assays for influenza virus has been described, See, e.g., Sidwell et al., Antiviral Research, 2000, 48:1-16. These assays can also be adapted for use with other viruses.

In certain embodiments, the effect of a Compound on influenza A virus is determined using a reporter assay. Such a reporter assay involve the use of an influenza mini-genome reporter construct to encode firefly luciferase in the negative sense in between the cRNA promoter of the influenza A/WSN/33 virus NP segment. This construct can be cloned into a plasmid flanked by a human RNA polymerase I promoter and the hepatitis D virus (HDV) ribozyme. Upon transfection of this reporter into cells, such as human lung epithelial (A549) cells, RNA polymerase I transcription generates an RNA segment that mimics viral RNA. When these cells are subsequently infected with influenza virus, this segment is recognized by the viral polymerase resulting in the production of firefly luciferase mRNA. Luciferase activity therefore serves as a measurement of influenza virus replication and decreases in this signal that are observed in the presence of specific Compounds are indicative of inhibitory activities. Due to the fact that a high multiplicity of infection provided the greatest reproducibility, the assay is particularly useful for detecting Compounds that act on steps up to and including translation. To detect Compounds that act on later stages such as assembly, budding and release, a multicycle format could be used. Assay that rely on virus-induced cytopathic effect (CPE) as readout and use a low multiplicity of infection (Noah et al., 2007) can be used to detect Compounds that affect influenza viral replication.

5.2.1.1 Viral Titer Assay

In this non-limiting example, a monolayer of the target mammalian cell line is infected with different amounts (e.g., multiplicity of 3 plaque forming units (pfu) or 5 pfu) of virus (e.g., influenza) and subsequently cultured in the presence or absence of various dilutions of Compounds (e.g., 0.1 µg/ml, 1 µg/ml, 5 µg/ml, or 10 µg/ml). Infected cultures are harvested 48 hours or 72 hours post infection and titered by standard plaque assays known in the art on the appropriate target cell line (e.g., Vero cells). In certain embodiments, culturing the infected cells in the presence of Compounds reduces the yield of infectious virus by at least 1.5 fold, 2, fold, 3, fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to culturing the infected cells in the absence of Compounds. In a specific embodiment, culturing the infected cells in the presence of Compounds reduces the PFU/ml by at least 10 fold relative to culturing the infected cells in the absence of Compounds.

In certain embodiments, culturing the infected cells in the presence of Compounds reduces the yield of infectious virus by at least 0.5 log, 1 log, 1.5 log, 2 logs, 2.5 logs, 3 logs, 3.5 logs, 4 logs, 4.5 logs, 5 log, 5.5 logs, 6 logs, 6.5 logs, 7 logs, 7.5 logs, 8 logs, 8.5 logs, or 9 logs relative to culturing the infected cells in the absence of Compounds. In a specific embodiment, culturing the infected cells in the presence of Compounds reduces the yield of infectious virus by at least 1 log or 2 logs relative to culturing the infected cells in the absence of Compounds. In another specific embodiment, culturing the infected cells in the presence of Compounds reduces the yield of infectious virus by at least 2 logs relative to culturing the infected cells in the absence of Compounds.

5.2.1.2 Flow Cytometry Assay

Flow cytometry can be utilized to detect expression of virus antigens in infected target cells cultured in the presence or absence of Compounds (See, e.g., McSharry et al., Clinical Microbiology Rev., 1994, 7:576-604). Non-limiting examples of viral antigens that can be detected on cell surfaces by flow cytometry include, but are not limited to HA of influenza; and H and F of measles virus. In other embodiments, intracellular viral antigens or viral nucleic acid can be detected by flow cytometry with techniques known in the art.

5.2.1.3 Viral Cytopathic Effect (CPE) Assay

CPE is the morphological changes that cultured cells undergo upon being infected by most viruses. These morphological changes can be observed easily in unfixed, unstained cells by microscopy. Forms of CPE, which can vary depending on the virus, include, but are not limited to, rounding of the cells, appearance of inclusion bodies in the nucleus and/or cytoplasm of infected cells, and formation of syncytia, or polykaryocytes (large cytoplasmic masses that contain many nuclei).

The CPE assay can provide a measure of the effect of a Compound on virus replication. In a non-limiting example of such an assay, Compounds are serially diluted (e.g. 1000, 500, 100, 50, 10, 1 µg/ml) and added to 3 wells containing a cell monolayer (preferably mammalian cells at 80-100% confluent) of a 96-well plate. Within 5 minutes, viruses are added and the plate sealed, incubated at 37° C. for the standard time period required to induce near-maximal viral CPE (e.g., approximately 48 to 120 hours, depending on the virus and multiplicity of infection). When assaying a Compound for its potential inhibitory activity, CPE is read microscopically after a known positive control drug (an antiviral) is evaluated in parallel with Compounds in each test. A non-limiting example of a positive control is ribavirin for influenza virus, measles virus, respiratory syncytial virus, and parainfluenza virus. The data is expressed as 50% effective concentrations or approximated virus-inhibitory concentration, 50% endpoint (EC50) and cell-inhibitory concentration, 50% endpoint ($IC_{50}$). General selectivity index ("SI") is calculated as the $IC_{50}$ divided by the EC50. These values can be calculated using any method known in the art, e.g., the computer software program MacSynergy II by M. N. Prichard, K. R. Asaltine, and C. Shipman, Jr., University of Michigan, Ann Arbor, Mich.

In one embodiment, a Compound has an SI of greater than 3, 4, 5, 6, 7, 8, 9, 10, 11, 12, 13, 14, 15, 20, 21, 22, 23, 24, 25, 30, 35, 39, 40, 45, 50, 60, 70, 80, 90, 100, 200, 300, 400, 500, 1,000, or 10,000. In some embodiments, a Compound has an SI of greater than 10. In a specific embodiment, Compounds with an SI of greater than 10 are further assessed in other in vitro and in vivo assays described herein or others known in the art to characterize safety and efficacy.

5.2.1.4 Neutral Red (NR) Dye Uptake Assay

The NR Dye Uptake assay can be used to validate the CPE inhibition assay (See Section 5.2.1.3). In a non-limiting example of such an assay, the same 96-well microplates used for the CPE inhibition assay can be used. Neutral red is added to the medium, and cells not damaged by virus take up a greater amount of dye. The percentage of uptake indicating viable cells is read on a microplate autoreader at dual wavelengths of 405 and 540 nm, with the difference taken to eliminate background. (See McManus et al., Appl. Environment. Microbiol. 31:35-38, 1976). An $EC_{50}$ is determined for samples with infected cells and contacted with Compounds, and an $IC_{50}$ is determined for samples with uninfected cells contacted with Compounds.

5.2.1.5 Virus Yield Assay

Lysed cells and supernatants from infected cultures such as those in the CPE inhibition assay (See Section 5.3.1.3) can be used to assay for virus yield (production of viral particles after the primary infection). In a non-limiting example, these supernatants are serially diluted and added onto monolayers of susceptible cells (e.g., Vero cells). Development of CPE in these cells is an indication of the presence of infectious viruses in the supernatant.

5.2.1.6 Plaque Reduction Assay

In a non-limiting example of a plaque assay, the virus is diluted into various concentrations and added to each well containing a monolayer of the target cells in triplicate. The plates are then incubated for a period of time to achieve effective infection of the control sample (e.g., 1 hour with shaking every fifteen minutes). After the incubation period, an equal amount of 1% agarose is added to an equal volume of each Compound dilution prepared in 2× concentration. In certain embodiments, final Compound concentrations between 0.03 µg/ml to 100 µg/ml can be tested with a final agarose overlay concentration of 0.5%. The drug agarose mixture is applied to each well in 2 ml volume and the plates are incubated for three days, after which the cells are stained with a 1.5% solution of neutral red. At the end of the 4-6 hour incubation period, the neutral red solution is aspirated, and plaques counted using a stereomicroscope. Alternatively, a final agarose concentration of 0.4% can be used. In other embodiments, the plates are incubated for more than three days with additional overlays being applied on day four and on day 8 when appropriate. In another embodiment, the overlay medium is liquid rather than semi-solid.

5.2.1.7 Hemagglutination Assays

In a non-limiting example of a hemagglutination assay, cells are contacted with a Compound and are concurrently or subsequently infected with the virus (e.g., at an MOI of 1) and the virus is incubated under conditions to permit virus replication (e.g., 20-24 hours). The Compounds are preferably present throughout the course of infection. Viral replication and release of viral particles is then determined by hemagglutination assays using 0.5% chicken red blood cells. In some embodiments, a Compound is considered an inhibitor of viral replication if it reduces viral replication by at least 2 wells of HA, which equals approximately a 75% reduction in viral titer. In specific embodiments, a Compound reduces viral titer in this assay by 50% or more, by 55% or more, by 60% or more, by 65% or more, by 70% or more, by 75% or more, by 80% or more, by 85% or more, by 90% or more, or by 95% or more.

5.2.1.8 Apoptosis Assay

Any technique known to one of skill in the art can be used to determine whether a Compound has an apoptotic effect. For example, a fluorescence-based assay for caspase-3 activity can be used to detect whether a Compound has a pro- or anti-apoptotic effect. In one example of such an assays, cells are seeded into 60 mm tissue culture treated dishes at $1.5 \times 10^6$ cells per dish and allowed to incubate for 24 hours. After incubation, the medium is aspirated and the cells are washed with PBS. Fresh DMEM post-infection medium was added, containing Compounds at the same concentrations as has been used for the viral infections. As a positive control for the induction of apoptosis, cells are treated with any known inducer of apoptosis, for example, staurosporin at a concentration of 5 µM. Cells are incubated for 6 hours. Subsequently, they are harvested, washed twice with PBS, lysed and incubated with the colorimetric substrate for an additional hour, at which time fluorescence is measured. An increase in fluorescence relative to a negative control or cells not treated with the Compound indicates that the Compound is pro-apoptotic.

5.3 Characterization of Safety and Efficacy of Compounds

The safety and efficacy of Compounds can be assessed using technologies known to one of skill in the art. Sections 5.3.1 and 5.3.2 below provide non-limiting examples of cytotoxicity assays and animal model assays, respectively, to characterize the safety and efficacy of Compounds. In certain embodiments, the cytotoxicity assays described in Section 5.3.1 are conducted following the in vitro antiviral assays described in Section 5.2.1, supra. In other embodiments, the cytotoxicity assays described in Section 5.3.1 are conducted before or concurrently with the in vitro antiviral assays described in Section 5.2.1, supra.

In some embodiments, Compounds differentially affect the viability of uninfected cells and cells infected with virus. The differential effect of a Compound on the viability of virally infected and uninfected cells may be assessed using techniques such as those described in Section 5.2.1, infra, or other techniques known to one of skill in the art. In certain embodiments, Compounds are more toxic to cells infected with a virus than uninfected cells. In specific embodiments, Compounds preferentially affect the viability of cells infected with a virus. Without being bound by any particular concept, the differential effect of a Compound on the viability of uninfected and virally infected cells may be the result of the Compound targeting a particular enzyme or protein (e.g., a viral polymerase) that is differentially expressed or regulated or that has differential activities in uninfected and virally infected cells. For example, viral infection and/or viral replication in an infected host cells may alter the expression, regulation, and/or activities of enzymes and/or proteins. Non-limiting examples of antiviral assays that can be used to assess the antiviral activity of Compound are provided in Section 5.2.1, supra.

5.3.1 Cytotoxicity Studies

Many assays well-known in the art can be used to assess viability of cells (infected or uninfected) or cell lines following exposure to a Compound and, thus, determine the cytotoxicity of the Compound. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270:18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy-80%), PH (partially toxic—heavy-60%), P (partially toxic-40%), Ps (partially toxic—slight-20%), or 0 (no toxicity-0%), conforming to the degree of cytotoxicity seen. A 50% cell inhibitory (cytotoxic) concentration (IC50) is determined by regression analysis of these data.

In a specific embodiment, the cells are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. Other non-limiting examples of cell lines that can be used to test the cytotoxicity of Compounds are provided in Table 1.

Compounds can be tested for in vivo toxicity in animal models. For example, animal models, described herein and/or others known in the art, used to test the antiviral activities of Compounds can also be used to determine the in vivo toxicity of these Compounds. For example, animals are administered a range of concentrations of Compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a Compound can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. A Compound identified that exhibits large therapeutic indices is preferred. While a Compound identified that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a Compound identified for use in humans. The dosage of such agents lies preferably within a range of circulating concentrations that include the ED50 with little or no toxicity. The dosage may vary within this range depending upon the dosage form employed and the route of administration utilized. For any agent used in the method described herein, the therapeutically effective dose can be estimated initially from cell culture assays. A dose may be formulated in animal models to achieve a circulating plasma concentration range that includes the IC50 (i.e., the concentration of the test Compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided in Section 5.9, infra.

In some embodiments, the Compound does not have an inhibitory effect on the overall host cell replication machinery, or has only a slight inhibitory effect compared to the effect on viral replication, as monitored by assays such as, e.g., the expression of a *renilla* luciferase reporter from a control plasmid (e.g., pGL3 described in Section 6.2 below).

5.3.2 Animal Model Studies

Compounds and compositions are preferably assayed in vivo for the desired therapeutic or prophylactic activity prior to use in humans. For example, in vivo assays can be used to determine whether it is preferable to administer a Compound and/or another therapeutic agent. For example, to assess the use of a Compound to prevent a viral infection or the pathological state resulting therefrom, the Compound can be administered before the animal is infected with the virus. Alternatively, or in addition, a Compound can be administered to the animal at the same time that the animal is infected with the virus. To assess the use of a Compound to treat or manage a viral infection or the pathological state resulting therefrom, in one embodiment, the Compound is administered after a viral infection in the animal. In another embodiment, a Compound is administered to the animal at the same time that the animal is infected with the virus to treat and/or manage the viral infection or the pathological state resulting therefrom. In a specific embodiment, the Compound is administered to the animal more than one time.

Compounds can be tested for antiviral activity against virus in animal models systems including, but are not limited to, rats, mice, chicken, cows, monkeys, pigs, goats, sheep, dogs, rabbits, guinea pigs, etc. In a specific embodiment, Compounds are tested in a mouse model system. Such model systems are widely used and well-known to the skilled artisan. Compounds can also be tested for replication enhancing activity toward virus replication in animal models systems including, but are not limited to, rats, mice, chicken, cows, monkeys, pigs, goats, sheep, dogs, rabbits, guinea pigs, etc. In a specific embodiment, Compounds are tested in a mouse model system. Such model systems are widely used and well-known to the skilled artisan. Non-limiting examples of animal models for influenza virus are provided in Section 5.3.2.5 below.

Animals are infected with virus and concurrently or subsequently treated with a Compound or placebo. Alternatively, animals are treated with a Compound or placebo and subsequently infection with virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of a Compound on the virulence of a virus can also be determined using in vivo assays in which the titer of the virus in an infected subject administered a Compound, the length of survival of an infected subject administered a Compound, the immune response in an infected subject administered a Compound, the number, duration and/or severity of the symptoms in an infected subject administered a Compound, and/or the time period before onset of one or more symptoms in an infected subject administered a Compound is assessed. Techniques known to one of skill in the art can be used to measure such effects.

5.3.2.1 Herpes Simplex Virus (HSV)

Mouse models of herpes simplex virus type 1 or type 2 (HSV-1 or HSV-2) can be employed to assess the antiviral activity of Compounds in vivo. BALB/c mice are commonly used, but other suitable mouse strains that are susceptible can also be used. Mice are inoculated by various routes with an appropriate multiplicity of infection of HSV (e.g., 105 pfu of HSV-1 strain E-377 or $4^{\times 10}$ 4 pfu of HSV-2 strain MS) followed by administration of Compounds and placebo. For i.p. inoculation, HSV-1 replicates in the gut, liver, and spleen and spreads to the CNS. For i.n. inoculation, HSV-1 replicates in the nasaopharynx and spreads to the CNS. Any appropriate route of administration (e.g., oral, topical, systemic, nasal), frequency and dose of administration can be tested to determine the optimal dosages and treatment regimens using Compounds, optionally in combination with other therapies.

In a mouse model of HSV-2 genital disease, intravaginal inoculation of female Swiss Webster mice with HSV-1 or HSV-2 is carried out, and vaginal swabs are obtained to evaluate the effect of therapy on viral replication (See, e.g., Crute et al., Nature Medicine, 2002, 8:386-391). For example, viral titers by plaque assays are determined from the vaginal swabs. A mouse model of HSV-1 using SKH-1 mice, a strain of immunocompetent hairless mice, to study cutaneous lesions is also described in the art (See, e.g., Crute et al., Nature Medicine, 2002, 8:386-391 and Bolger et al., Antiviral Res., 1997, 35:157-165). Guinea pig models of HSV have also been described, See, e.g., Chen et al., Virol. J, 2004 Nov. 23, 1:11. Statistical analysis is carried out to calculate significance (e.g., a P value of 0.05 or less).

5.3.2.2 HCMV

Since HCMV does not generally infect laboratory animals, mouse models of infection with murine CMV (MCMV) can be used to assay antiviral activity Compounds in vivo. For example, a MCMV mouse model with BALB/c mice can be used to assay the antiviral activities of Compounds in vivo when administered to infected mice (See, e.g., Kern et al., Antimicrob. Agents Chemother., 2004, 48:4745-4753). Tissue homogenates isolated from infected mice treated or untreated with Compounds are tested using standard plaque assays with mouse embryonic fibroblasts (MEFs). Statistical analysis is then carried out to calculate significance (e.g., a P value of 0.05 or less).

Alternatively, human tissue (i.e., retinal tissue or fetal thymus and liver tissue) is implanted into SCID mice, and the mice are subsequently infected with HCMV, preferably at the site of the tissue graft (See, e.g., Kern et al., Antimicrob. Agents Chemother., 2004, 48:4745-4753). The pfu of HCMV used for inoculation can vary depending on the experiment and virus strain. Any appropriate routes of administration (e.g., oral, topical, systemic, nasal), frequency and dose of administration can be tested to determine the optimal dosages and treatment regimens using Compounds, optionally in combination with other therapies. Implant tissue homogenates isolated from infected mice treated or untreated with Compounds at various time points are tested using standard plaque assays with human foreskin fibroblasts (HFFs). Statistical analysis is then carried out to calculate significance (i.e., a P value of 0.05 or less).

Guinea pig models of CMV to study antiviral agents have also been described, See, e.g., Bourne et al., Antiviral Res., 2000, 47:103-109; Bravo et al., Antiviral Res., 2003, 60:41-49; and Bravo et al, J. Infectious Diseases, 2006, 193:591-597.

5.3.2.3 Hepatitis

A HBV transgenic mouse model, lineage 1.3.46 (official designation, Tg[HBV 1.3 genome] Chi46) has been described previously and can be used to test the in vivo antiviral activities of Compounds as well as the dosing and administration regimen (See, e.g., Cavanaugh et al., J. Virol., 1997, 71:3236-3243; and Guidotti et al., J. Virol., 1995, 69:6158-6169). In these HBV transgenic mice, a high level of viral replication occurs in liver parenchymal cells and in the proximal convoluted tubules in the kidneys of these transgenic mice at levels comparable to those observed in the infected liver of patients with chronic HBV hepatitis. HBV transgenic mice that have been matched for age (i.e., 6-10 weeks), sex (i.e., male), and levels of hepatitis B surface antigen (HBsAg) in serum can be treated with Compounds or placebo followed by antiviral activity analysis to assess the antiviral activity of Compounds. Non-limiting examples of assays that can be performed on these mice treated and untreated with Compounds include Southern analysis to measure HBV DNA in the liver, quantitative reverse transcriptase PCR (qRT-PCR) to measure HBV RNA in liver, immunoassays to measure hepatitis e antigen (HBeAg) and HBV surface antigen (HBsAg) in the serum, immunohistochemistry to measure HBV antigens in the liver, and quantitative PCR (qPCR) to measure serum HBV DNA. Gross and microscopic pathological examinations can be performed as needed.

Various hepatitis C virus (HCV) mouse models described in the art can be used in assessing the antiviral activities of Compounds against HCV infection (See Zhu et al., Antimicrobial Agents and Chemother., 2006, 50:3260-3268; Bright et al., Nature, 2005, 436:973-978; Hsu et al., Nat. Biotechnol., 2003, 21:519-525; Ilan et al., J. Infect. Dis. 2002, 185:153-161; Kneteman et al., Hepatology, 2006, 43:1346-1353; Mercer et al., Nat. Med., 2001, 7:927-933; and Wu et al., Gastroenterology, 2005, 128:1416-1423). For example, mice with chimeric human livers are generated by transplanting normal human hepatocytes into SCID mice carrying a plasminogen activator transgene (Alb-uPA) (See Mercer et al., Nat. Med., 2001, 7:927-933). These mice can develop prolonged HCV infections with high viral titers after inoculation with HCV (e.g., from infected human serum). Thus, these mice can be administered a Compound or placebo prior to, concurrently with, or subsequent to HCV infection, and replication of the virus can be confirmed by detection of negative-strand viral RNA in transplanted livers or expression of HCV viral proteins in the transplanted hepatocyte nodules. The statistical significance of the reductions in the viral replication levels is determined.

Another example of a mouse model of HCV involves implantation of the HuH7 cell line expressing a luciferase reporter linked to the HCV subgenome into SCID mice, subcutaneously or directly into the liver (See Zhu et al., Antimicrobial Agents and Chemother., 2006, 50:3260-3268). The mice are treated with a Compound or placebo, and whole-body imaging is used to detect and quantify bioluminescence signal intensity. Mice treated with a Compound that is effective against HCV have less bioluminescence signal intensity relative to mice treated with placebo or a negative control.

5.3.2.4 HIV

The safety and efficacy of Compounds against HIV can be assessed in vivo with established animal models well known in the art. For example, a Trimera mouse model of HIV-1 infection has been developed by reconstituting irradiated normal BALB/c mice with murine SCID bone marrow and engrafted human peripheral blood mononuclear cells (See Ayash-Rashkovsky et al., FASEB J., 2005, 19:1149-1151). These mice are injected intraperitoneally with T- and M-tropic HIV-1 laboratory strains. After HIV infection, rapid loss of human CD4+ T cells, decrease in CD4/CD8 ratio, and increased T cell activation can be observed. A Compound can be administered to these mice and standard assays known in the art can be used to determine the viral replication capacity in animals treated or untreated with a Compound. Non-limiting examples of such assays include the COBAS AMPLICOR® RT-PCR assay (Roche Diagnostics, Branchberg, N.J.) to determine plasma viral load (HIV-1 RNA copies/ml); active HIV-1 virus replication assay where human lymphocytes recovered from infected Trimera mice were cocultured with target T cells (MT-2 cells) and HIV-dependent syncytia formation was examined; and human lymphocytes recovered from infected Trimera mice were cocultured with cMAGI indicator cells, where HIV-1 LTR driven trans-activation of β-galactosidase was measured. Levels of anti-HIV-1 antibodies produced in these mice can also be measured by ELISA.

Other established mouse models described in the art can also be used to test the antiviral activity of Compounds in vivo (See, Mosier et al., Semin. Immunol., 1996, 8:255-262; Mosier et al., Hosp. Pract. (Off Ed)., 1996, 31:41-48, 53-55, 59-60; Bonyhadi et al., Mol. Med. Today, 1997, 3:246-253; Jolicoeur et al., Leukemia, 1999, 13:S78-S80; Browning et al., Proc. Natl. Acad. Sci. USA, 1997, 94:14637-14641; and Sawada et al., J. Exp. Med., 1998, 187:1439-1449). A simian immunodeficiency virus (SIV) nonhuman primate model has also been described (See Schito et al., Curr. HIV Res., 2006, 4:379-386).

5.3.2.5 Influenza Virus Animal Models

Animal models, such as ferret, mouse, guinea pig, and chicken, developed for use to test antiviral agents against influenza virus have been described, See, e.g., Sidwell et al., Antiviral Res., 2000, 48:1-16; Lowen A. C. et al. PNAS., 2006, 103: 9988-92; and McCauley et al., Antiviral Res., 1995, 27:179-186. For mouse models of influenza, non-limiting examples of parameters that can be used to assay antiviral activity of Compounds administered to the influenza-infected mice include pneumonia-associated death, serum $\alpha$1-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

5.3.3 Assays in Humans

In one embodiment, a Compound that modulates replication of a virus is assessed human subjects suffering from such an infection with such a virus. In accordance with this embodiment, a Compound or a control compound (e.g., placebo) is administered to the human subject, and the effect of the Compound on viral replication is determined by, e.g., analyzing the level of the virus or viral nucleic acids in a biological sample (e.g., serum or plasma). A Compound that alters the virus replication can be identified by comparing the level of virus replication in a subject or group of subjects treated with a control compound to that in a subject or group of subjects treated with a the Compound. Alternatively, alterations in viral replication can be identified by comparing the level of the virus replication in a subject or group of subjects before and after the administration of a Compound. Techniques known to those of skill in the art can be used to obtain the biological sample and analyze the mRNA or protein expression.

In another embodiment, the effect of a Compound on the severity of one or more symptoms associated with a virus is assessed in a subject having such a virus infection. In accordance with this embodiment, a Compound or a control compound (e.g., placebo) is administered to a human subject suffering from viral infection and the effect of the Compound on one or more symptoms of the virus infection is determined. A Compound that reduces one or more symptoms can be identified by comparing the subjects treated with a control compound (e.g., placebo) to the subjects treated with the Compound. Techniques known to physicians familiar with infectious diseases can be used to determine whether a Compound reduces one or more symptoms associated with the infectious disease.

5.4 Compositions

Any Compound described herein may optionally be in the form of a composition comprising the Compound and a carrier, excipient or diluent. In certain embodiments provided herein, compositions (including pharmaceutical compositions) comprise a Compound and a pharmaceutically acceptable carrier, excipient, or diluent.

In certain embodiments, provided herein are pharmaceutical compositions comprising an effective amount of a Compound and a pharmaceutically acceptable carrier, excipient, or diluent. In a specific embodiment, the pharmaceutical compositions comprise a Compound that inhibits a virus (e.g., a DNA virus, a positive-sense, single-stranded RNA virus, a negative-sense, single-stranded RNA virus, a double-stranded RNA virus and a retrovirus). The pharmaceutical compositions are suitable for veterinary and/or human administration.

The pharmaceutical compositions provided herein can be in any form that allows for the composition to be administered to a subject, preferably a human.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a specific carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose free compositions can comprise excipients that are well known in the art and are listed, for example, in the U.S. Pharmacopeia (USP) SP (XXI)/NF (XVI). In general, lactose free compositions comprise an active ingredient, a binder/filler, and a lubricant in pharmaceutically compatible and pharmaceutically acceptable amounts. Specific lactose free dosage forms comprise a Compound, microcrystalline cellulose, pre gelatinized starch, and magnesium stearate.

Further provided herein are anhydrous pharmaceutical compositions and dosage forms comprising one or more Compounds, since water can facilitate the degradation of some Compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some Compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions. Compositions and dosage forms that comprise lactose and at least one Compound that comprises a primary or secondary amine are preferably anhydrous if substantial contact with moisture and/or humidity during manufacturing, packaging, and/or storage is expected.

An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are compositions and dosage forms that comprise one or more agents that reduce the rate by which a Compound will decompose. Such agents, which are referred to herein as "stabilizers," include, but are not limited to, antioxidants such as ascorbic acid, pH buffers, or salt buffers.

The compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain an effective amount of a Compound preferably in purified form, together with a suitable amount of carrier so as to provide the form for proper administration to the patient. The formulation should suit the mode of administration. In a specific embodiment, the compositions or single unit dosage forms are sterile and in suitable form for administration to a subject, preferably an animal subject, more preferably a mammalian subject, and most preferably a human subject.

Compositions provided herein are formulated to be compatible with the intended route of administration. Examples of routes of administration include, but are not limited to, parenteral, e.g., intravenous, intradermal, subcutaneous, oral (e.g., inhalation), intranasal, transdermal (topical), transmucosal, intra-synovial and rectal administration. In a specific embodiment, the composition is formulated in accordance with routine procedures as a composition adapted for intravenous, subcutaneous, intramuscular, oral, intranasal or topical administration to human beings. In a specific embodiment, a composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non aqueous liquid suspensions, oil in water emulsions, or a water in oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms will typically vary depending on their use.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms provided herein are prepared by combining a Compound in an intimate admixture with at least one excipient according to conventional pharmaceutical Compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered Compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A Compound can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients described herein. The Composition thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased patient compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or agents.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Agents that increase the solubility of one or more of the Compounds provided herein can also be incorporated into the parenteral dosage forms provided herein.

Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms provided herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with a Compound. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more Compounds. Similarly, the polarity of a solvent carrier, its ionic strength, or tonicity can be adjusted to improve delivery. Agents such as stearates can also be added to pharmaceutical compositions or dosage forms to advantageously alter the hydrophilicity or lipophilicity of one or more Compounds so as to improve delivery. In this regard, stearates can serve as a lipid vehicle for the formulation, as an emulsifying agent or surfactant, and as a delivery enhancing or penetration enhancing agent. Different salts, hydrates or solvates of the Compounds can be used to further adjust the properties of the resulting composition.

In certain specific embodiments, the compositions are in oral, injectable, or transdermal dosage forms. In one specific embodiment, the compositions are in oral dosage forms. In another specific embodiment, the compositions are in the form of injectable dosage forms. In another specific embodiment, the compositions are in the form of transdermal dosage forms.

5.5 Prophylactic and Therapeutic Uses of Antiviral Compounds

Described herein are methods for inhibiting replication of a virus utilizing a Compound. In a specific embodiment, a method for inhibiting replication of a virus comprises contacting a composition comprising a cell infected with a virus. In another embodiment, a method for inhibiting replication of a virus comprises: (i) contacting a cell that permits replication of the virus with a Compound; and (ii) infecting the cell with the virus. In another embodiment, a method for inhibiting replication of a virus comprises: (i) infecting a cell with a virus, wherein the cell permits replication of a virus; and (ii) contacting the infected cell with a Compound. In certain embodiments, the cell is infected with a virus, concurrently or within, for example, 5 seconds, 15 seconds, 30 seconds, 1 minute, 5 minutes, 15 minutes, 30 minutes, 1 hour, 2 hours, 6 hours, 12 hours, 16 hours or 24 hours of contacting with the Compound. In certain embodiments, the Compound has the formula A3-H, A3-I, A3-J, including, but not limited to, a Compound with the formula A3, A3-1, A3-2, A3-4, A3-5, A3-6, A3-7, A3-8, A3-9, A3-11, or A3-12. In some embodiments, the Compound has the formula A3-J, including, but not limited to, a Compound with the formula A3-1, A3-7, A3-8, A3-9, A3-11, or A3-12. In certain specific embodiments, the Compound has a formula A3-2 or A3-5. In certain embodiments, the virus is a negative-sense, single-stranded DNA virus. In other embodiments, the virus is not a negative-sense, single-stranded RNA virus. In some embodiments, the virus is a DNA virus, double-stranded RNA virus, positive-sense, single-stranded RNA virus, negative-sense, single-stranded RNA virus or retrovirus. In certain embodiments, the virus is not Sendai virus, Vesicular Stomatitis virus, HIV, adenovirus, influenza virus (e.g., influenza A), Newcastle disease virus, West Nile virus, and/or Dengue virus.

In certain embodiments, described herein are methods for inhibiting replication of a DNA virus, double-stranded RNA virus, positive-sense, single-stranded RNA virus, or retrovirus, in a subject comprising administering a Compound or composition thereof to the subject. In a specific embodiment, the Compound is administered to a subject infected with the virus. In another embodiment, the Compound has the formula A3-H, A3-I, or A3-J, such as a Compound with the formula A3, A3-1, A3-2, A3-3, A3-4, A3-5, A3-6, A3-7, A3-8, A3-9, A3-11, or A3-12. In certain specific embodiments, the Compound has a formula A3-2 or A3-5.

In certain embodiments, described herein are methods for inhibiting replication of a virus (e.g., a DNA virus, double-stranded RNA virus, positive-sense, single-stranded RNA virus, negative-sense, single-stranded RNA virus or retrovirus) in a subject, comprising administering a Compound or composition thereof to the subject. In a specific embodiment, the Compound or composition thereof is administered to a subject infected with the virus. In another embodiment, the Compound has the formula A3-J, A3-1, A3-7, A3-8, A3-9, A3-11 or A3-12. In certain specific embodiments, the Compound has a formula A3-2 and/or A3-5. In certain embodiments, the Compound does not have the formula A3-11 and/or A3-8. In certain embodiments, the Compound does not have the formula A3-J. In certain embodiments, the Compound is not A3-1, A3-7, A3-8, A3-9, A3-11, and/or A3-12. In certain specific embodiments, the Compound does not have the formula A3-2 and/or A3-5. In certain embodiments, the virus is not Sendai virus, Vesicular Stomatitis virus, HIV virus, adenovirus, influenza virus (e.g., influenza A virus), Newcastle disease virus, West Nile virus, Dengue virus, Vaccinia virus, Sindbis virus and/or HCV.

In certain embodiments, described herein are methods for inhibiting replication of a negative-sense, single-stranded RNA virus, in a subject comprising administering a Compound to the subject. In a specific embodiment, the Compound is administered to a subject infected with the virus. In another embodiment, the Compound has the formula A3-J, A3-1, A3-7, A3-8, A3-9, A3-11 or A3-12. In certain specific embodiments, the Compound has a formula A3-2 and/or A3-5. In certain embodiments, the Compound does not have the formula A3-8 and/or A3-11. In certain embodiments, the Compound does not have the formula A3-J. In certain embodiments, the Compound is not A3-1, A3-7, A3-8, A3-9, A3-11, and/or A3-12. In certain embodiments, the virus is not influenza, Newcastle virus, Sendai virus, Vesicular Stomatitis virus.

Described herein are methods of preventing, treating and/or managing a virus infection or the pathological state resulting therefrom (e.g., a DNA virus, a double-stranded RNA virus, a positive-sense, single-stranded RNA virus, a negative-sense, single-stranded RNA virus, or a retroviral infection), said methods comprising administering to a subject in need thereof one or more Compounds or a composition thereof. A Compound may be used as any line of therapy (e.g., a first, second, third, fourth or fifth line therapy) for a virus infection or the pathological state resulting therefrom (e.g., a DNA virus, a double-stranded RNA virus, a positive-sense, single-stranded RNA virus, a negative-sense, single-stranded RNA virus, or a retroviral infection). In certain embodiments, the virus is not Sendai virus, Vesicular Stomatitis virus, HIV virus, adenovirus, influenza virus (e.g., influenza A), Newcastle disease virus, West Nile virus, Dengue virus, vaccinia virus, Sindbis virus and/or HCV. In specific embodiments, the Compound has the formula A3-J, including a Compound with the formula A3-1, A3-7, A3-8, A3-9, A3-11 or A3-12. In certain specific embodiments, the Compound has a formula A3-2 and/or A3-5. In certain embodiments, the Compound is not A3-8 and/or A3-11. In certain embodiments, the Compound is not A3-1, A3-7, A3-8, A3-9, A3-11, and/or A3-12. In certain embodiments, the Compound is not A3J. In certain specific embodiments, the Compound is not A3-2 and/or A3-5.

In certain embodiments, provided herein is a method of preventing a viral infection or the pathological state resulting therefrom (e.g., a DNA virus, double-stranded RNA virus, positive-sense, single-stranded RNA virus, negative-sense, single-stranded RNA virus, or retrovirus infection), said method comprising administering to a subject in need thereof an effective amount of one or more Compounds. In a specific embodiment, provided herein is a method of preventing a DNA virus, a double-stranded RNA virus, a positive-sense, single-stranded RNA virus, or a retrovirus infection, said method comprising administering to a subject in need thereof an effective amount of one or more Compounds or a composition thereof. A Compound may be used as any line of therapy (e.g., a first, second, third, fourth or fifth line therapy) for a DNA virus, a double-stranded RNA virus, a positive-sense, single-stranded RNA virus, or a retrovirus infection. In certain embodiments, the virus is not Sendai virus, Vesicular Stomatitis virus, HIV virus, adenovirus, influenza virus (e.g., influenza A virus), Newcastle virus, West Nile and/or Dengue virus. In specific embodiments, the Compound has the formula A3-H, A3-I, or A3-J, including a Compound with the formula, A3, A3-1, A3-2, A3-3, A3-4, A3-5, A3-6, A3-7, A3-8, A3-9, A3-11 or A3-12. In certain specific embodiments, the Compound has a formula A3-2 and/or A3-5. In certain embodiments, the Compound is AH, A1, A3, A3-2, A3-3, A3-4, A3-5, A3-6. In certain embodiments, the Compound is not A3-8 and/or A3-11. In certain embodiments, the Compound is not A3-J. In certain embodiments, the Compound is not A3-1, A3-7, A3-8, A3-9, A3-11 or A3-12. In certain specific embodiments, the Compound is not A3-2 and/or A3-5.

In certain embodiments, described herein are methods of preventing viral infection or the pathological state resulting therefrom, of a negative-sense, single-stranded RNA virus infection, said methods comprising administering to a subject in need thereof an effective amount of one or more Compounds or composition thereof. In certain embodiments, the Compound has the formula A3-J, including a Compound with the formula, A3-1, A3-7, A3-8, A3-9, A3-11 or A3-12. In certain specific embodiments, the Compound has a formula A3-2 and/or A3-5. In certain embodiments, the Compound does not have the formula A3-8 and/or A3-11 compound. In certain embodiments, the Compound is not A3-1, A3-7, A3-8, A3-9, A3-11 and/or A3-12. In certain specific embodiments, the Compound is not A3-2 and/or A3-5. In certain embodiments, the Compound is not A3J. In certain embodiments, the virus is not influenza virus (e.g., influenza A), Newcastle disease virus, Sendai virus, Vesicular Stomatitis virus. A Compound may be used as any line of therapy (e.g., a first, second, third, fourth or fifth line therapy) for a negative-sense, single-stranded RNA virus infection.

In certain embodiments, described herein are methods of treating and/or managing a viral infection or the pathological state resulting therefrom, said methods comprising administering to a subject in need thereof one or more Compounds or a composition thereof. In a specific embodiment, provided herein is a method of treating and/or managing viral infection or the pathological state resulting therefrom, said method comprising administering to a subject in need thereof an effective amount of one or more Compounds or composition thereof. A Compound may be used as any line of therapy (e.g., a first, second, third, fourth or fifth line therapy) for a viral infection or the pathological state resulting therefrom. In specific embodiments, the Compound has the formula A3-J, including a Compound with the formula A3-2, A3-7, A3-8, A3-9, A3-11 or A3-12. In certain specific embodiments, the Compound has a formula A3-2 and/or A3-5. In specific embodiments, the Compound is not A3-8 and/or A3-11. In certain embodiments, the Compound is not A3-1, A3-7, A3-8, A3-9, A3-11 and/or A3-12. In certain specific embodiments, the Compound is not A3-2 and/or A3-5. In certain embodiments, the Compound is not A3J. In certain embodiments, the virus is not Sendai virus, Vesicular Stomatitis virus, HIV, adenovirus, influenza virus (e.g., influenza A), Newcastle disease virus, West Nile virus, Dengue virus, vaccinia virus, Sindbis virus and/or HCV.

In certain embodiments, described herein are methods of treating and/or managing a DNA virus, a double-stranded RNA virus, a positive-sense, single-stranded RNA virus, or a retroviral infection or the pathological state resulting therefrom, said methods comprising administering to a subject in need thereof one or more Compounds or a composition thereof. In a specific embodiment, provided herein is a method of treating and/or managing a DNA virus, a double-stranded RNA virus, a positive-sense, single-stranded RNA virus, or a retroviral infection or the pathological state resulting therefrom, said method comprising administering to a subject in need thereof an effective amount of one or more Compound. The Compound may be used as any line of therapy (e.g., a first, second, third, fourth or fifth line therapy) for a DNA virus, a double-stranded RNA virus, a positive-sense, single-stranded RNA virus, a retroviral infection or the pathological state resulting therefrom. In certain embodiments, the virus is not HIV, adenovirus, influenza virus (e.g., influenza A), West Nile virus, Dengue virus, HCV virus and/or adenovirus. In specific embodiments, the Compound with the formula A3-H, A3-I, or A3-J, including a Compound with the formula A3, A-3-1, A3-2, A3-3, A3-4, A3-5, A3-6, A3-7, A3-8, A3-9, A3-11 or A3-12. In certain specific embodiments, the Compound has a formula A3-2 or A3-5. In certain embodiments, the Compound has the formula AH, AI, AJ, A3, A3-2, A3-3, A3-4, A3-5, A3-6.

In certain embodiments, described herein are methods of treating and/or managing a negative-sense, single-stranded RNA virus infection or the pathological state resulting therefrom, said methods comprising administering to a subject in need thereof one or more Compounds having the formula A3-J, including a Compound with the formula A3-2, A3-7, A3-8, A3-9, A3-11 or A3-12, or a composition thereof. In certain specific embodiments, the Compound has a formula A3-2 and/or A3-5 or a composition thereof. In a specific embodiment, provided herein is a method of treating and/or managing a negative-sense, single-stranded RNA virus or the pathological state resulting therefrom, said method comprising administering to a subject in need thereof an effective amount of one or more Compound or a composition thereof. In certain embodiments, the Compound is not A3-8 and/or A3-11. In certain embodiments, the Compound is not A3-1, A3-7, A3-8, A3-9, A3-11, and/or A3-12. In certain specific embodiments, the Compound has a formula A3-2 and/or A3-5. In certain embodiments, the Compound is not A3-J. In certain embodiments, the virus is not influenza virus (e.g., influenza A), Newcastle disease virus, Sendai virus, or Vesicular Stomatitis virus. A Compound may be used as any line of therapy (e.g., a first, second, third, fourth or fifth line therapy) for a negative-sense, single-stranded RNA virus infection or the pathological state resulting therefrom.

In specific embodiments, a Compound is the only active ingredient administered to prevent, treat and/or manage a virus infection or the pathological state resulting therefrom (e.g., a DNA virus, a double-stranded RNA virus, a positive-sense, single-stranded RNA virus, a negative-sense, single-stranded RNA virus, or a retrovirus infection). In a certain embodiment, a Compound is the only active ingredient in a composition that is administered to prevent, treat and/or manage a virus infection or the pathological state resulting therefrom (e.g., a DNA virus, a double-stranded RNA virus, a positive-sense, single-stranded RNA virus, a negative-sense, single-stranded RNA virus, or a retroviral infection). In other embodiments, more than one Compound is administered in order to achieve a synergistic effect.

In some embodiments, a Compound specifically interferes with the replication of a DNA virus, a double-stranded RNA virus, a positive-sense, single-stranded RNA virus, a negative-sense, single-stranded RNA virus, or a retrovirus. In other embodiments, a Compound interferes with the replication of one or more of the following viruses. DNA viruses, double-stranded RNA viruses, positive-sense, single-stranded RNA viruses, negative-sense, single-stranded RNA viruses, or retroviruses. In certain embodiments, the virus is a double-stranded DNA virus. Double-stranded DNA virus includes nuclear double-stranded DNA virus and cytoplasmic double-stranded DNA virus. Nuclear double-stranded DNA virus includes the herpesvirus family, polyomavirus family, papillomavirus family, and adenovirus family. Cytoplasmic double-stranded DNA virus includes the poxvirus family. Single-stranded DNA virus includes the parvovirus family and the circovirus family. Certain DNA virus has a genome that is partially double-stranded and partially single stranded circular DNA, which includes the hepadnaviruses. Double-stranded RNA virus includes the reovirus family and the birnavirus family. Positive-sense, single-stranded RNA virus includes the flavivirus family, the togavirus family, the coronavirus family, the calicivirus family, the picornavirus family, and the retrovirus family. The Arenavirus family is a negative-sense, single-stranded RNA virus which has a genome that is segmented as denoted as L and S. Both the L and S segments are circular but the L strand is negative sense and the S strand is ambisense.

The Compound may interfere with the replication of one or more of the following non-segmented negative-sense, single-stranded RNA viruses: a rhabdovirus (e.g., Vesicular Stomatitis virus (VSV) or a rabies or rabies-related virus), a paramyxovirus (e.g., Newcastle Disease Virus (NDV), measles virus, mumps virus, a parainfluenza virus such as Sendai virus, or a pneumovirus such as respiratory syncytial virus (RSV) or metapneumovirus), filovirus (e.g., Ebola virus or Marburg virus), hepatitis delta virus, or bornavirus. The Compound may interfere with the replication of one or more of the following segmented, negative-sense, single-stranded RNA viruses: an orthomyxovirus (e.g., influenza A virus, influenza B virus, influenza C virus, thogoto virus, or infectious salmon anemia virus), a bunyavirus (e.g., a bunyamwera virus, Hantaan virus, Dugbe virus, Rift Valley fever virus, or tomato spotted wilt virus), or an arenavirus (e.g., lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Tacaribe virus, and Tamiami virus.

In a specific embodiment, the negative-sense, single-stranded RNA virus is an enveloped virus. In another specific embodiment, the negative-sense, single-stranded RNA virus is a influenza virus (e.g., an influenza A virus, influenza B virus or influenza C virus). In one embodiment, the influenza A virus is an H5N1 isolate. In another embodiment, the influenza A virus is an H1N1 isolate. In another embodiment, the negative-sense, single-stranded RNA virus is a parainfluenza virus, a measles virus, a mumps virus or a respiratory syncytial virus (RSV). In one embodiment, the parainfluenza virus is Sendai virus. In one embodiment, the parainfluenza virus is a human parainfluenza virus (HPIV). In specific embodiments the HPIV is HPIV type 2 (HPIV-2), HPIV type 3 (HPIV-3), or HPIV type 4 (HPIV-4). In one embodiment, the HPIV-4 is subtype A. In another embodiment, the HPIV-4 is subtype B. In a specific embodiment, the negative-sense, single-stranded RNA virus is NDV. In a specific embodiment, the negative-sense, single-stranded RNA virus is VSV. In certain embodiments, the negative-sense, single-stranded RNA virus is not a rhabdovirus. In certain embodiments, the negative-sense, single-stranded RNA virus is not VSV.

In some embodiments, a Compound reduces the viral replication of one type, subtype or strain of a virus (e.g., a DNA virus, a double-stranded RNA virus, a positive-sense, single-stranded RNA virus, a negative-sense, single-stranded RNA virus, or a retrovirus) more than another. For example, a Compound may reduce the replication of an influenza A virus more than it reduces the replication of an influenza B virus, and vice versa.

The choice of Compounds to be used depends on a number of factors, including but not limited to the type of viral infection, health and age of the patient, and toxicity or side effects.

In some embodiments, a Compound or a composition thereof is administered to a subject to prevent, treat and/or manage a viral infection or the pathological state resulting therefrom for which no antiviral therapy is available. In other embodiments, a Compound or a composition thereof is administered to a subject to prevent, treat and/or manage a viral infection or the pathological state resulting therefrom as an alternative to other conventional therapies.

In some embodiments, a Compound or composition thereof and one or more other therapies (e.g., prophylactic or therapeutic agents) are administered to a subject to prevent, treat and/or manage a viral infection or the pathological state resulting therefrom. In a specific embodiment, the other therapies are currently being used, have been used or are known to be useful in the prevention of a symptom of viral infection, treatment and/or management of a viral infection or the pathological state resulting therefrom. Non-limiting examples of such therapies are provided in Section 5.8, infra. In a specific embodiment, one or more Compounds are administered to a subject in combination with one or more of the therapies described in Section 5.8, infra. In another embodiment, one or more Compounds are administered to a subject in combination with a supportive therapy, a pain relief therapy, or another therapy that does not have antiviral activity.

The combination therapies described herein can be administered sequentially or concurrently. In one embodiment, the combination therapies comprise a Compound and at least one other therapy which has the same mechanism of action. In another embodiment, the combination therapies comprise a Compound and at least one other therapy which has a different mechanism of action than the Compound.

In a specific embodiment, the combination therapies described herein improve the prophylactic and/or therapeutic effect of the Compound by functioning together with another Compound to have an additive or synergistic effect. In another embodiment, the combination therapies reduce the side effects associated with each therapy taken alone.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In specific embodiments, the Compounds utilized for administration to a subject as an antiviral Compounds have low cytotoxicity and high safety profile. Such cytotoxicity and safety can be determined using the methods that are known in the art and are described in Section 5.3.2.8 and Section 7.

In certain embodiments, a Compound or a composition thereof can be used to inhibit/reduce a viral infection in a plant(s). In certain embodiments, described herein are methods of preventing, treating, or managing a viral infection in a plant comprising exposing the plant to a Compound or a composition thereof. In specific embodiment, a Compound or a composition thereof is sprayed directly onto the plant or mixed in with the soil. In specific embodiment, a Compound or a composition thereof reduces the death or illnesses of a plant(s) that is/are associated with or caused by a viral infection. In specific embodiments, the plant is a flowering plant, crop, tobacco, cotton, corn, vegetable, wheat, rice, barley, grass, or fruit trees. In specific embodiments, the plant virus is tobacco mosaic virus and cauliflower mosaic virus.

5.5.1 Viruses

Provided herein are Compounds for use in the prevention of a viral infection (e.g., prevention of a symptom of a viral infection), management and/or treatment of viral infection or the pathological state resulting therefrom. The antiviral activity of Compounds against any virus can be tested using techniques described in Section 5.2.1 Supra. The virus may have a DNA or RNA genome, have a double-stranded or single-stranded genome, enveloped or naked. See, e.g., FIG. 1 modified from Flint et al., Principles of Virology: Molecular Biology, Pathogenesis and Control of Animal Viruses. 2nd edition, ASM Press, 2003, for a subset of virus families and their classifications, as well as a subset of viruses against which Compounds can be assessed for antiviral activity. In specific embodiments, the virus infects primates. In specific embodiments, the virus infects human. In other embodiments, the virus infects non-human animals. In a specific embodiment, the virus infects pigs, fowl, other livestock, or pets (e.g., cats, dogs, etc.).

In certain embodiments, the virus is a DNA virus. In other embodiments, the virus is a RNA virus. In one embodiment, the virus is a DNA or a RNA virus with a single-stranded genome. In another embodiment, the virus is a DNA or a RNA virus with a double-stranded genome.

In some embodiments, the virus has a linear genome. In other embodiments, the virus has a circular genome. In some embodiments, the virus has a segmented genome. In other embodiments, the virus has a non-segmented genome.

In some embodiments, the virus is a positive-sense RNA virus. In other embodiments, the virus is a negative-sense RNA virus. In one embodiment, the virus is a segmented, positive-sense RNA virus. In another embodiment, the virus is a non-segmented positive-sense RNA virus.

In some embodiments, the virus is an icosahedral virus. In other embodiments, the virus is a helical virus. In yet other embodiments, the virus is a complex virus.

Viruses can be classified into seven classes according to their genome and replication strategies (Baltimore Class I, II, III, IV, V, VI, and VII) (Baltimore, 1971, Bacteriol. Rev. 35(5): 235-241) (Dimmock et al., "Introduction to Modern Virology, $6^{th}$ edition." Blackwell Publishing 2007) as indicated below.

Class I: Double-Stranded DNA Virus

There are two type of viruses in this class. The first type is the more common and is known as nuclear double-stranded DNA virus. It usually must enter the host nucleus in order to replicate and utilizes the host cell polymerases for replication. Thus this type of virus is highly dependent on the cell cycle of the host and will replicate when the cell's polymerases are active. An example of a family within this classification is the Adenoviridae. The second type is known as cytoplasmic double-stranded DNA virus which replicates in the cytoplasm of the host cell. The DNA polymerase and DNA-dependent RNA polymerases are encoded by the virus. An example for this class of virus is the Poxvirus family.

Class II: Single-Stranded DNA Virus

This class of virus replicates within the nucleus and form a double-stranded DNA intermediate during replication Examples include the Circoviridae family and the Parvoviridae family Class III: Double-Stranded RNA Virus Like most viruses with RNA genomes, double-stranded RNA virus does not rely on host polymerases for replication to the extent that viruses with DNA genomes do. The RNA-dependent RNA polymerase is encoded by the virus. This class includes the Reoviridae family and the Birnaviridae family.

Class IV: Positive-Sense, Single-Stranded RNA Virus

For this class of virus, replication is primarily in the cytoplasm of the host and is less dependent on the cell cycle of the host as DNA viruses. All of the viral proteins can be formed directly from the viral genome using the host ribosomes. Viruses have polycistronic mRNA where the genome RNA forms the mRNA and is translated into a polyprotein product that is subsequently cleaved to form the mature proteins. The gene can utilize a few methods in which to produce proteins from the same strand of RNA, all in the sake of reducing the size of its gene. This class of virus has complex transcription, for which subgenomic mRNAs, ribosomal frameshifting and proteolytic processing of polyproteins may be used. All of which are different mechanisms with which to produce proteins from the same strand of RNA. Examples of this class include the Coronaviridae family, the Flaviviridae family and the Picornaviridae family.

Class V: Negative-Sense, Single-Stranded RNA

For this class of virus, replication is less dependent on the cell cycle of the host as DNA viruses. All the genes are negative-sense and cannot be directly accessed by host polymerase to immediately form proteins. Instead, the genes are transcribed by viral RNA-dependent RNA polymerase into a positive-sense RNA. This class can be divided into two groups: Virus containing non-segmented genomes and segmented genomes. For virus containing non-segmented genome, replication begins with transcription from the negative-sense genome using the viral RNA-dependent RNA polymerase to yield monocistronic mRNAs that code for the various viral proteins. A positive-sense genome copy is then serves as a template for production of the negative-sense genome. Replication occurs in the cytoplasm. Unlike the non-segmented negative-sense, single-stranded RNA virus, replication of the segmented negative-sense, single-stranded RNA virus occurs in the nucleus. The viral RNA-dependent RNA polymerase produces monocistronic mRNAs from each genome segment. Examples in this class include the orthomyxoviridae family, the paramyxoviridae family, the bunyaviridae family, the filoviridae family, the rhabdoviridae family, and the arenaviridae family.

Class VI: Positive-Sense, Single-Stranded RNA Virus that Replicates Through a DNA Intermediate One defining feature of this class of virus is the use of reverse transcriptase to convert the positive-sense RNA into DNA. Instead of using the RNA for templates of proteins, this class of virus uses DNA to create the templates, which is spliced into the host genome using integrase. Replication can then commence with the help of the polymerase of the host cell. A well studied family of this class of virus include the retrovirus family. A well studied example includes HIV.

Class VII: Double-Stranded DNA Virus that Replicates Through a Single-Stranded RNA Intermediate This class of virus has a double-stranded, gapped genome that is subsequently filled in to form a covalently closed circle (ccc DNA) that serves as a template for production of viral mRNAs and a subgenomic RNA. The pregenome RNA serves as a template for the viral reverse transcriptase and for production of the DNA genome. An example of this class is the hepadnavirus family.

Provided herein are Compounds for use in the inhibition of viral replication (e.g., prevention of a symptom of viral replication), management and/or treatment of viral replication or the pathological state resulting therefrom. In certain embodiments, a Compound has a formula of A3-H, A3-I, A3-J, including a Compound with the formula A3, A3-1, A3-2, A3-3, A3-4, A3-5, A3-6, A3-7, A3-8, A3-9, A3-11, or A3.12 can be used to inhibiting the viral replication (e.g., prevention of a symptom of a viral replication), management and/or treatment of viral replication or the pathological state resulting therefrom. In certain embodiments, the virus is a double-stranded DNA virus. Double-stranded DNA virus includes nuclear double-stranded DNA virus and cytoplasmic double-stranded DNA virus. Nuclear double-stranded DNA virus includes the herpesvirus family, polyomavirus family, papillomavirus family, and adenovirus family. Cytoplasmic double-stranded DNA virus includes the poxvirus family. Single-stranded DNA virus includes the parvovirus family and the circovirus family. Certain DNA virus has a genome that is partially double-stranded and partially single-stranded circular DNA, which includes the hepadnaviruses. Double-stranded RNA virus includes the reovirus family and the birnavirus family. Positive-sense, single-stranded RNA virus includes the flavivirus family, the togavirus family, the coronavirus family, the calicivirus family, the picornavirus family, and the retrovirus family. Non-limiting examples of the hepadnavirus family (hepadnaviridae) includes hepatitis B virus (HBV), woodchuck hepatitis virus, ground squirrel hepatitis virus, duck hepatitis B virus, heron hepatitis B virus. Non-limiting examples of the herpesvirus family (herpesviridae) includes herpes simplex virus (HSV) types 1 and 2, varicella-zoster virus, cytomegalovirus (CMV), human cytomegalovirus (HCMV), Epstein-Barr virus (EBV), human herpesvirus 6 (variants A and B), human herpesvirus 7, and Kaposi's sarcoma-associated herpes virus (KSHV). Non-limiting examples of the poxvirus (poxyiridae) family includes vaccinia virus, variola virus, smallpox virus, monkeypox virus, cowpox virus, camelpox virus, mousepox virus, raccoonpox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, and Yabapox virus. Non-limiting examples of the flavivirus family (flaviviridae) includes Dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, and Kyasanur Forest disease virus. Non-limiting examples of the togavirus family (togaviridae) includes Venezuelan equine encephalitis virus, chikungunya virus, Ross River virus, Mayaro virus, Sindbis virus, and rubella virus. Non-limiting examples of the retrovirus family (retroviridae) includes human immunodeficiency virus (HIV) types 1 and 2, human T cell leukemia virus (HTLV) types 1, 2, and 5, and mouse mammary tumor virus (MMTV). Non-limiting examples of the coronavirus family (coronaviridae) includes severe acute respiratory syndrome (SARS) virus Non-limiting examples of the parvovirus family (parvoviridae) includes canine parvovirus, and parvovirus B19. Non-limiting examples of the circovirus family (circoviridae) includes porcine circovirus type 1 and 2, BFDV (Beak and Feather Disease Virus), and chicken anaemia virus. Non-limiting examples of the polyomavirus family (Polyomaviridae) includes simian virus 40 (SV40), JC virus, BK virus, and Budgerigar fledgling disease virus. Non-limiting examples of the papillomavirus family (papillomaviridae) includes human papillomavirus, and bovine papillomavirus (BPV) type 1. Non-limiting examples of the Adenovirus family (Adenoviridae) includes human adenovirus (HAdV-A, HAdV-B, HAdV-C, HAdV-D, HAdV-E, and HAdV-F), fowl adenovirus A, ovine adenovirus D, and frog adenovirus. Non-limiting examples of the reovirus family (reoviridae) includes human orbivirus, human coltivirus, mammalian orthoreovirus, bluetongue virus, rotavirus A, Colorado tick fever virus, aquareovirus A, cypovirus 1, Fiji disease virus, rice dwarf virus, rice ragged stunt virus, idnoreovirus 1, and mycoreovirus 1. Non-limiting examples of the birnavirus family (birnaviridae) includes bursal disease virus, and pancreatic necrosis virus. Non-limiting examples of the calicivirus family (caliciviridae) includes swine vesicular exanthema virus, rabbit hemorrhagic disease virus, Norwalk virus, and Sapporo virus. Non-limiting examples of the picornavirus family (picornaviridae) includes human polioviruses (1-3), human coxsackieviruses A1-22, 24 (CA1-22 and CA24, CA23=echovirus 9), human coxsackieviruses (B1-6 (CB1-6), human echoviruses 1-7,9, 11-27, 29-33, vilyuish virus, simian enteroviruses 1-18 (SEV1-18), porcine enteroviruses 1-11 (PEV1-11), and bovine enteroviruses 1-2 (BEV1-2). In certain embodiments, the virus is a human adenovirus, e.g., HAdV-A, HAdV-B, HAdV-C, HAdV-D, HAdV-E, and HAdV-F. In other embodiments, the virus is not a human adenovirus. In a specific embodiment, the virus is vaccinia virus. In an alternative embodiment, the virus is not vaccinia virus. In another embodiment, the virus is Dengue virus. In a further alternative embodiment, the virus is not Dengue virus. In another embodiment, the virus is a hepatitis C virus. In an alternative embodiment, the virus is not a hepatitis C virus. In another embodiment, the virus is a West Nile virus. In an alternate embodiment, the virus is not a West Nile virus. In another embodiment, the virus is a Sindbis virus. In a further alternative embodiment, the virus is not a Sindbis virus. In another specific embodiment, the virus is a human immunodeficiency (HIV) virus. In an alternative embodiment, the virus is not a human immunodeficiency (HIV) virus. In some embodiments, the virus is HIV type 1 virus. In other embodiments, the virus is not HIV type 1 virus.

In certain embodiments, the viral infection is from a negative-sense, single-stranded RNA virus. In certain embodiments, the negative-sense, single-stranded RNA virus includes the filovirus family, rhabdovirus family, bunyavirus family, orthomyxovirus family, paramyxovirus family and Arenavirus family. Non-limiting examples of the filovirus family (filoviridae) includes Ebola virus, and Marburg virus. Non-limiting examples of the rhabdovirus family (rhabdoviridae) includes rabies virus and Vesicular Stomatitis virus. Non-limiting examples of the bunyavirus family (bunyaviridae) includes Crimean-Congo hemorrhagic fever virus, La Crosse virus, and Hantaan virus. Non-limiting examples of the orthomyxovirus family (orthomyxoviridae) includes influenza virus types A, B, and C. Non-limiting examples of the paramyxovirus family (paramyxoviridae) includes parainfluenza virus, respiratory syncytial virus, measles virus, Newcastle disease virus, Sendai virus, and mumps virus. Non-limiting examples of the arenavirus (arenaviridae) includes lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Tacaribe virus, and Tamiami virus. In certain embodiments, the virus is not a filovirus. In another alternative embodiment, the virus is not a rhabdovirus. In a specific embodiment, the virus is not orthomyxovirus. In some embodiments, the virus is not paramyxovirus. In some alternative embodiments, the virus is not an influenza A virus. In certain embodiments, the virus is not an influenza B virus. In certain embodiments, the virus is not a disease virus. In one embodiment, the virus is a not a Sendai virus. In other embodiments, the virus is not a Vesicular Stomatitis virus.

In some embodiments, the virus achieves peak titer in cell culture or a subject in 4 hours or less, 6 hours or less, 8 hours or less, 12 hours or less, 16 hours or less, or 24 hours or less. In other embodiments, the virus achieves peak titers in cell culture or a subject in 48 hours or less, 72 hours or less, or 1 week or less. In other embodiments, the virus achieves peak titers after about more than 1 week. In accordance with these embodiments, the viral titer may be measured in the infected tissue or serum.

In some embodiments, the virus achieves in cell culture a viral titer of $10^4$ pfu/ml or more, $5 \times 10^4$ pfu/ml or more, $10^5$ pfu/ml or more, $5 \times 10^5$ pfu/ml or more, $10^6$ pfu/ml or more, $5 \times 10^6$ pfu/ml or more, $10^7$ pfu/ml or more, $5 \times 10^7$ pfu/ml or more, $10^8$ pfu/ml or more, $5 \times 10^8$ pfu/ml or more, $10^9$ pfu/ml or more, $5 \times 10^9$ pfu/ml or more, or $10^{10}$ pfu/ml or more. In certain embodiments, the virus achieves in cell culture a viral titer of $10^4$ pfu/ml or more, $5 \times 10^4$ pfu/ml or more, $10^5$ pfu/ml or more, $5 \times 10^5$ pfu/ml or more, $10^6$ pfu/ml or more, $5 \times 10^6$ pfu/ml or more, $10^7$ pfu/ml or more, $5 \times 10^7$ pfu/ml or more, $10^8$ pfu/ml or more, $5 \times 10^8$ pfu/ml or more, $10^9$ pfu/ml or more, $5 \times 10^9$ pfu/ml or more, or $10^{10}$ pfu/ml or more within 4 hours, 6 hours, 8 hours, 12 hours, 16 hours, or 24 hours or less. In other embodiments, the virus achieves in cell culture a viral titer of $10^4$ pfu/ml or more, $5 \times 10^4$ pfu/ml or more, $10^5$ pfu/ml or more, $5 \times 10^5$ pfu/ml or more, $10^6$ pfu/ml or more, $5 \times 10^6$ pfu/ml or more, $10^7$ pfu/ml or more, $5 \times 10^7$ pfu/ml or more, $10^8$ pfu/ml or more, $5 \times 10^8$ pfu/ml or more, $10^9$ pfu/ml or more, $5 \times 10^9$ pfu/ml or more, or $10^{10}$ pfu/ml or more within 48 hours, 72 hours, or 1 week.

In some embodiments, the virus achieves a viral yield of 1 pfu/ml or more, 10 pfu/ml or more, $5 \times 10^1$ pfu/ml or more, $10^2$ pfu/ml or more, $5 \times 10^2$ pfu/ml or more, $10^3$ pfu/ml or more, $2.5 \times 10^3$ pfu/ml or more, $5 \times 10^3$ pfu/ml or more, $10^4$ pfu/ml or more, $2.5 \times 10^4$ pfu/ml or more, $5 \times 10^4$ pfu/ml or more, or $10^5$ pfu/ml or more in a subject. In certain embodiments, the virus achieves a viral yield of 1 pfu/ml or more, 10 pfu/ml or more, $5 \times 10^1$ pfu/ml or more, $10^2$ pfu/ml or more, $5 \times 10^2$ pfu/ml or more, $10^3$ pfu/ml or more, $2.5 \times 10^3$ pfu/ml or more, $5 \times 10^3$ pfu/ml or more, $10^4$ pfu/ml or more, $2.5 \times 10^4$ pfu/ml or more, $5 \times 10^4$ pfu/ml or more, or $10^5$ pfu/ml or more in a subject within 4 hours, 6 hours, 8 hours, 12 hours, 16 hours, 24 hours, or 48 hours. In certain embodiments, the virus achieves a viral yield of 1 pfu/ml or more, 10 pfu/ml or more, $10^1$ pfu/ml or more, $5 \times 10^1$ pfu/ml or more, $10^2$ pfu/ml or more, $5 \times 10^2$ pfu/ml or more, $10^3$ pfu/ml or more, $2.5 \times 10^3$ pfu/ml or more, $5 \times 10^3$ pfu/ml or more, $10^4$ pfu/ml or more, $2.5 \times 10^4$ pfu/ml or more, $5 \times 10^4$ pfu/ml or more, or $10^5$ pfu/ml or more in a subject within 48 hours, 72 hours, or 1 week. In accordance with these embodiments, the viral yield may be measured in the infected tissue or serum. In a specific embodiment, the subject is immunocompetent. In another embodiment, the subject is immunocompromised or immunosuppressed.

In some embodiments, the virus achieves a viral yield of 1 pfu or more, 10 pfu or more, $5 \times 10^1$ pfu or more, $10^2$ pfu or more, $5 \times 10^2$ pfu or more, $10^3$ pfu or more, $2.5 \times 10^3$ pfu or more, $5 \times 10^3$ pfu or more, $10^4$ pfu or more, $2.5 \times 10^4$ pfu or more, $5 \times 10^4$ pfu or more, or $10^5$ pfu or more in a subject. In certain embodiments, the virus achieves a viral yield of 1 pfu or more, 10 pfu or more, $5 \times 10^1$ pfu or more, $10^2$ pfu or more, $5 \times 10^2$ pfu or more, $10^3$ pfu or more, $2.5 \times 10^3$ pfu or more, $5 \times 10^3$ pfu or more, $10^4$ pfu or more, $2.5 \times 10^4$ pfu or more, $5 \times 10^4$ pfu or more, or $10^5$ pfu or more in a subject within 4 hours, 6 hours, 8 hours, 12 hours, 16 hours, 24 hours, or 48 hours. In certain embodiments, the virus achieves a viral yield of 1 pfu or more, 10 pfu or more, $10^1$ pfu or more, $5 \times 10^1$ pfu or more, $10^2$ pfu or more, $5 \times 10^2$ pfu or more, $10^3$ pfu or more, $2.5 \times 10^3$ pfu or more, $5 \times 10^3$ pfu or more, $10^4$ pfu or more, $2.5 \times 10^4$ pfu or more, $5 \times 10^4$ pfu or more, or $10^5$ pfu or more in a subject within 48 hours, 72 hours, or 1 week. In accordance with these embodiments, the viral yield may be measured in the infected tissue or serum.

In some embodiments, the virus achieves a viral yield of 1 infectious unit or more, 10 infectious units or more, $5 \times 10^1$ infectious units or more, $10^2$ infectious units or more, $5 \times 10^2$ infectious units or more, $10^3$ infectious units or more, $2.5 \times 10^3$ infectious units or more, $5 \times 10^3$ infectious units or more, $10^4$ infectious units or more, $2.5 \times 10^4$ infectious units or more, $5 \times 10^4$ infectious units or more, or $10^5$ infectious units or more in a subject. In certain embodiments, the virus achieves a viral yield of 1 infectious unit or more, 10 infectious units or more, $5 \times 10^1$ infectious units or more, $10^2$ infectious units or more, $5 \times 10^2$ infectious units or more, $10^3$ infectious units or more, $2.5 \times 10^3$ infectious units or more, $5 \times 10^3$ infectious units or more, $10^4$ infectious units or more, $2.5 \times 10^4$ infectious units or more, $5 \times 10^4$ infectious units or more, or $10^5$ infectious units or more in a subject within 4 hours, 6 hours, 8 hours, 12 hours, 16 hours, 24 hours, or 48 hours. In certain embodiments, the virus achieves a viral yield of 1 infectious unit or more, 10 infectious units or more, $10^1$ infectious units or more, $5 \times 10^1$ infectious units or more, $10^2$ infectious units or more, $5 \times 10^2$ infectious units or more, $10^3$ infectious units or more, $2.5 \times 10^3$ infectious units or more, $5 \times 10^3$ infectious units or more, $10^4$ infectious units or more, $2.5 \times 10^4$ infectious units or more, $5 \times 10^4$ infectious units or more, or $10^5$ infectious units or more in a subject within 48 hours, 72 hours, or 1 week. In accordance with these embodiments, the viral yield may be measured in the infected tissue or serum. In a specific embodiment, the virus achieves a yield of less than $10^4$ infectious units. In other embodiments the virus achieves a yield of $10^5$ or more infectious units.

In some embodiments, the virus achieves a viral titer of 1 infectious unit per ml or more, 10 infectious units per ml or more, $5 \times 10^1$ infectious units per ml or more, $10^2$ infectious units per ml or more, $5 \times 10^2$ infectious units per ml or more, $10^3$ infectious units per ml or more, $2.5 \times 10^3$ infectious units per ml or more, $5 \times 10^3$ infectious units per ml or more, $10^4$ infectious units per ml or more, $2.5 \times 10^4$ infectious units per ml or more, $5 \times 10^4$ infectious units per ml or more, or $10^5$ infectious units per ml or more in a subject. In certain embodiments, the virus achieves a viral titer of 10 infectious units per ml or more, $5 \times 10^1$ infectious units per ml or more, $10^2$ infectious units per ml or more, $5 \times 10^2$ infectious units per ml or more, $10^3$ infectious units per ml or more, $2.5 \times 10^3$ infectious units per ml or more, $5 \times 10^3$ infectious units per ml or more, $10^4$ infectious units per ml or more, $2.5 \times 10^4$ infectious units per ml or more, $5 \times 10^4$ infectious units per ml or more, or $10^5$ infectious units per ml or more in a subject within 4 hours, 6 hours, 8 hours, 12 hours, 16 hours, 24 hours, or 48 hours. In certain embodiments, the virus achieves a viral titer of 1 infectious unit per ml or more, 10 infectious units per ml or more, $5 \times 10^1$ infectious units per ml or more, $10^2$ infectious units per ml or more, $5 \times 10^2$ infectious units per ml or more, $10^3$ infectious units per ml or more, $2.5 \times 10^3$ infectious units per ml or more, $5 \times 10^3$ infectious units per ml or more, $10^4$ infectious units per ml or more, $2.5 \times 10^4$ infectious units per ml or more, $5 \times 10^4$ infectious units per ml or more, or $10^5$ infectious units per ml or more in a subject within 48 hours, 72 hours, or 1 week. In accordance with these embodiments, the viral titer may be measured in the infected tissue or serum. In a specific embodiment, the virus achieves a titer of less than $10^4$ infectious units per ml. In some embodiments, the virus achieves $10^5$ or more infectious units per ml.

In some embodiments, the virus infects a cell and produces, $10^1$ or more, $2.5 \times 10^1$ or more, $5 \times 10^1$ or more, $7.5 \times 10^1$ or more, $10^2$ or more, $2.5 \times 10^2$ or more, $5 \times 10^2$ or more, $7.5 \times 10^2$ or more, $10^3$ or more, $2.5 \times 10^3$ or more, $5 \times 10^3$ or more, $7.5 \times 10^3$ or more, $10^4$ or more, $2.5 \times 10^4$ or more, $5 \times 10^4$ or more, $7.5 \times 10^4$ or more, or $10^5$ or more viral particles per cell. In certain embodiments, the virus infects a cell and produces 10 or more, $10^1$ or more, $2.5 \times 10^1$ or more, $5 \times 10^1$ or more, $7.5 \times 10^1$ or more, $10^2$ or more, $2.5 \times 10^2$ or more, $5 \times 10^2$ or more, $7.5 \times 10^2$ or more, $10^3$ or more, $2.5 \times 10^3$ or more, $5 \times 10^3$ or more, $7.5 \times 10^3$ or more, $10^4$ or more, $2.5 \times 10^4$ or more, $5 \times 10^4$ or more, $7.5 \times 10^4$ or more, or $10^5$ or more viral particles per cell within 4 hours, 6 hours, 8 hours, 12 hours, 16 hours, or 24 hours. In other embodiments, the virus infects a cell and produces 10 or more, $10^1$ or more, $2.5 \times 10^1$ or more, $5 \times 10^1$ or more, $7.5 \times 10^1$ or more, $10^2$ or more, $2.5 \times 10^2$ or more, $5 \times 10^2$ or more, $7.5 \times 10^2$ or more, $10^3$ or more, $2.5 \times 10^3$ or more, $5 \times 10^3$ or more, $7.5 \times 10^3$ or more, $10^4$ or more, $2.5 \times 10^4$ or more, $5 \times 10^4$ or more, $7.5 \times 10^4$ or more, or $10^5$ or more viral particles per cell within 48 hours, 72 hours, or 1 week.

In other embodiments, the virus is latent for a period of about at least 1 day, 2 days, 3 days, 4 days, 5 days, 6 days, 7 days, 8 days, 9 days, 10 days, 11 days, 12 days, 13 days, 14 days, or 15 days. In another embodiment, the virus is latent for a period of about at least 1 week, or 2 weeks, 3 weeks, 4 weeks, 5 weeks, 6 weeks, 7 weeks, 8 weeks, 9 weeks, or 10 weeks. In a further embodiment, the virus is latent for a period of about at least 1 month, 2 months, 3 months, 4 months, 5 months, 6 months, 7 months, 8 months, 9 months, 10 months, or 11 months. In yet another embodiment, the virus is latent for a period of about at least 1 year, 2 years, 3 years, 4 years, 5 years, 6 years, 7 years, 8 years, 9 years, 10 years, 11 years, 12 years, 13 years, 14 years, or 15 years. In some embodiments, the virus is latent for a period of greater than 15 years.

Non-limiting examples of non-segmented, negative-sense, single-stranded RNA viruses whose replication can be inhibited or reduced (e.g., prevention of a symptom of viral replication), management and/or treatment of viral replication or the pathological state resulting therefrom, by the administration of one or more Compounds or a composition comprising one or more Compounds. The Compound can be a Compound with a formula of A3-J, including a Compound with a formula of A3-1, A3-7, A3-8, A3-9, A3-11, or A3-12. In certain specific embodiments, the Compound has a formula A3-2 or A3-5. The viruses whose replication can be inhibited or reduced, include: rhabdoviruses (e.g., Vesicular Stomatitis virus (VSV), rabies, and rabies-related viruses), paramyxoviruses, e.g., Newcastle Disease Virus (NDV), measles virus, mumps virus, parainfluenza viruses such as Sendai virus, and pneumoviruses such as respiratory syncytial virus (RSV) and metapneumovirus), filoviruses (e.g., Ebola virus and Marburg virus), hepatitis delta virus, and bornaviruses. Non-limiting examples of segmented, negative-sense, single-stranded RNA viruses whose replication may be inhibited or reduced by the administration of one or more Compounds or a composition comprising one or more Compounds include: orthomyxoviruses (e.g., influenza A virus, influenza B virus, influenza C virus, thogoto virus, and infectious salmon anemia virus), bunyaviruses (e.g., bunyamwera virus, Hantaan virus, Dugbe virus, Rift Valley fever virus, and tomato spotted wilt virus), and, es (e.g., lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Tacaribe virus, and Tamiami virus). In a specific embodiment, the negative-sense, single-stranded RNA virus is an enveloped virus. In another specific embodiment, the negative-sense, single-stranded RNA virus is influenza virus (e.g., an influenza A virus, influenza B virus, or influenza C virus). In one embodiment, the influenza A virus is an H5N1 isolate. In another embodiment, the influenza A virus is an H1N1 isolate. In another embodiment, the negative-sense, single-stranded RNA virus is a parainfluenza virus, a measles virus, a mumps virus, or a respiratory syncytial virus (RSV). In one embodiment, the parainfluenza virus is Sendai virus. In one embodiment, the parainfluenza virus is a human parainfluenza virus (HPIV). In specific embodiments the HPIV is HPIV type 2 (HPIV-2), HPIV type 3 (HPIV-3), or HPIV type 4 (HPIV-4). In one embodiment, the HPIV-4 is subtype A. In another embodiment, the HPIV-4 is subtype B. In a specific embodiment, the virus is NDV. In another specific embodiment, the virus is VSV. In certain embodiments, the virus is not a rhabdovirus. In certain other embodiments, the negative-sense, single-stranded RNA virus is not VSV. In certain embodiments, the negative-sense, single-stranded RNA virus is not a Sendai virus. In certain embodiments, the negative-sense, single-stranded RNA virus is not a Vesicular Stomatitis virus. In certain embodiments, the negative-sense, single-stranded RNA virus is Newcastle disease virus, Vesicular Stomatitis virus, Sendai virus, or influenza virus types A or B.

In a specific embodiment, the virus infects humans. In some embodiments, the DNA virus, double-stranded RNA virus, positive-sense, single-stranded RNA virus, negative-sense, single-stranded RNA virus, or retrovirus virus is a naturally occurring strain, variant or mutant of a DNA virus, a double-stranded RNA virus, a positive-sense, single-stranded RNA virus, a negative-sense, single-stranded RNA virus, or a retrovirus, a mutagenized DNA virus, a double-stranded RNA virus, a positive-sense, single-stranded RNA virus, a negative-sense, single-stranded RNA virus, or a retrovirus, a reassortant DNA virus, a double-stranded RNA virus, a positive-sense, single-stranded RNA virus, a negative-sense, single-stranded RNA virus, or a retrovirus and/or a genetically engineered DNA virus, a double-stranded RNA virus, a positive-sense, single-stranded RNA virus, a negative-sense, single-stranded RNA virus, or a retrovirus.

5.6 Patient Population

In some embodiments, a Compound, or a combination therapy or a composition thereof is administered to a subject suffering from a virus infection (e.g., a DNA-virus, double-stranded RNA virus, positive-sense, single-stranded RNA virus, negative-sense, single-stranded RNA virus or retroviral infection). In other embodiments, a Compound, a composition thereof, or a combination therapy is administered to a subject predisposed or susceptible to a viral infection (e.g., a DNA virus, double-stranded RNA virus, positive-sense, single-stranded RNA virus, negative-sense, single-stranded RNA virus, or retrovirus infection). In some embodiments, a Compound, or a combination therapy is administered to a subject that lives in a region where there has been or might be an outbreak with a viral infection (e.g., a DNA virus, double-stranded RNA virus, positive-sense, single-stranded RNA virus, negative-sense, single-stranded RNA virus, or retrovirus infection). In some embodiments, the viral infection (e.g., a DNA virus, double-stranded RNA virus, positive-sense, single-stranded RNA virus, negative-sense, single-stranded RNA virus, or retrovirus infection is a latent viral infection. In other embodiments, the viral infection (e.g., a DNA virus, double-stranded RNA virus, positive-sense, single-stranded RNA virus, negative-sense, single-stranded RNA virus, or retrovirus infection) is an active infection. In yet other embodiments, the viral infection (e.g., DNA virus, double-stranded RNA virus, positive-sense, single-stranded RNA virus, negative-sense, single-stranded RNA virus, or retrovirus virus infection) is a chronic viral infection.

In certain embodiments, a Compound, a composition thereof or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, a Compound, a composition thereof or a combination therapy is administered to a human at risk for a virus infection. In certain embodiments, a Compound, a composition thereof or a combination therapy is administered to a human with a virus infection. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a Compound, a composition thereof or a combination therapy is administered to a human infant. In other embodiments, a Compound, a composition thereof or a combination therapy is administered to a human child. In other embodiments, a Compound, a composition thereof or a combination therapy is administered to a human adult. In yet other embodiments, a Compound, a composition thereof or a combination therapy is administered to an elderly human. In certain embodiments, a Compound, a composition thereof or a combination therapy is administered to a premature human infant.

In certain embodiments, a Compound, a composition thereof or a combination therapy is administered to a pet, e.g., a dog or cat. In certain embodiments, a Compound, a composition thereof or a combination therapy is administered to a farm animal or livestock, e.g., pig, cows, horses, chickens, etc. In certain embodiments, a Compound, a composition thereof or a combination therapy is administered to a bird, e.g., ducks or chicken.

In certain embodiments, a Compound, a composition thereof or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, a Compound, a composition thereof or a combination therapy is administered to a subject receiving or recovering from immunosuppressive therapy. In certain embodiments, a Compound, a composition thereof or a combination therapy is administered to a subject that has or is at risk of getting cancer, AIDS, another viral infection, or a bacterial infection. In certain embodiments, a Compound, a composition thereof or a combination therapy is administered to a subject that is, will or has undergone surgery, chemotherapy and/or radiation therapy. In certain embodiments, a Compound, a composition thereof or a combination therapy is administered to a subject that has cystic fibrosis, pulmonary fibrosis, or another disease which makes the subject susceptible to a viral infection. In certain embodiments, a Compound, a composition thereof or a combination therapy is administered to a subject that has, will have or had a tissue transplant. In some embodiments, a Compound, a composition thereof or a combination therapy is administered to a subject that lives in a nursing home, a group home (i.e., a home for 10 or more subjects), or a prison. In some embodiments, a Compound, a composition thereof or a combination therapy is administered to a subject that attends school (e.g., preschool, elementary school, middle school, junior high school, high school or university) or daycare. In some embodiments, a Compound, a composition thereof or a combination therapy is administered to a subject that works in the healthcare area, such as a doctor or a nurse, or in a hospital. In certain embodiments, a Compound, a composition thereof or a combination therapy is administered to a subject that is pregnant or plans on becoming pregnant.

In some embodiments, a patient is administered a Compound, a composition thereof or a combination therapy before any adverse effects or intolerance to therapies other than to the Compound develops. In some embodiments, a Compound, a composition thereof or a combination therapy is administered to refractory patients. In a certain embodiment, refractory patient is a patient refractory to a standard antiviral therapy. In certain embodiments, a patient with a viral infection, is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a viral infection is refractory when viral replication has not decreased or has increased.

In some embodiments, a Compound, a composition thereof or a combination therapy is administered to a patient to prevent the onset or reoccurrence of a virus infection (e.g., a DNA virus, double-stranded RNA virus, positive-sense, single-stranded RNA virus, negative-sense, single-stranded RNA virus, or retrovirus infection) in a patient at risk of developing such infections. In some embodiments, a Compound, a composition thereof or a combination therapy is administered to a patient who is susceptible to adverse reactions to conventional therapies.

In some embodiments, a Compound, a composition thereof or a combination therapy is administered to a patient who has proven refractory to therapies other than Compounds, but are no longer on these therapies. In certain embodiments, the patients being managed or treated are patients already being treated with antibiotics, antivirals, antifungals, or other biological therapy/immunotherapy. Among these patients are refractory patients, patients who are too young for conventional therapies, and patients with reoccurring viral infections despite management or treatment with existing therapies.

In some embodiments, the subject being administered a Compound, a composition thereof or a combination therapy has not received a therapy prior to the administration of the Compound, a composition thereof or combination therapy. In other embodiments, a Compound or a combination therapy is administered to a subject who has received a therapy prior to administration of the Compound, a composition thereof or combination therapy. In some embodiments, the subject administered a Compound, a composition thereof or a combination therapy was refractory to a prior therapy or experienced adverse side effects to the prior therapy or the prior therapy was discontinued due to unacceptable levels of toxicity to the subject.

5.7 Mode of Administration

When administered to a patient, a Compound is preferably administered as a component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the Compound and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a Compound into the bloodstream.

In specific embodiments, it may be desirable to administer a Compound locally. This may be achieved, for example, and not by way of limitation, by local infusion, topical application, e.g., in conjunction with a wound dressing, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce a Compound into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a Compound is formulated as a suppository, with traditional binders and vehicles such as triglycerides.

For viral infections with cutaneous manifestations, a Compound can be administered topically. Similarly, for viral infections with ocular manifestation, a Compound can be administered ocularly. For viruses with pulmonary manifestations, a Compound can be administered intranasally or by an inhaler or nebulizer.

In another embodiment, a Compound is delivered in a vesicle, in particular a liposome (See Langer, 1990, Science 249:1527 1533; Treat et al., in Liposomes in the Therapy of Infectious Disease and Bacterial infection, Lopez-Berestein and Fidler (eds.), Liss, New York, pp. 353 365 (1989); Lopez Berestein, ibid., pp. 317 327; See generally ibid.).

In another embodiment, a Compound is delivered in a controlled release system (See, e.g., Goodson, in Medical Applications of Controlled Release, supra, vol. 2, pp. 115 138 (1984)). Examples of controlled-release systems are discussed in the review by Langer, 1990, Science 249:1527 1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105). In a specific embodiment, a controlled-release system comprising a Compound is placed in close proximity to the tissue infected with a virus to be prevented, treated and/or managed. In accordance with this embodiment, the close proximity of the controlled-release system to the infection may result in only a fraction of the dose of a Compound required if it is systemically administered.

In certain embodiments, it may be preferable to administer a Compound via the natural route of infection of the virus against which a Compound has antiviral activity. For example, it may be desirable to administer a Compound into the lungs by any suitable route to treat or prevent an infection of the respiratory tract by viruses (e.g., influenza virus). Pulmonary administration can also be employed, e.g., by use of an inhaler or nebulizer, and formulation with an aerosolizing agent for use as a spray.

5.8 Agents for Use in Combination with Compounds

Therapeutic or prophylactic agents that can be used in combination with Compounds for the prevention, treatment and/or management of a viral infection (e.g., a DNA virus, double-stranded RNA virus, positive-sense, single-stranded RNA virus, negative-sense, single-stranded RNA virus, or retrovirus infection). Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, and non-steroidal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used or is currently being used for the prevention, management, and/or treatment of a viral infection (e.g., a DNA virus, double-stranded RNA virus, positive-sense, single-stranded RNA virus, negative-sense, single-stranded RNA virus, or retrovirus or can be used in combination with a Compound described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 199 9; Cecil Textbook of Medicine, 20th Ed., Bennett and Plum (eds.), W.B. Saunders, Philadelphia, 1996, and Physicians' Desk Reference (60 ed. 1007) for information regarding therapies (e.g., prophylactic or therapeutic agents) which have been or are currently being used for preventing, treating and/or managing viral infections.

5.8.1 Antiviral Agents

Antiviral agents that can be used in combination with Compounds include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor which includes, for example, abacavir, AZT, ddI, ddC, 3TC, d4T, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination with Compounds include the following: rifampicin, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; pyridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zanamivir (RELENZA™); and zinviroxime.

5.8.2 Antibacterial Agents

Antibacterial agents, including antibiotics, that can be used in combination with Compounds include, but are not limited to, aminoglycoside antibiotics, glycopeptides, amphenicol antibiotics, ansamycin antibiotics, cephalosporins, cephamycins oxazolidinones, penicillins, quinolones, streptogamins, tetracycline, and analogs thereof. In some embodiments, antibiotics are administered in combination with a Compound to prevent and/or treat a bacterial infection.

In a specific embodiment, Compounds are used in combination with other antibacterial agents, including but not limited to, streptomycin, neomycin, erythromycin, carbomycin, and spiramycin.

In one embodiment, the antibacterial agent is selected from the group consisting of ampicillin, amoxicillin, ciprofloxacin, gentamycin, kanamycin, neomycin, penicillin G, streptomycin, sulfanilamide, and vancomycin. In another embodiment, the antibacterial agent is selected from the group consisting of azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, and trimethoprim.

Additional, non-limiting examples of antibacterial agents for use in combination with Compounds include the following: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithomycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o benethamine, penicillin 0, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). Additional examples include cycloserine, mupirocin, tuberin amphomycin, bacitracin, capreomycin, colistin, enduracidin, enviomycin, and 2,4 diaminopyrimidines (e.g., brodimoprim).

5.9 Dosages & Frequency of Administration

The amount of a Compound, or the amount of a composition comprising a Compound, that will be effective in the prevention, treatment and/or management of a viral infection (e.g., a DNA virus, double-stranded RNA virus, positive-sense, single-stranded RNA virus, negative-sense, single-stranded RNA virus, or retrovirus infection) can be determined by standard clinical techniques. In vitro or in vivo assays may optionally be employed to help identify optimal dosage ranges. The precise dose to be employed will also depend, e.g., on the route of administration, the type of infection, and the seriousness of the infection, and should be decided according to the judgment of the practitioner and each patient's or subject's circumstances.

In some embodiments, the dosage of a Compound is determined by extrapolating from the no observed adverse effective level (NOAEL), as determined in animal studies. This extrapolated dosage is useful in determining the maximum recommended starting dose for human clinical trials. For instance, the NOAELs can be extrapolated to determine human equivalent dosages (HED). Typically, HED is extrapolated from a non-human animal dosage based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, See *Guidance for Industry Estimating the Maximum Safe Starting Dose in Initial Clinical Trials for Therapeutics in Adult Healthy Volunteers*, U.S. Department of Health and Human Services Food and Drug Administration Center for Drug Evaluation and Research (CDER), Pharmacology and Toxicology, July 2005. In one embodiment, a Compound or composition thereof is administered at a dose that is lower than the human equivalent dosage (HED) of the NOAEL over a period of 1 week, 2 weeks, 3 weeks, 1 month, 2 months, three months, four months, six months, nine months, 1 year, 2 years, 3 years, 4 years or more.

In certain embodiments, a dosage regime for a human subject can be extrapolated from animal model studies using the dose at which 10% of the animals die ($LD_{10}$). In general the starting dose of a Phase I clinical trial is based on preclinical testing. A standard measure of toxicity of a drug in preclinical testing is the percentage of animals that die because of treatment. It is well within the skill of the art to correlate the $LD_{10}$ in an animal study with the maximal-tolerated dose (MTD) in humans, adjusted for body surface area, as a basis to extrapolate a starting human dose. In some embodiments, the interrelationship of dosages for one animal model can be converted for use in another animal, including humans, using conversion factors (based on milligrams per meter squared of body surface) as described, e.g., in Freireich et al., Cancer Chemother. Rep., 1966, 50:219-244. Body surface area may be approximately determined from height and weight of the patient. See, e.g., Scientific Tables, Geigy Pharmaceuticals, Ardley, N.Y., 1970, 537. In certain embodiments, the adjustment for body surface area includes host factors such as, for example, surface area, weight, metabolism, tissue distribution, absorption rate, and excretion rate. In addition, the route of administration, excipient usage, and the specific disease or virus to target are also factors to consider. In one embodiment, the standard conservative starting dose is about 1/10 the murine $LD_{10}$, although it may be even lower if other species (i.e., dogs) were more sensitive to the Compound. In other embodiments, the standard conservative starting dose is about 1/100, 1/95, 1/90, 1/85, 1/80, 1/75, 1/70, 1/65, 1/60, 1/55, 1/50, 1/45, 1/40, 1/35, 1/30, 1/25, 1/20, 1/15, 2/10, 3/10, 4/10, or 5/10 of the murine $LD_{10}$. In other embodiments, an starting dose amount of a Compound in a human is lower than the dose extrapolated from animal model studies. In another embodiment, an starting dose amount of a Compound in a human is higher than the dose extrapolated from animal model studies. It is well within the skill of the art to start doses of the active composition at relatively low levels, and increase or decrease the dosage as necessary to achieve the desired effect with minimal toxicity.

Exemplary doses of Compounds or compositions include milligram or microgram amounts per kilogram of subject or sample weight (e.g., about 1 microgram per kilogram to about 500 milligrams per kilogram, about 5 micrograms per kilogram to about 100 milligrams per kilogram, or about 1 microgram per kilogram to about 50 micrograms per kilogram). In specific embodiments, a daily dose is at least 50 mg, 75 mg, 100 mg, 150 mg, 250 mg, 500 mg, 750 mg, or at least 1 g.

In another embodiment, the dosage is a unit dose of 5 mg, preferably 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 5 mg to about 100 mg, about 100 mg to about 200 mg, about 150 mg to about 300 mg, about 150 mg to about 400 mg, 250 mg to about 500 mg, about 500 mg to about 800 mg, about 500 mg to about 1000 mg, or about 5 mg to about 1000 mg.

In certain embodiments, suitable dosage ranges for oral administration are about 0.001 milligram to about 500 milligrams of a Compound, per kilogram body weight per day. In specific embodiments, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one Compound is administered, then, in some embodiments, the dosages correspond to the total amount administered. In a specific embodiment, oral compositions contain about 10% to about 95% a Compound by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. In some embodiments, suitable dosage ranges for intranasal administration are about 0.01 pg/kg body weight per day to about 1 mg/kg body weight per day. Suppositories generally contain about 0.01 milligram to about 50 milligrams of a Compound per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 500 milligrams per kilogram of body weight per day. Suitable doses for topical administration include doses that are in the range of about 0.001 milligram to about 50 milligrams, depending on the area of administration. Effective doses may be extrapolated from dose-response curves derived from in vitro or animal model test systems. Such animal models and systems are well known in the art.

In another embodiment, a subject is administered one or more doses of an effective amount of a Compound or a composition, wherein the effective amount is not the same for each dose.

In certain embodiments, a subject is administered a Compound or a composition in an amount effective to inhibit viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a Compound or a composition in an amount effective to inhibit or reduce viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a Compound or a composition in an amount effective to inhibit or reduce viral genome replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or other known to one of skill in the art.

In certain embodiments, a subject is administered a Compound or a composition in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a Compound or a composition in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a Compound or a composition in an amount effective to inhibit or reduce viral protein synthesis by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered a Compound or a composition in an amount effective to inhibit or reduce the spread of a virus from a cell, tissue, or organ to another cell, tissue or organ by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a Compound or a composition in an amount effective to inhibit or reduce the spread of a virus from a cell, tissue or organ to another cell, tissue or organ by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered a Compound or a composition in an amount effective to inhibit or reduce viral titer by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a Compound or a composition in an amount effective to inhibit or reduce viral titer by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered a Compound or a composition in an amount effective to inhibit or reduce viral titer by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, a subject is administered a Compound or a composition in an amount effective to inhibit or reduce viral replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a Compound or a composition in an amount effective to inhibit or reduce viral replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered a Compound or a composition in an amount effective to inhibit or reduce viral replication by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, a subject is administered a Compound or a composition in an amount effective to inhibit or reduce the ability of the virus to spread to other individuals by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a Compound or a composition in an amount effective to inhibit or reduce the ability of the virus to spread to other cells, tissues or organs in the subject by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art.

In certain embodiments, a dose of a Compound or a composition is administered to a subject every day, every other day, every couple of days, every third day, once a week, twice a week, three times a week, or once every two weeks. In other embodiments, two, three or four doses of a Compound or a composition is administered to a subject every day, every couple of days, every third day, once a week or once every two weeks. In some embodiments, a dose(s) of a Compound or a composition is administered for 2 days, 3 days, 5 days, 7 days, 14 days, or 21 days. In certain embodiments, a dose of a Compound or a composition is administered for 1 month, 1.5 months, 2 months, 2.5 months, 3 months, 4 months, 5 months, 6 months or more.

The dosages of prophylactic or therapeutic agents which have been or are currently used for the prevention of a symptom of viral infection, treatment and/or management of a viral infection (e.g., a negative-sense, single-stranded RNA virus infection) can be determined using references available to a clinician such as, e.g., the Physicians' Desk Reference ($61^{st}$ ed. 2007). In a specific embodiment, dosages lower than those which have been or are currently being used to prevent, treat and/or manage the infection are utilized in combination with one or more a Compound or compositions.

For Compounds which have been approved for uses other than prevention of a symptom of viral infection, treatment or management of viral infections, safe ranges of doses can be readily determined using references available to clinicians, such as e.g., the Physician's Desk Reference ($61^{st}$ ed. 2007).

The above-described administration schedules are provided for illustrative purposes only and should not be considered limiting. A person of ordinary skill in the art will readily understand that all doses are within the scope of the invention.

In certain embodiments, a Compound provided herein is administered as a solid dosage form, for example, as a capsule.

5.10 Use of Compounds in Cell Culture and as Disinfectants

Described herein are the use of Compounds as ingredients in cell culture-related products in which it is desirable to have antiviral activity. In one embodiment, one or more Compounds are added to cell culture media. In certain embodiments, Compounds (e.g., any Compounds that prove too toxic or are not used in subjects) are added to cell culture-related products, such as media. Provided herein are the use of Compounds as ingredients in disinfectants and soaps. The Compounds can also be used in manufacturing processes where a sterile environment is essential for the production of a product that is free or substantially free of viruses.

5.11 Kits

Described herein are kits that can be used in the above methods. In one embodiment, the kit comprises a Compound contained in an appropriate package. In specific embodiments, a kit comprises a Compound, and a second therapy each contained in an appropriate package. In some embodiments, a kit further comprises a negative control and/or a positive control, in an appropriate package(s). In some embodiments, the kit further comprises a DNA virus, double-stranded RNA virus, positive-sense, single-stranded RNA virus, negative-sense, single-stranded RNA virus, or retrovirus. In specific embodiments, the kit contains instructions for use.

6. EXAMPLE

This example describes the identification of Compounds that inhibit the replication of a broad spectrum of viruses. In particular, the following examples describes the antiviral effect of A3 derivatives. The results are shown in FIG. 8, 9, 10, Section 8.1-8.5, Tables 2, 3 and 4 infra.

6.1 Materials and Methods

6.2 Cell Lines, Viruses And Plasmids

Human alveolar basal epithelial (A549) cells, African green monkey kidney (Vero) cells, HEK 293T, TZM bl (HeLa), CV1, MDCK, BHK, PK-15, chicken fibroblast (DF1) cells, and primary human tracheal-bronchial epithelial (HTBE) cells were obtained from the American Type Culture Collection (ATCC, Manassas, Va.). A549 cells, CV1 cells, Huh7.5 cells, TZM-bl cells, Madin Darby canine kidney (MDCK) cells, and Vero cells were cultured in Dulbecco's modified Eagle's medium (DMEM) (Invitrogen Corp., Carlsbad, Calif.) supplemented with 10% fetal bovine serum (FBS) (HyClone; South Logan, Utah) and 100 U/mL penicillin G sodium and 100 µg/mL streptomycin sulfate (Invitrogen Corp., Carlsbad, Calif.). MDCK cells were cultured in Minimum Essential Medium (MEM) (Invitrogen Corp., Carlsbad, Calif.) supplemented with 10% FBS, 2 mM L-glutamine (Invitrogen Corp., Carlsbad, Calif.), 100 U/mL penicillin G sodium and 100 mg/L streptomycin sulfate and 0.15% $NaHCO_3$ (Invitrogen Corp., Carlsbad, Calif.). MEF cells were kindly provided by BenjamintenOever (Mount Sinai School of Medicine, New York, N.Y.). Bronchial tracheal ferret cells were kindly provided by Randy Albrecht (Mount Sinai School of Medicine, New York, N.Y.). Human liver hepatoma (Huh 7.5) cells were kindly provided by Charles Rice (Rockefeller University, New York, N.Y.). Vero cells expressing the replicon system of West Nile virus (WNV) and dengue I virus (DENY-I) were kindly provided by Pei Yong Shi (Novartis Institute for Tropical Diseases, Singapore). A549, HEK 293T, Huh 7.5, TZM bl, Vero, CV1, DF-1, BHK, PK-15, MEF, and ferret cells were cultured in DMEM (Invitrogen) supplemented with 10% FBS (HyClone). MDCK cells were cultured in Eagle's minimum essential medium (MEM) (Invitrogen) supplemented with 10% FBS. HTBE cells were cultured in Bronchial Epithelial Cell Growth Medium (BEGM) supplemented with the BEGM SingleQuot kit (Lonza).

Vesicular Stomatitis virus expressing the green fluorescence protein (VSV-GFP) was provided by John Hiscott (McGill University, Montreal, Canada), and was grown and titered in Vero cells. Newcastle disease virus strain B1 (rNDV/B1) was grown in 10-day-old embryonated hens' eggs and titered in DF1 cells.

Influenza viruses A/WSN/33 (H1N1) and B/Yamagata/88 were grown and titered in MDCK cells. Sindbis virus (SINV) and vesicular stomatitis virus expressing the green fluorescence protein (VSV-GFP; kindly provided by John Hiscott, McGill University, Montreal, QC, Canada) were grown and titered in Vero cells. Newcastle disease virus (NDV-LaSota) was grown in 10-d-old embryonated hens' eggs and titered in DF1 cells. The influenza viruses A/Hong Kong/68 (H3N2), A/Victoria/3/75 (H3N2), A/Sw/Texas/98 (H1N1), A/Moscow/10/99 (H3N2), A/NY/2008 (H1N1), A/PR/8/34 (H1N1), A/Udorn/72 (H3N2), and Sendai Virus (SV52) were grown in 8-d-old embryonated hens' eggs and titered in MDCK or Vero cells. Human adenovirus (hAd5) was grown and titered in A549 cells. Vaccinia virus (NYVAC) was grown and titered in CV1 cells. HIV-1 (NL4-3) viral stocks were produced by transfection of HEK 293T and titered as described previously (30). Hepatitis C virus (Jc1FLAG2[p7-nsGluc2a]) was kindly provided by Charles Rice (Rockefeller University, New York, N.Y.) and grown as described in Marukian et al., 2008 Hepatology 48:1843-1850.

For the construction of the influenza mini-genome reporter construct (pPolI-358Luc) the firefly luciferase open reading frame from pGL3 (Promega Corp., Madison, Wis.) was amplified by PCR and the 5' and 3' ends of the cRNA promoter of the influenza A/WSN/33 virus NP segment were incorporated on either end (Neumann and Hobom, 1995). This product was then inserted into the pPolI vector (Pleschka et al., 1996) with the luciferase gene in the negative sense.

6.2.1 Cell Viability Assay

The CellTiter 96 AQueous One Solution Cell Proliferation Assay (referred to as the MTS assay in this study) (Promega Corp., Madison, Wis.) was used to detect cell viability according to the specifications of the manufacturer. Briefly, A549 cells were seeded into 96-well plates (Corning Life Sciences, Lowell, Mass.) at $5 \times 10^3$ cells per well and allowed to incubate for 24 hours at 37° C., 5% $CO_2$. After incubation, the medium was aspirated and replaced with 100 µL of fresh DMEM containing the Compounds at various concentrations. Following a further 24 hour incubation, the MTS solution was added to each well and left to incubate for 2 hours before measuring absorbance at 450 nm using a Beckman Coulter DTX 880 plate reader (Beckman Coulter, Inc., Fullerton, Calif.).

6.2.2 Viral Growth Assays in the Presence of Compounds

A549 cells were seeded into 6-well plates at $5 \times 10^5$ cells per well. After incubation for 24 hours at 37° C. and 5% $CO_2$, the cells were washed with phosphate buffered saline (PBS) (Invitrogen Corp., Carlsbad, Calif.) and the medium was replaced with DMEM supplemented with 0.3% BSA, 0.1% FBS and 100 U/mL penicillin G sodium and 100 µg/mL streptomycin sulfate containing the Compound of interest. Compounds that inhibit viral replication were used at their most potent, but non-toxic, concentration (12.5 µM for SDZ-201106 and 1.25 µM for rottlerin). The cells were incubated in the Compound-containing media for 6 hours prior to infection. When testing the response of influenza A/WSN/33 virus and of H5N1/PR8 virus to Compounds, infections were done at a multiplicity of 1 was used. For influenza B/Yamagata/88 virus, infections were done at a multiplicity of 5 when testing Compounds. Compounds were absent during the 1 hour incubation with the virus but were present in the post-infection medium (DMEM supplemented with 0.3% BSA, 0.1% FBS and 100 U/mL penicillin G sodium and 100 µg/mL streptomycin sulfate). For infection with influenza B virus and the human influenza A virus, NDV-LaSota and SV52 isolates this post-infection medium also contained 1 µg/ml TPCK-treated trypsin (Sigma-Aldrich; St. Louis, Mo.). When indicated, the medium was supplemented with uracil, dihydroorotic acid, and orotic acid. The infected cells were incubated at 37° C. with the exception for influenza B virus infected cells, which were incubated at 33° C. The viral titers for all viruses were determined at various times post infection by standard plaque assay in MDCK cells. For influenza virus plaque reduction assays, the overlay medium was supplemented with the indicated purines, pyrimidines, or components of the pyrimidine de novo biosynthesis pathway. Viral replication of WNV, DENV-I, and HCV was monitored by the production of Renilla luciferase, which was measured using the Renilla Luciferase Assay Kit (Promega) according to the specifications of the manufacturer. TZM-bl reporter cells, which encode a Tat-responsive β-galactosidase indicator gene under the transcriptional control of the HIV-1 LTR, were used to assess HIV-1 infectivity in the presence of A3. β-Galactosidase activity was quantified 48 h after infection as described in Harari et al., 2009 J Virol 83:295-303. Infectivity values were normalized and $IC_{50}$ values were computed by nonlinear regressions (GraphPadPRISM). For the time-of-addition experiments, TZM-bl reporter cells were infected in duplicate with NL4-3 at an MOI of 0.1. FDA-approved HIV-1 antiretroviral drugs were added at 0, 1, 2, 4, 6, 8, 10, and 12 h postinfection at a multiple of the concentration required to inhibit 50% of the viral infectivity ($IC_{50}$), as follows: lamivudine (a nucleoside analog reverse transcriptase inhibitor, concentration 10 µM; 25-fold $IC_{50}$), nevirapine (a nonnucleoside reverse transcriptase inhibitor, concentration 1 µM; 11-fold $IC_{50}$); raltegravir (an integrase inhibitor, 1 µM; 75-fold $IC_{50}$), and amprenavir (a protease inhibitor, 1 µM; 50-fold $IC_{50}$). A3 was used at a concentration of 1 µM (five-fold $IC_{50}$). β-Galactosidase activity was quantified 48 h after infection as previously described in Harari et al., 2009 J Virol 83:295-303.

6.2.3 Apoptosis Assay

The Caspase-3 Colorimetric Assay (R&D Systems, Inc., Minneapolis, Minn.) was used to detect whether the Compounds have any apoptotic effects. A549 cells were seeded into 60 mm tissue culture treated dishes (Corning Life Sciences, Lowell, Mass.) at $1.5 \times 10^6$ cells per dish and allowed to incubate for 24 hours at 37° C., 5% $CO_2$. After incubation, the medium was aspirated and the cells were washed with PBS. Fresh DMEM post-infection medium was added, containing Compounds at the same concentrations as were used for the viral infections. As a positive control for the induction of apoptosis, the cells were treated with staurosporin at a concentration of 5 µM. Cells were incubated for 6 hours at 37° C., 5% $CO_2$. Subsequently, they were harvested, washed twice with PBS, lysed and incubated with the DEVD-AFC substrate for an additional hour at 37° C., 5% $CO_2$ before measuring fluorescence at 500 nm using a Versa Fluor Fluorometer (BioRad; Hercules, Calif.).

6.2.4 Influenza Virus Minigenome Assay

A549 cells were seeded into 12-well plates at $2 \times 10^5$ cells per well and incubated overnight at 37° C., 5% CO2. The cells were transfected with pCAGGS constructs for influenza A/WSN/33 virus PB1, PB2, and PA (100 ng each) and NP (200 ng), the RNA polymerase II driven *Renilla* luciferase reporter pRLTK (Promega) (200 ng), and the influenza virus-specific RNA polymerase I driven firefly luciferase reporter (pPolI Luc) (150 ng). Four hours before transfection, the cells were cultured in DMEM supplemented with compounds at their CC10 or DMSO. The transfection was performed with Lipofectamine 2000 (Invitrogen) in OptiMEM (Invitrogen), which was also supplemented with compounds or DMSO. OptiMEM was replaced 4 h posttransfection with DMEM containing compounds or DMSO. After a 20- to 24-h incubation period, cells were harvested, and firefly luciferase and *Renilla* luciferase expression was determined using the Dual Luciferase Assay Kit (Promega).

6.2.5 Primer Extension Assay

A549 cells were seeded into 12-well plates at $2 \times 10^5$ cells per well. After incubation for 24 h at 37° C. and 5% CO2, the cells were washed with PBS, and the medium was replaced with DMEM supplemented with DMSO, A3 (2 and 10 µM) or ribavirin (10 and 100 µM). The cells were incubated for 4 h before infection with influenza virus A/PR/8/34 (MOI=7). RNA was extracted 9 h postinfection using the QIAamp viral RNA kit (Qiagen). Primers were synthesized for the NA segment of influenza A/PR/8/34 virus (c/m-RNA primer: 5'-tccagtatggttttgatttccg-3' and v-RNA primer: 5'-ggactagtgggagcatcatttc-3') and the human 5S rRNA (5'-tcccaggcggtctcccatcc-3'). For the RT reaction, they were labeled with ATP-[γ-32P] using T4-kinase (Invitrogen) according to the specifications of the manufacturer. Viral RNA (2 µg) was reverse transcribed with the SuperScript First-Strand Synthesis System (Invitrogen) using labeled primers for v-, c/mRNA, and 5s rRNA. Samples were separated on a 6% SDS/PAGE gel that contained 5 M urea, transferred to membrane, and crosslinked. cDNA was visualized by exposure (24-72 h at −80° C.) to autoradiographic film (World Wide Medical Products [WWMP]).

6.3 Post-Infection Medium for Infections with Vaccinia Virus, Adenovirus, Hepatitis C Virus and HIV Dulbecco's modified Eagle's medium (DMEM) (Invitrogen Corp., Carlsbad, Calif.) supplemented with 10% fetal bovine serum (FBS) (HyClone; South Logan, Utah) and 100 U/mL penicillin G sodium and 100 µg/mL streptomycin sulfate (Invitrogen Corp., Carlsbad, Calif.).

6.4 Post-Infection Medium for Infections with Newcastle Disease Virus and Sendai Virus Dulbecco's modified Eagle's medium (DMEM) (Invitrogen Corp., Carlsbad, Calif.) supplemented with 0.3% bovine serum albumin (BSA), 0.1% FBS, 100 U/mL penicillin G sodium, 100 µg/mL streptomycin sulfate and 1 ug/mL TPCK-trypsin.

7. CHARACTERIZATION OF A3 DERIVATIVES

The cytotoxicity of each Compound was determined for a 24 hour period in A549 cells in a concentration range from 0.1-300 µM. For further tissue culture studies, the individual Compound concentration never exceeded the $CC_{10}$. The $CC_{10}$ is the concentration of 10% cytotoxicity (in other words the concentration with 90% cell viability compared to untreated cells).

To validate the inhibitory potential of the Compounds, A549 cells were pretreated for 4-6 hours at increasing concentrations of each Compound. Subsequently, the cells were infected with influenza A virus at an MOI of 1 and incubated for another 20-24 hours. The Compounds were present throughout the course of infection. Viral replication and release of viral particles was determined by hemagglutination assays using 0.5% chicken red blood cells. A Compound was followed up further if it reduced viral replication by at least 2 wells of hemagglutinin (HA), which equals about a 75% reduction in viral titers. Two additional criteria used were that the $IC_{50}$ (half maximal inhibitory concentration) was below 10 µM and that the SI, the selective index ($CC_{50}/IC_{50}$), was above 10. 18 Compounds able to inhibit influenza A virus replication in A549 cells at non-cytotoxic concentrations were identified.

All Compounds were further tested for their effect on the other negative-sense, single-stranded RNA viruses influenza B virus, NDV and VSV (FIGS. 3 and 4), sindbis virus and VSV (FIGS. 8A & B). The cytotoxicity of the Compounds was also determined in different cell lines (MDCK, MEF, 293T, HUH 7.5, Detroit, HTBE) and their effect on viral replication was determined.

The following assays were performed to narrow down the site of action for each Compound. In particular, entry assay studies were performed. RNA replication and transcription were also measured, using influenza virus mini-genome assays as described in Pleschka et al., 1996, "A plasmid-based reverse genetics system for influenza A virus," J. Virol. 70:4188-92. Such mini-genome assays enable the identification of Compound that inhibits the viral polymerase or cellular proteins that are involved in viral replication, translation and RNA trafficking. The Compounds were also tested in kinetic studies in which they were added prior to and post infection at different times and virus growth was assayed using a plaque assay.

Three lead Compounds which display high potency in inhibiting viral replication in A549 cells and primary lung cells, such as human tracheobronchial epithelial (HTBE) cells, were identified. As shown in Table 2 below, the ability of three Compounds, 2-(5-(2,3-dimethyl-1H-indol-5-yl)-1,3,4-oxadiazol-2-ylthio)-1-(pyrrolidin-1-yl)ethanone ("A3"); 4-(4-bromophenyl)-N-methyl-N-(tetrahydro-1,1-dioxido-3-thienyl)-2-thiazolamine ("A35"); and 9-(benzo[d][1,3]dioxol-5-yl)-4-hydroxy-6,7-dimethoxynaphtho[2,3-c]furan-1(3H)-one ("C2") to inhibit influenza viruses A and B ("FluA" and "FluB," respectively) was tested in different cell types. Cells were infected at an MOI of 1 and viral titers were determined 24 hours post-infection.

was not affected as monitored by the expression of a *renilla* luciferase control plasmid (FIG. 6). In viral entry assays performed, A3 did not inhibit viral entry. A3, at a concentration of 10 μM, was found to inhibit influenza A viruses and influenza B viruses similarly (see, e.g., Table 2). As shown in FIG. 3, A3 inhibited the growth of influenza B virus in A549 cells by about 1.5 logs (FIG. 3). The $IC_{50}$ of A3 in HTBE cells was found to be 42 nM and the SI was measured as 2571.

Lead Compound A35 was identified in a screen of the Asinex 1 source library (12,378 Compounds; ASINEX, Winston-Salem, N.C., USA). A35 was found to be highly potent in a variety of different cell lines with an inhibition of influenza virus replication of up to 4 logs (in A549 and HTBE cells). In viral entry assay studies performed, A35 did not affect the entry step of influenza virus. In kinetic studies using A549 cells infected with influenza strain WSN (MOI=1), when A35 was added prior to infection or even up to 4 hours post infection, inhibition of viral replication was unaltered (4 logs). Thus, A35 is likely to target a crucial step in the viral life cycle. Without being bound by any theory, these experiments suggest that A35 affects RNA trafficking and/or packaging. At a concentration of 11.2 μM, A35 inhibits influenza A virus with high specificity, but has a less significant inhibition of influenza B virus (FIG. 3), NDV (FIG. 4A) and VSV (FIG. 4B).

Lead Compound C2 was identified in a screen of the ChemDiv 4 source library (14,677 Compounds; ChemDiv Inc., San Diego, Calif., USA). C2, at a concentration of 2 μM, was found to potently inhibit influenza virus replication in HTBE cells by up to 3.5 logs. The $IC_{50}$ of C2 in HTBE cells was determined to be 59 nM and the SI was found to be approximately 350. In kinetic studies, addition of C2 to infected cells at 1 hour post infection did not affect the course of infection.

TABLE 2

| Compound | $CC_{50}$ | $IC_{50}$ | SI | inhibition of FluA | inhibition of FluB |
|---|---|---|---|---|---|
| A3 | 268 μM (A549) | 0.54 μM (A549)* | 496 (A549) | 97% (A549)* | 94% (A549)* |
|  | >100 μM (MDCK) | 0.82 μM (MDCK)** | >122 (MDCK) | ~99.6% (MDCK)** |  |
|  | >100 μM (MEF) | 3.6 μM (MEF)** | >28 (MEF) | ~91.2% (MEF)** |  |
|  | 108 μM (HTBE) | 0.042 μM (HTBE)* | 2571 (HTBE) | 99.99% (HTBE)* |  |
| A35 | 110 μM (A549) | 2.1 μM (A549)* | 53 (A549) | 99.988% (A549)* | 63% (A549)* |
|  | 26.8 μM (MDCK) | 3.91 μM (MDCK)** | 7 (MDCK) | ~75% (MDCK)** |  |
|  | 96.6 μM (MEF) | 2.64 μM (MEF)** | 37 (MEF) | ~99.6% (MEF)** |  |
|  | 29.3 μM (293T) | 6.2 μM (293T)** | 5 (293T) | ~50% (293T)** |  |
|  | 79.7 μM (Detroit) | 2.07 μM (Detroit)** | 39 (Detroit) | ~95.6% (Detroit)** |  |
|  | 59 μM (HUH7.5) | 3.97 μM (HUH7.5)** | 15 (HUH7.5) | ~98.4% (HUH7.5)** |  |
|  | 119 μM (HTBE) | 1.98 μM (HTBE)* | 60 (HTBE) | 99.98% (HTBE)* |  |
| C2 | 131 μM (A549) | 1.6 μM (A549)** | 82 (A549) | 94.7% (A549)* | 63% (A549)* |
|  | 0.67 μM (MDCK) | 0.15 μM (MDCK)** | 4 (MDCK) | ~87.5% (MDCK)** |  |
|  | 4.85 μM (MEF) | 0.34 μM (MEF)** | 14 (MEF) | ~96% (MEF)** |  |
|  | 20.6 μM (HTBE) | 0.059 μM (HTBE)* | 349 (HTBE) | 99.96% (HTBE)* |  |

*viral titer determined by plaque assay
**viral titer determined by HA assay

Lead Compound A3 was identified in a screen of the Asinex 1 source library (12,378 Compounds; ASINEX, Winston-Salem, N.C., USA). In kinetic studies using A549 cells infected with influenza strain WSN (MOI=1), A3 was found to inhibit viral replication by approximately 2 logs when added 2 hours prior to infection and by 1 log when added up to 2 hours post infection (FIG. 2). In studies using an influenza virus mini-genome reporter construct, A3 was found to inhibit viral RNA polymerase activity by up to 99% at 10 μM, whereas ribavirin, a known polymerase inhibitor, was found to inhibit only 90% of the activity at 100 μM (FIG. 5). A3 was tested in dose response experiments and at all A3 concentrations (0.4-30 μM), the overall host cell replication machinery In viral entry assay studies performed, it was found that entry of influenza virus and VSV, which both enter the cell by endocytosis, was inhibited in the presence of C2 whereas entry of the retrovirus MLV, which fuses with the plasma membrane, was unaffected. Therefore, without being bound by any theory, it appears that C2 targets an early step in the viral life cycle, the endocytosis of the viral particles.

For two Compounds, A3 and A35, a number of their derivatives were tested for cytotoxicity and inhibition of viral replication in order to identify related structures that can be used as antiviral agents. The results from these experiments are shown in Table 3 below.

TABLE 3

| Name | Structure | CC$_{10}$ (A549) | CC$_{50}$ (A549) | IC$_{50}$ (A549) | SI (A549) | Inhibition of FluA |
|---|---|---|---|---|---|---|
| A35 | 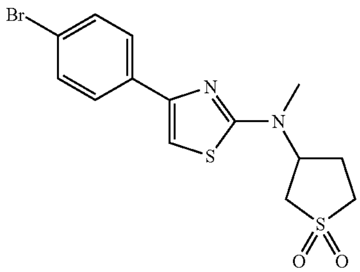 [SMILES: CN(c1nc(-c2ccc(Br)cc2)cs1)C1CCS(=O)(=O)C1] | 11.2 μM | 110 μM | 2.1 μM * | 53 | 99.99% * |
| A35-1 | 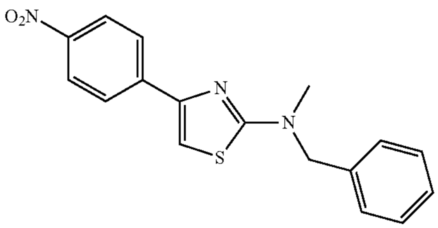 [SMILES: CN(Cc1ccccc1)c1nc(-c2ccc([N+](=O)[O-])cc2)cs1] | 10.8 μM | 201 μM | 3.24 μM  | 62 | ~75%  |
| A35-2 | 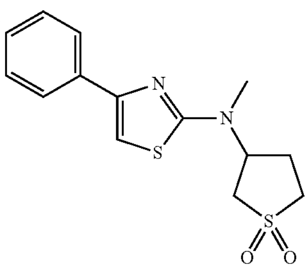 [SMILES: CN(c1nc(-c2ccccc2)cs1)C1CCS(=O)(=O)C1] | 12.2 μM | 148 μM | n/a | n/a | none ** |
| A35-3 | 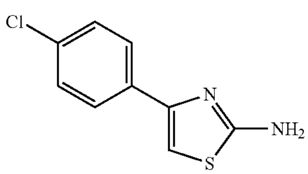 [SMILES: Nc1nc(-c2ccc(Cl)cc2)cs1] | 11.4 μM | 164.8 μM | n/a | n/a | none ** |
| A35-4 | 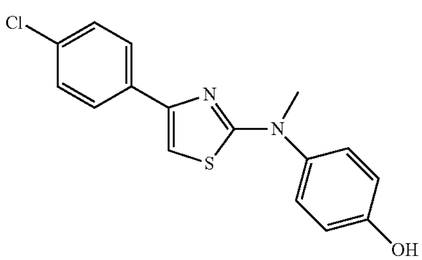 [SMILES: CN(c1ccc(O)cc1)c1nc(-c2ccc(Cl)cc2)cs1] | 6 μM | 30 μM | 6 μM  | 5 | ~50%  |
| A35-5 | 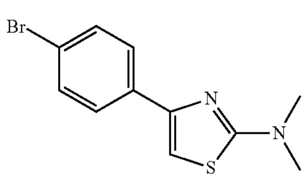 | 17.8 μM | 242.4 μM | 12.3 μM  | 20 | ~65%  |

TABLE 3-continued
| Name | Structure | CC₁₀ (A549) | CC₅₀ (A549) | IC₅₀ (A549) | SI (A549) | Inhibition of FluA |
|---|---|---|---|---|---|---|
| A3 | 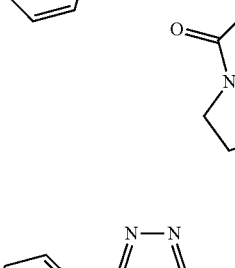 | 38 μM | 268 μM | 0.54 μM * | 496 | 99.2% * |
| A3-1 | 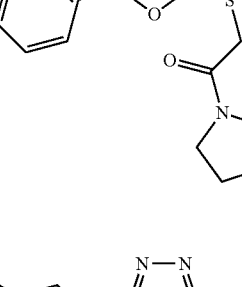 | 17.3 μM | 316 μM | n/a | n/a | ~29% ** |
| A3-2 | 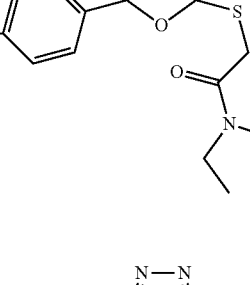 | 29 μM | 198.5 μM | 1.2 μM  | >165 | ~97%  |
| A3-3 | 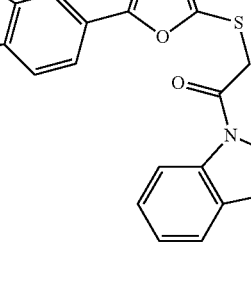 | 8.5 μM | 65 μM | 8.5 μM  | 8 | ~50%  |
| A3-4 | 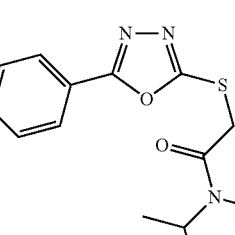 | 10.7 μM | 17.7 μM | 1.65 μM  | 11 | ~87.5%  |

TABLE 3-continued

| Name | Structure | CC$_{10}$ (A549) | CC$_{50}$ (A549) | IC$_{50}$ (A549) | SI (A549) | Inhibition of FluA |
|---|---|---|---|---|---|---|
| A3-5 | 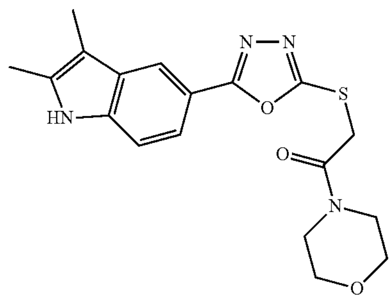 [SMILES: Cc1[nH]c2ccc(-c3nnc(SCC(=O)N4CCOCC4)o3)cc2c1C] | 10.2 μM | 256.8 μM | 0.5 μM  | 514 | ~97%  |
| A3-6 | 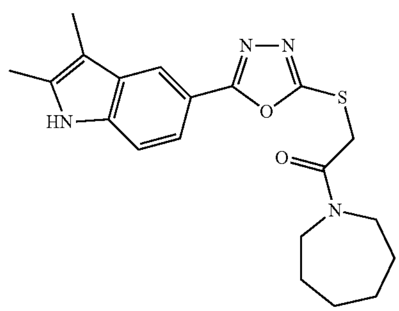 [SMILES: Cc1[nH]c2ccc(-c3nnc(SCC(=O)N4CCCCCC4)o3)cc2c1C] | 18.2 μM | 179 μM | 0.98 μM  | 180 | ~87.5%  |
| A3-7 | 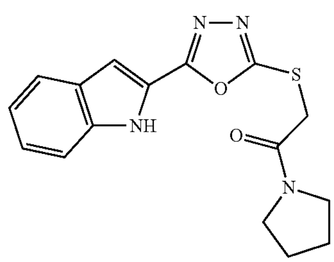 [SMILES: O=C(CSc1nnc(-c2cc3ccccc3[nH]2)o1)N1CCCC1] | 15.2 μM | 134 μM | n/a | n/a | ~29% ** |
| A3-8 | 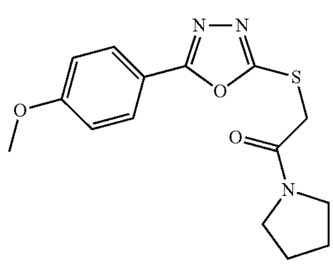 [SMILES: COc1ccc(-c2nnc(SCC(=O)N3CCCC3)o2)cc1] | 11.8 μM | 249.8 μM | n/a | n/a | none ** |
| A3-9 | 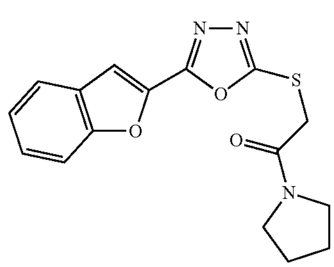 [SMILES: O=C(CSc1nnc(-c2cc3ccccc3o2)o1)N1CCCC1] | 10.9 μM | 197 μM | n/a | n/a | ~29% ** |

TABLE 3-continued

| Name | Structure | CC$_{10}$ (A549) | CC$_{50}$ (A549) | IC$_{50}$ (A549) | SI (A549) | Inhibition of FluA |
|---|---|---|---|---|---|---|
| A3-11 | 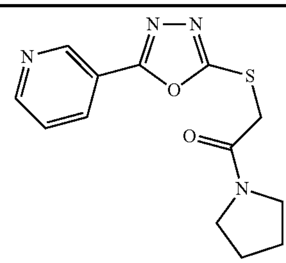 | 32.6 μM | 248.8 μM | n/a | n/a | none ** |
| A3-12 | 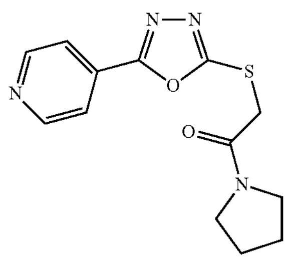 [SMILES: O=C(CSc1nnc(-c2ccncc2)o1)N1CCCC1] | 11.5 μM | 186 μM | n/a | n/a | ~29% ** |

\* -determined by plaque assay;
\*\* -determined by HA assay;
n/a-not available
A3 and its derivatives, A3-1, A3-2, A3-3, A3-4A3-5, A3-6, A3-7, A3-8, A3-9, A3-11, and A3-12 were tested for cytotoxicity and inhibition of viral replication

8. ANTIVIRAL ACTIVITY OF COMPOUND A3 AND ITS DERIVATIVES

The applicant has discovered that Compound A3 and its derivatives have a broad spectrum antiviral activity against different viruses. The results are shown in Table 4. These Compounds can be used as antiviral composition for treatment and prevention of diseases.

8.1 Inhibition of Vaccinia Virus

CV 1 cells were cultured in medium containing A3 derivatives or the solvent (DMSO) for at least 2 hours prior to infection. The CV1 cells were subsequently infected with vaccinia virus (strain: NYVAC). Infection was done at an MOI of 1. The infected cells were incubated for an hour at 37° C. The post-infection medium contained Compounds at the same concentration. The infection was allowed to proceed for 24 hours before cells and produced virus was harvested. The viral titer was determined by plaque assay performed in CV1 cells. FIG. 10A shows the result for the inhibition of vaccinia virus.

8.2 Inhibition of Adenovirus

A549 cells were cultured in medium containing A3 derivatives or the solvent (DMSO) for at least 2 hours prior to infection. The A549 cells were subsequently infected with adenovirus (strain: hAd5—human Adenovirus 5). Infection was done at an MOI of 0.5. The infected cells were incubated for an hour at 37° C. The post-infection medium contained Compounds at the same concentration. The infection was allowed to proceed for 24 hours before cells and produced virus was harvested. The viral titer was determined by plaque assay performed in A549 cells. FIG. 10B shows the result for the inhibition of the adenovirus.

8.3 Inhibition of Newcastle Disease Virus and Sendai Virus

A549 cells were cultured in medium containing A3 derivatives or the solvent (DMSO) for at least 2 hours prior to infection. The A549 cells were subsequently infected with Newcastle Disease Virus (strain: La Sota) or Sendai virus (strain: 52). Infections were done at an MOI of 1 for an hour at 37° C. The post-infection medium contained Compounds at the same concentration. The infection was allowed to proceed for 24 hours before produced virus was harvested. The viral titers were determined by plaque assay performed in Vero cells followed by immuno-staining with specific virus antibodies. FIG. 9A shows the result for the inhibition of Newcastle disease virus and FIG. 9B shows the result for the inhibition of Sendai virus.

8.4 Inhibition of Hepatitis C virus

Huh7.5 cells were cultured in medium containing A3 derivatives, ribavirin or the solvent (DMSO) for at least 2 hours prior to infection. The Huh7.5 cells were subsequently infected with a recombinant hepatitis C virus expressing Gaussia luciferase (strain: HCVcc-JC1) for an hour at 37° C. The post-infection medium contained Compounds at the same concentration. The infection was allowed to proceed up to 48 hours before produced virus was harvested. Aliquots of the supernatant were evaluated for Gaussia luciferase activity at 24 and 48 hpi. Gaussia luciferase is secreted by the virus and reflects viral replication. FIG. 12 shows the result for the inhibition of hepatitis C virus.

8.5 Inhibition of Dengue Virus (DenV-1) and West Nile Virus (WNV)

Vero cells expressing *Renilla* luciferase under the control of the DenV-I or the WNV replicon system were cultured in medium containing A3 derivatives, mycophenolic acid or the solvent (DMSO) at least for two hours prior to infection. The vero cells were subsequently infected with Dengue virus or West Nile virus. The post-infection medium contained Compounds at the same concentration. The infection was allowed to proceed up to 24 hours before produced virus was harvested. The vero cells were subsequently harvested. Aliquots of the supernatant were evaluated for Renilla luciferase activity. FIG. 13 shows the result for the inhibition of West Nile virus. FIG. 14 shows the result for the inhibition of Dengue virus.

8.6 Inhibition of HIV-1

TZM-bl cells (HeLa cells that express a tat inducible beta-galactosidase reporter gene) were cultured in medium containing A3 derivatives or the solvent (DMSO) for at least 2 hours prior to infection. The TZM-bl cells were subsequently infected with HIV-1 (strain: NL4-3). The post-infection medium contained Compounds at the same concentration. The infection was allowed to proceed for 48 hours before produced virus was harvested. The TZM-bl cells were subsequently harvested. Aliquots of the supernatant were evaluated for beta-galactosidase activity as a reflection of HIV-1 replication. FIG. 11 shows the results for the inhibition of HIV-1.

more pronounced in primary human tracheal-bronchial epithelial (HTBE) cells (FIG. 16A). Viral titers were reduced by 4 logs after 24 h, and the IC50 was determined to be 0.04 µM, which resulted in an SI of >2,380 (CC50>100 04). In contrast, the same experiment performed in mouse embryo fibroblast (MEF) cells (FIG. 16B) reduced viral titers by less than 2 logs at a similar concentration of A3. The $IC_{50}$ was determined as 1 µM, which resulted in an SI of >100 (CC50>100 04).

8.8 A3 Inhibits Influenza Virus Polymerase Activity

A3 was tested at different time points during the viral life cycle to determine whether it acts early or late in infection. First, the effects on replication when added pre- or postinfection were compared. A549 cells were infected at a high MOI with influenza A/WSN/33 virus and compound treatment started 2 h preinfection or at several time points postinfection. Inhibition was observed when A3 was present preinfection or when added up to 2 h postinfection but not later (FIG. 17A). The inhibition was further demonstrated by reduced levels of viral proteins in the presence of A3 (FIG. 17B). These results indicated that A3 was acting at early to mid stages in the viral life cycle, which suggest that replication and transcription are targeted. An influenza virus minigenome assay was performed to determine whether influenza virus polymerase

TABLE 4

Broad-spectrum antiviral activity of Compound A3 and its analogues

| Virus | Genome | Family | | Virus Inhibition | | Conditions |
|---|---|---|---|---|---|---|
| Influenza A virus (various strains of H1N1 and H3N2) | (−) ssRNA | Orthomyxoviridae | virus | ~5 logs | 99.999% | (MOI = 0.01; compound @10 uM) |
| Influenza B virus (B/Ya/88) | (−) ssRNA | Orthomyxoviridae | virus | ~1.5 logs | 95% | (MOI = 1; compound @10 uM) |
| Newcastle Disease virus (La Sota) | (−) ssRNA | Paramyxoviridae | virus | ~2 logs | 99% | (MOI = 1; compound @10 uM) |
| Sendai Virus 52 | (−) ssRNA | Paramyxoviridae | virus | ~3 logs | 99.90% | (MOI = 1; compound @10 uM) |
| Vesicular Stomatitis virus | (−) ssRNA | Rhabdoviridae | virus | ~5 logs | 99.999% | (MOI = 0.01; compound @10 uM) |
| Sindbis Virus | (+) ssRNA | Togaviridae | virus | ~2 logs | 99% | (MOI = 1; compound @10 uM) |
| Hepatitis C virus | (+) ssRNA | Flaviviridae | virus | ~2 logs | 99% | (compound @10 uM) |
| West Nile Virus | (+) ssRNA | Flaviviridae | replicon cell line | ~1 logs | 90% | (compound @10 uM) |
| Dengue I Virus | (+) ssRNA | Flaviviridae | replicon cell line | ~1 logs | 90% | (compound @10 uM) |
| Vaccinia Virus (NYVAC) | dsDNA | Poxviridae | virus | ~3 logs | 99.90% | (MOI = 1; compound @1 uM) |
| Adeno virus (hAd5) | dsDNA | Adenoviridae | virus | ~4 logs | 99.99% | (MOI = 1; compound @10 uM) |
| HIV-1 | ssRNA RT | Retroviridae | virus | ~2 logs | 99% | (compound @2 uM) |

8.7 Antiviral Activity of Compound A3

A compound was defined to be a strong inhibitor of influenza virus replication if the luminescence signal of an influenza virus inducible firefly luciferase reporter was decreased by at least 90% compared with that in untreated cells. Compound A3 from the Asinex1 library displayed a very strong effect on viral replication, such that there was no luminescence detectable. The compound was further evaluated for cytotoxity, and its CC50 in A549 cells was determined to be 268 µM over a 24-h incubation period (FIG. 15). To confirm the results of the primary screen, A3 was tested at noncytotoxic concentrations in viral replication assays performed at an MOI of 0.01. A reduction in viral titers of 4 logs was detected at a concentration of 2 µM, and the IC50 over a 24-h replication period was determined as 0.178 µM (FIG. 15). This resulted in a selective index (SI=CC50/IC50) of 1,505, which indicates compound A3 to be a very strong inhibitor with very little toxicity. The inhibitory effect of A3 was even activity is affected by A3. A549 cells were transfected with expression plasmids for the influenza virus polymerase proteins (PB1, PB2, and PA), the nucleoprotein (NP), and the previously described influenza virus-specific firefly luciferase reporter (Hoffman et al., 2008 Antiviral Res 80:124-134). To normalize for transfection efficiency, a Renilla luciferase plasmid was cotransfected. Compounds were added at 4 h before transfection and were present for the duration of the assay. A3 strongly inhibits influenza virus polymerase function by 98% compared with the DMSO control, without affecting cellular gene expression as monitored by Renilla luciferase activity (FIG. 18A). Diphyllin was shown to inhibit influenza virus entry (Konig et al., 2010 Nature 463:813-817) and was included as a negative control, whereas ribavirin, a known polymerase inhibitor of RNA viruses, was included as a positive control. A dose-response assay indicated that influenza virus polymerase activity is inhibited to the same degree by 2 µM A3 as with 100 µM ribavirin (FIG. 6), suggesting that A3 is 50 times more potent than ribavirin. To determine whether A3 is affecting viral RNA synthesis, primer extension assays were performed on the NA segment to observe synthesis of v-, c-, and mRNA. To control for cellular replication, the levels of 5S rRNA were also monitored. A3 was shown to fully inhibit production of all three viral RNA species at a concentration of 2 µM (FIG. 18B) without decreasing levels of cellular 5S rRNA. Similar results were obtained for 100 µM ribavirin.

8.9 A3 Displays Broad-Spectrum Antiviral Activity

A3 was shown to inhibit a number of influenza virus strains of both H1N1 and H3N2 subtypes (FIG. 19); therefore, to determine whether A3 displays broad-spectrum antiviral activity, the replication of viruses representing several different families was examined (Table 3). All viruses were tested in A549 cells (unless otherwise indicated) at a concentration of 10 µM A3 or less. At this concentration, A3 does not appear to be either cytostatic or cytotoxic over a 48-h period (FIG. 20). For influenza A/WSN/33 virus (representing the Orthomyxoviridae), viral titers for infections performed under multicycle replication conditions (MOI=0.01) are decreased by 5 logs compared with a 2-log reduction for infections performed at an MOI of 1 (FIG. 7A). Sendai virus (SV52), a paramyxovirus, was inhibited by 3 logs (FIG. 21A), and an even stronger effect of A3 on viral replication was found for vesicular stomatitis virus (rhabdoviridae), the titer of which was decreased by 5 logs (FIG. 7B). The positive-sense RNA viruses, Sindbis virus (togaviridae) and hepatitis C virus (flaviviridae), were both inhibited by 2 logs in the presence of A3. Surprisingly, DNA viruses were also affected by A3, and titers of the human adenovirus 5 (hAd5) (adenoviridae) were reduced by 6 logs in the presence of A3 (FIG. 21B). It was noted that viruses that depend on DNA synthesis, such as vaccinia virus (poxyiridae), adenovirus, and HIV-1 (retroviridae), were also sensitive to A3. The IC50 of A3 against HIV-1 (NL4-3) is in the mid nanomolar range (205 nM, Fig. S6A), which is remarkably similar to the IC50 for influenza virus (178 nM; FIG. 15). Time-of-addition experiments with A3 in conjunction with FDA-approved HIV-1 antiretroviral drugs show that A3 remains active even when added as late as 12 h after infection, whereas inhibitors of reverse transcriptase or integration lose activity when added 4-8 or 10-12 h postinfection (FIG. 22B). These findings suggest that the mechanism of action of A3 is at the step of transcription after integration but before maturation (FIG. 22B).

8.10 Antiviral Activity of A3 is Linked to Pyrimidine Metabolism

Figure 23:
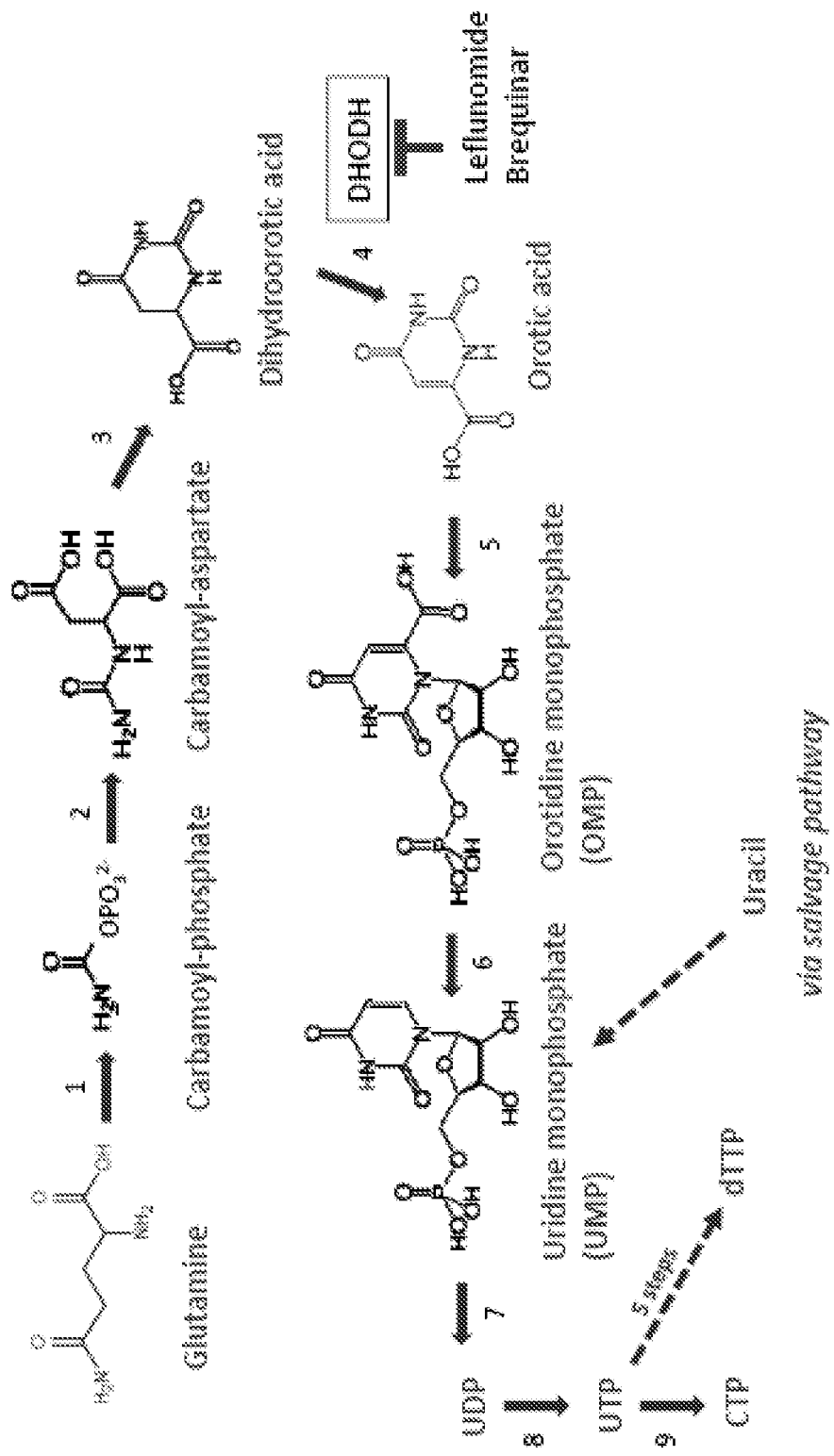

Antivirals with broad-spectrum activity often affect nucleotide synthesis or incorporation. The de novo pyrimidine synthesis pathway is shown in FIG. 23.

To address the question of whether A3 acts in such a way, A3 activity was tested in the presence of different purines and pyrimidines in plaque reduction assays. Uracil was found to be the only base that is able to reverse the inhibitory effect of A3 and to restore viral replication. Surprisingly, at these concentrations, the effect was seen only in Madin-Darby canine kidney (MDCK) cells and not in A549 cells (FIG. 24A-C). Thus, A3 is able to inhibit viral replication efficiently in both cell lines, but its effect can be more easily compensated for by uracil in MDCK cells than in A549 cells. This result suggested a tissue or species specificity of A3, and therefore viral replication in the presence of A3 was tested in a panel of cell lines of different species. A strong inhibition of viral replication was seen among human cells (A549, 293T) and primate cells (Vero, CV1), independent of the tissue origin, and only high concentrations of uracil (100-fold) were able to partially restore viral replication (FIG. 25A). Vero cells, unlike CV1, are deficient in type I IFN, but both cell lines are derived from the same species (*Cercopithecus aethiops*) and tissue (kidney). This suggested that the involvement of IFN could be excluded in the antiviral actions of A3. This was further confirmed via quantitative RT-PCR, which showed no induction of IFN-13 and other antiviral genes (ISG56, IRF7, RIG-I, and TNF-α) upon treatment with A3 alone or in combination with influenza virus infection in A549 cells. In nonprimate mammalian cells, complete inhibition of viral replication by A3 was seen in both MDCK and bronchial-tracheal ferret cells, but this could be easily reversed by the addition of uracil.

Figure 24:
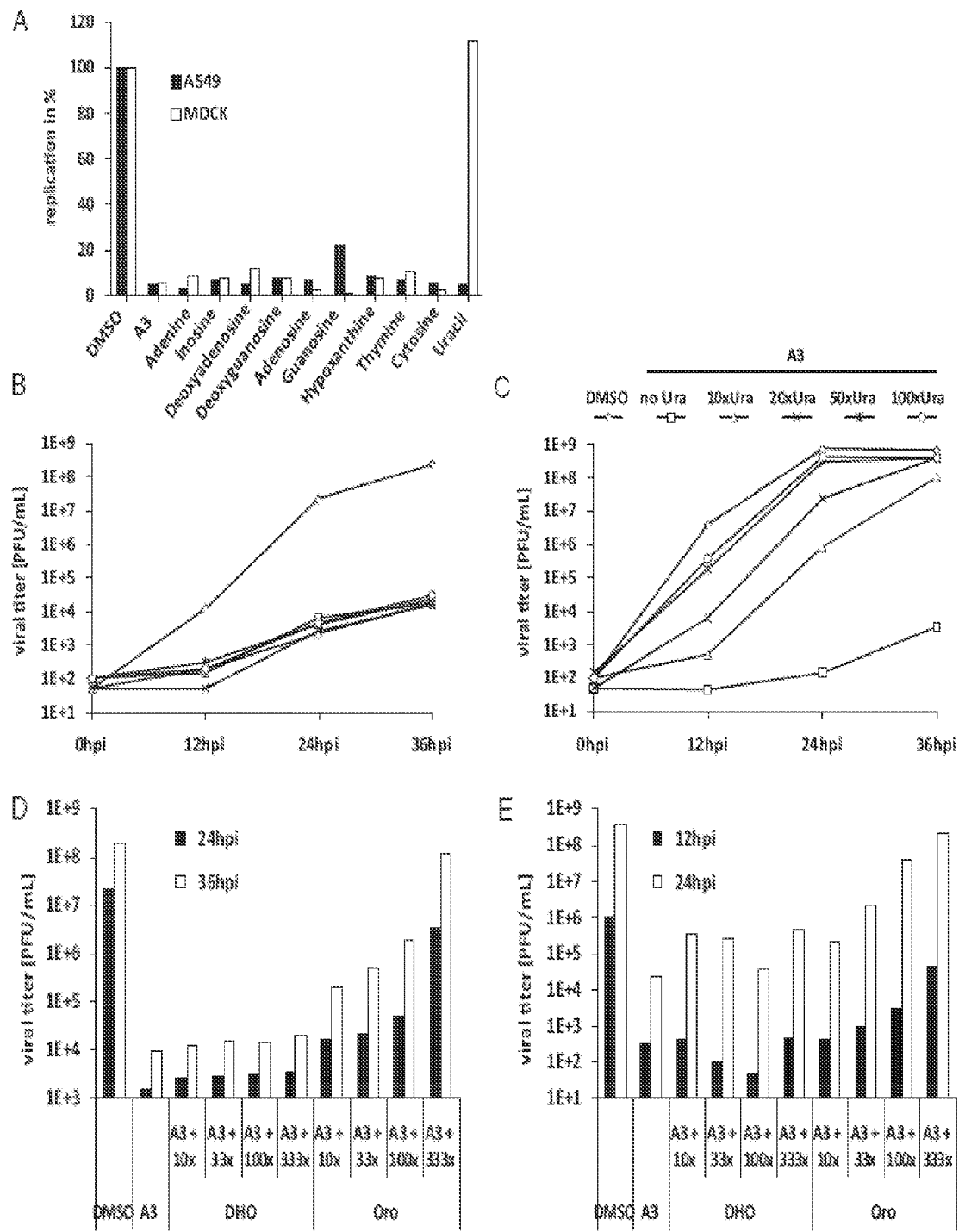

Replication was only partially inhibited by A3 in baby hamster kidney (BHK) cells and pig kidney (PK-15) cells, and the addition of uracil had no obvious effect. In contrast, A3 had no effect on viral replication in chicken fibroblast (DF-1) cells (FIG. 25B). This further underlines the possible species specificity of A3 and suggests that A3 may target a host cell protein. Of note, attempts to generate A3-resistant influenza viruses have been unsuccessful, which is another indication that a host factor may be the target of A3. The finding that uracil can reverse the inhibition of viral replication by A3, suggests that the pyrimidine pathway may be affected. Uracil is converted by the pyrimidine salvage pathway to uridine monophosphate (UMP), the base from which all other pyrimidines are manufactured in the cell. Besides the salvage of uracil, UMP is also generated via de novo biosynthesis. To distinguish between de novo biosynthesis and the salvage pathway, all intermediates of the pyrimidine biosynthesis cycle were tested for their ability to restore viral replication. Only orotic acid, which itself is converted in a two-step reaction by UMP synthase into UMP, was able to reverse the inhibition by A3 in both A549 and MDCK cells. Viral replication was tested in both cell lines in the presence of A3 alone or in combination with increasing concentrations of dihydroorotate (DHO) and orotate (FIGS. 24 D and E). DHO is converted by DHODH into orotate, which can rescue viral replication in a dose-dependent manner in contrast to DHO. Although DHO and orotate may not be equally efficient at entering cells or are equally stable, the dose-response seen with orotate provides a strong indication that DHODH activity may be targeted by A3. Leflunomide is a known weak inhibitor of DHODH and was tested in A549 and MDCK cells at a concentration of 10 µM for its effect on influenza virus replication. No inhibition was observed at this concentration, indicating that A3 is a superior inhibitor of DHODH compared with leflunomide. A sequence alignment of known DHODHs reveals ~90% sequence identity between the human and canine DHODH proteins but only ~73% between the human and chicken DHODH, which supports the idea of species-specific activity of A3.

A3 and its derivatives belong to a unique structural group of antiviral agents. The broad-spectrum antiviral activity of A3 is associated with de novo pyrimidine synthesis, and this feature contrasts with the activity of ribavirin and favipiravir, both of which target the purine pathway.

8.11 A3 Inhibits DHODH Activity In Vitro

In order to evaluate the inhibitory activity of A3 on DHODH activity, an in vitro assay for human DHODH activity was performed. Human dihydroorotate dehydrogenase (DHODH) was obtained from Origene Technologies (Rockville, Md.). The in vitro colorimetric DHODH assay monitors 2,6-dichloroindophenol (DCIP) reduction. The assay solution contains 100 mM HEPES, pH 8.0, 150 mM NaCl, 0.05% Triton X-100, 20 µM CoQ0 (Sigma, St Louis, Mo.), 200 µM L-dihydroorotate (Sigma, St Louis, Mo.), and 120 µM DCIP (Sigma, St Louis, Mo.). DCIP reduction was started by adding 50 nM DHODH (final reaction volume 50 µl in a 96 wells plate) and the enzymatic reaction was stopped by addition of 5 µl 10% sodium dodecyl sulphate. The absorbance of each well was measured at 600 nm using a microplate reader. Data was analyzed using Prism version 5.0.75% of DCIP was reduced after 60 minutes reaction time and this reaction time was used for analysis of inhibitory capacity of tested compounds.

Each compound was prepared as a 10 mM stock in DMSO and diluted to 50 µM in PBS. 10 µl inhibitor was transferred to 40 µl assay mixture to achieve a final concentration of 10 µM in each reaction. DHODH activity was determined after 60 mins by measuring DCIP reduction at 600 nM and compared to DHODH activity in the absence of inhibitor.

DHODH activity was compared in the presence of DMSO, A3, Leflunomide (active metabolite) and Leflunomide. The results were shown in FIG. 26A. In addition, relative DHODH inhibition and relative influenza virus inhibition were compared among A3 and its derivatives. The results were shown in FIG. 26B.

9. EQUIVALENTS

Those skilled in the art will recognize or be able to ascertain, using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed:

1. A method of treating or managing a viral infection, or preventing, treating or managing a pathological state resulting from a viral infection in a human subject comprising administering to a human subject in need thereof an effective amount of a compound of formula A3-H:

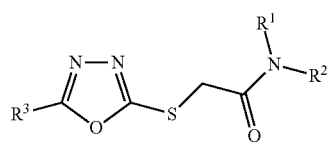
A3-H or a pharmaceutically acceptable salt, or stereoisomer thereof, wherein:
R$^1$ and R$^2$ are at each occurrence independently a C$_1$-C$_8$ alkyl group; or
R$^1$ and R$^2$, together with the nitrogen atom R$^1$ and R$^2$ are bound to, form a 3 to 10membered heterocyclic ring; and
R$^3$ is substituted or unsubstituted indole, wherein the viral infection is a positive-sens, single-stranded RNA virus infection, and wherein the virus is a member of flavivirus family.

2. The method of claim 1, wherein the compound is of formula A3-I:

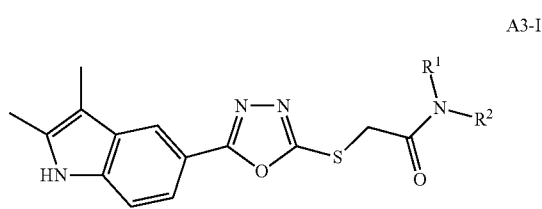
A3-I or a pharmaceutically acceptable salt or stereoisomer thereof, wherein:
R$^1$ and R$^2$ are at each occurrence independently a C$_1$-C$_8$ alkyl group; or
R$^1$ and R$^2$, together with the nitrogen atom R$^1$ and R$^2$ are bound to, form a 3 to 10membered heterocyclic ring.

3. The method of claim 1, wherein the compound is of formula A3-J:

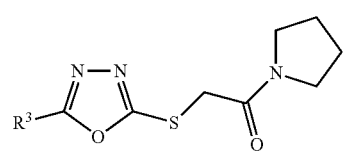
A3-J or a pharmaceutically acceptable salt, or stereoisomer thereof.

4. The method of claim 1, wherein the compound is selected from the group consisting of:

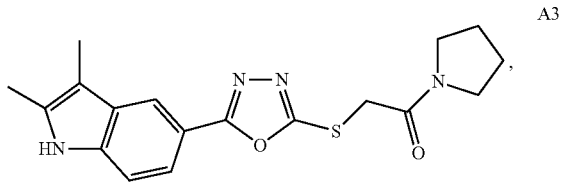
A3

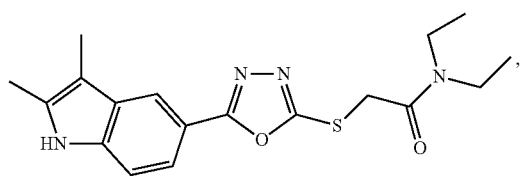
A3-2

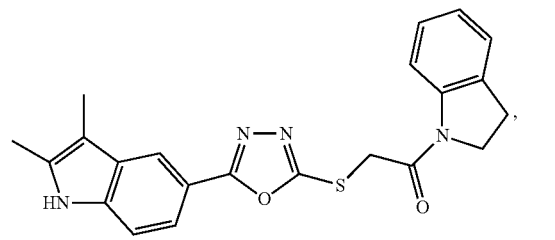
A3-3

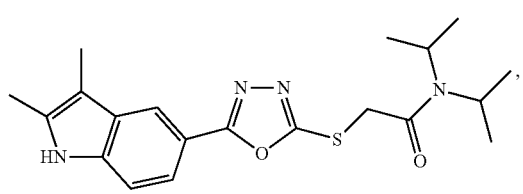
A3-4

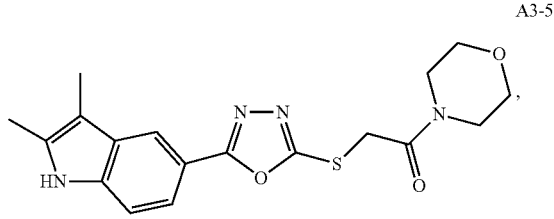

or a pharmaceutical acceptable salt thereof.

5. The method of claim 1, wherein the member of the flavivirus family (flaviviridae) is Dengue virus, hepatitis C virus, GB hepatitis viruses (GBV-A, GBV-B and GBV-C), West Nile virus, yellow fever virus, St. Louis encephalitis virus, Japanese encephalitis virus, Powassan virus, tick-borne encephalitis virus, or Kyasanur Forest disease virus.

6. The method of claim 5, wherein the virus is Dengue virus, hepatitis C virus or West Nile virus.

* * * * *